US008741600B2

(12) United States Patent
Yamaguchi et al.

(10) Patent No.: US 8,741,600 B2
(45) Date of Patent: Jun. 3, 2014

(54) METHOD FOR SEPARATION OF IMMUNOGLOBULIN MONOMERS

(75) Inventors: Fumihiko Yamaguchi, Tokyo (JP); Hitoshi Mizomoto, Tokyo (JP); Shinya Hamasaki, Tokyo (JP); Takena Mochizuki, Tokyo (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 427 days.

(21) Appl. No.: 12/665,651

(22) PCT Filed: Jun. 18, 2008

(86) PCT No.: PCT/JP2008/061164
§ 371 (c)(1),
(2), (4) Date: Feb. 23, 2010

(87) PCT Pub. No.: WO2008/156124
PCT Pub. Date: Dec. 24, 2008

(65) Prior Publication Data
US 2010/0190965 A1    Jul. 29, 2010

(30) Foreign Application Priority Data

| Jun. 19, 2007 | (JP) | 2007-161048 |
| Jan. 31, 2008 | (JP) | 2008-021068 |
| Jan. 31, 2008 | (JP) | 2008-021079 |
| Jan. 31, 2008 | (JP) | 2008-021080 |
| Feb. 1, 2008  | (JP) | 2008-022346 |
| Feb. 1, 2008  | (JP) | 2008-022349 |
| Feb. 1, 2008  | (JP) | 2008-022358 |
| Feb. 1, 2008  | (JP) | 2008-022363 |
| Feb. 1, 2008  | (JP) | 2008-022471 |
| Feb. 1, 2008  | (JP) | 2008-022472 |
| Feb. 1, 2008  | (JP) | 2008-022473 |
| Feb. 25, 2008 | (JP) | 2008-042380 |
| Feb. 25, 2008 | (JP) | 2008-042381 |
| Mar. 4, 2008  | (JP) | 2008-053148 |
| Mar. 14, 2008 | (JP) | 2008-066676 |

(51) Int. Cl.
*G01N 33/48* (2006.01)

(52) U.S. Cl.
USPC ........... 435/69.6; 436/516; 436/534; 435/326

(58) Field of Classification Search
None
See application file for complete search history.

(56) References Cited

U.S. PATENT DOCUMENTS

| 4,333,870 A    | 6/1982  | Koyama et al.             |
| 6,124,437 A    | 9/2000  | Hirao et al.              |
| 6,267,958 B1 * | 7/2001  | Andya et al. ..... 424/130.1 |
| 6,365,395 B1   | 4/2002  | Antoniou                  |
| 2009/0127186 A1| 5/2009  | Mizomoto et al.           |

FOREIGN PATENT DOCUMENTS

| JP | 56-59716 A       | 5/1981  |
| JP | 10-265406 A      | 10/1998 |
| JP | 2003-12693 A     | 1/2003  |
| WO | WO-02/13859 A1   | 2/2002  |
| WO | WO-2007/018284 A1| 2/2007  |

OTHER PUBLICATIONS

Litzén et al., "Separation and Quantitation of Monoclonal Antibody Aggregates by Asymmetrical Flow Field-Flow Fractionation and Comparison to Gel Permeation Chromatography", Analytical Biochemistry, 1993, vol. 212, No. 2, p. 469-480.

\* cited by examiner

*Primary Examiner* — Yunsoo Kim
(74) *Attorney, Agent, or Firm* — Birch, Stewart, Kolasch & Birch, LLP

(57) ABSTRACT

A method of accurately separating immunoglobulin monomers by subjecting an immunoglobulin solution containing at least immunoglobulin monomers and immunoglobulin aggregates to cross-flow filtration using an ultrafiltration membrane, an ultrafiltration membrane module, and a cross-flow filtration apparatus. The method can separate immunoglobulin monomers by subjecting an immunoglobulin solution containing at least immunoglobulin monomers and immunoglobulin aggregates and having an immunoglobulin concentration of 1 to 150 g/L to cross-flow filtration using an ultrafiltration membrane having a molecular weight cut-off of 100,000 or more and less than 500,000 so that immunoglobulin monomers passes through the ultrafiltration membrane with a permeability of 80% or more while achieving a fractionation performance in which the permeability ratio of immunoglobulin dimers to immunoglobulin monomers that pass through the ultrafiltration membrane is 0.20 or less.

39 Claims, 11 Drawing Sheets

METHOD FOR SEPARATION OF IMMUNOGLOBULIN MONOMERS

TECHNICAL FIELD

The present invention relates to a method for accurately separating immunoglobulin monomers by subjecting an immunoglobulin solution containing at least immunoglobulin monomers and immunoglobulin aggregates to cross-flow filtration using an ultrafiltration membrane, as well as the ultrafiltration membrane module and the cross-flow filtration apparatus.

BACKGROUND ART

Immunoglobulin (antibody) is mainly present in blood and body fluids and binds to microorganisms (e.g. bacteria and viruses) that have invaded the body or to the cells infected by microorganisms, while recognizing them as antigens. When an antibody has bound to an antigen, a phagocyte (e.g., leukocyte or macrophage) engulfs the antigen-antibody complex to remove them from the body, or an immunocyte (e.g., lymphocyte) binds to the complex to induce immune reactions. The immunoglobulin thus has an important role in the defense mechanism against infections.

The immunoglobulin may be separated by separation/purification from biocomponents (mainly blood), or separation/purification from the cells (e.g., hybridoma), for example. Since more than 100,000 kinds of microorganisms, proteins, DNA, RNA, and viruses exist in the biocomponent, it is necessary to separate such other constituents from the immunoglobulin.

Multiple immunoglobulin molecules may also form immunoglobulin aggregates (mainly dimers) by bonding to each other via non-covalent bonds. The immunoglobulin aggregate is considered to be a cause of the side effects that occur when an immunoglobulin preparation is injected intravenously into the human body, such as shock reaction (e.g., cyanosis or pressure drop), airway symptom (e.g., respiratory difficulty), or rash. The immunoglobulin tend to agglomerate to produce larger multimers which may cause cloudiness or precipitation in the immunoglobulin solution. The immunoglobulin may bond to another protein, a bacterium, a virus, or the like to form a large protein aggregate that is referred to as an antigen-antibody complex. It is difficult to decompose the immunoglobulin aggregate that has been formed. Therefore, various methods have been proposed to remove such aggregates from a solution.

Several purification methods have been reported to separate immunoglobulin monomers from a solution containing immunoglobulin monomers and immunoglobulin aggregates. Examples of such purification methods include ion-exchange chromatography, hydrophobic chromatography, gel chromatography, the chemical treatment method, the adsorption method, and the ultrafiltration membrane method.

Ion-exchange chromatography and hydrophobic chromatography are effective for separating substances that differ in charge or hydrophobicity to a large extent. However, substances that differ in charge or hydrophobicity to only a small extent (e.g., immunoglobulin monomers and an immunoglobulin dimer) cannot be sufficiently separated. Moreover, a large amount of eluent or salt is necessary which is another drawback of these methods.

Gel chromatography that utilizes the size separation principle is effective for separating immunoglobulin monomers and immunoglobulin dimers that differ in size. However, since a large amount of immunoglobulin cannot be processed by gel chromatography, gel chromatography is time-consuming and costly.

A large amount of immunoglobulin can be processed by a chemical treatment that adds chemical substances. However, it is necessary to subsequently remove the chemicals used for the treatment from the solution. Moreover, inactivation or denaturation of the immunoglobulin easily occurs due to the treatment so that the immunoglobulin permeability may decrease.

The adsorption method does not necessarily exhibit a high immunoglobulin dimer removal efficiency. Moreover, it is necessary to remove the adsorbent as in the chemical treatment method.

In recent years, the ultrafiltration membrane method that is robust and convenient and can process a large amount of proteins has attracted attention. Various reports have been made on the ultrafiltration membrane method. When separating two components by ultrafiltration, it is understood that the fractionation performance and the permeation amount are affected by the cake layer that is formed on the surface of the ultrafiltration membrane. The molecular weight cut-off of the ultrafiltration membrane and the concentration of the particles (e.g., proteins) that form the cake layer are speculated to be important factors for the formation of the cake layer. However, since it is difficult to analyze the cake layer, few methods have been available for controlling cake layer formation.

For example, Non-patent Document 1, which reports separation of bovine serum albumin and lysozyme, does not contain any description on a cake layer analysis or a control method. Non-patent Document 1 is also silent about separation of immunoglobulin monomers and dimers.

As an immunoglobulin membrane separation method, Patent Document 1 discloses a method that removes globulin dimers by filtration using an ultrafiltration membrane formed of a polysulfone polymer. However, since the method disclosed in Patent Document 1 is a dead-end method, a large amount of immunoglobulin is captured in the membrane so that a thick cake layer is formed (i.e., clogging of the membrane occurs). Therefore, the immunoglobulin monomer permeability is quite low (about 40%), Moreover, the filtration speed and the filtration capacity are also decreased. This impairs the industrial effectiveness of the method disclosed in Patent Document 1.

Patent Document 2 discloses a method that removes immunoglobulin aggregates by dead-end filtration using a regenerated cellulose hollow fiber membrane. However, since the pore diameter (molecular weight cut-off) of the membrane is large, the immunoglobulin dimer is removed to only a small extent. Therefore, the method disclosed in Patent Document 2 is not sufficient for separating the immunoglobulin dimer.

When a large amount of impurities are contained in a solution, a cross-flow filtration method that rarely causes clogging of the membrane is generally utilized taking account of the membrane capturing capacity. Patent Document 3 discloses a method that removes immunoglobulin dimers by cross-flow filtration using an ultrafiltration membrane. However, Patent Document 3 is silent about the immunoglobulin monomer/dimer fractionation performance. In Patent Document 3, since filtration is performed at a very low concentration, it is considered that a cake layer that can separate immunoglobulin monomers and dimers is not sufficiently formed.

Patent Document 4 discloses a method that separates biocomponents that differ in molecular weight by a factor of less than 10 by cross-flow filtration while maintaining a level within the range of 5 to 100% of the flux at the transition point. Patent Document 4 discloses separation of proteins having a molecular weight of 100,000, but discloses no data about immunoglobulin monomer/dimer separation.

Patent Document 5 discloses a method that removes aggregates from an aqueous solution of immunoglobulin fractionated from human plasma, and filters the solution using a polyolefin porous membrane in the presence of a stabilizer with surface activity to reduce the anti-complement activity. However, Patent Document 5 discloses no data about immunoglobulin monomer/dimer separation. Moreover, Patent Document 5 states that it is preferable to use a membrane having a pore diameter that allows immunoglobulin aggregates (trimer and higher structures) to pass through the membrane. Thus, it is difficult to separate immunoglobulin monomers and immunoglobulin dimers using such a membrane.

Patent Document 6 states that immunoglobulin dimers can be removed using a membrane for separating plasma from blood. However, it is considered that the removal effect of such a membrane does not depend on the relationship between the sizes of the dimer and the pore. Instead the removal effect of the membrane is given due to adsorption of immunoglobulin dimers on the surface of the membrane caused by interaction between the membrane material and immunoglobulin dimers. Therefore, it is necessary to use the membrane under conditions (e.g., the pH of the solution and the ion intensity) in which adsorption occurs. Often the desired removal effect may not be obtained due to only a small change in conditions. When using the above method, the solution is likely to be contaminated with microorganisms (e.g., bacteria and viruses) from the outside during the operation. It is very important to prevent such a situation when producing a medicine. Therefore, it is necessary to inactivate or remove such microorganisms contained in the immunoglobulin solution which has been subjected to immunoglobulin dimer-removal treatment.

Cross-flow filtration is generally performed by means of constant-volume filtration that adds a diluent to the biocomponent solution in an amount equal to that of the immunoglobulin permeation solution (see Patent Documents 3 and 4). However, since the concentration of the biocomponent solution decreases as filtration proceeds, it may take long time in order to achieve a recovery rate of 80% or more.

Aggregates may be produced or cloudiness may occur in the immunoglobulin solution during cross-flow filtration using an ultrafiltration membrane. It is considered that this occurs when the immunoglobulin itself or associated impurities are insolubilized and aggregate due to stress applied to the immunoglobulin as a result of ultrafiltration. Since aggregation or cloudiness affects the permeation amount and the fractionation performance, it is important to suppress aggregation or cloudiness.

Aggregation of the immunoglobulin may be suppressed by adjusting the salt concentration or controlling the pH of the solution (Patent Document 7). A phosphate is used as an aggregation inhibitor. However, since a sufficient aggregation inhibiting effect is not obtained when the salt concentration is low, the salt used as an aggregation inhibitor is normally added in excess. As a result, precipitation of the immunoglobulin may occur. In this case, a subsequent desalting process is necessary and this increases the cost. Also, the immunoglobulin may be adversely denaturated when suppressing aggregation by controlling the pH of the solution.

Patent Document 8 discloses a method for suppressing formation of aggregates and cloudiness using sorbitan. However, the permeability decreases when adding sorbitan in an amount necessary to achieve a sufficient suppression effect.

When purifying the immunoglobulin, virus clearance ability is required in each purification step. The Paul-Ehrlich Institute (Germany) recommends that the sum of the log reduction values (LRV), of purification methods that differ in principle, be 10 or more (enveloped virus) or 6 or more (non-enveloped virus). A membrane that separates immunoglobulin monomers is also required to exhibit virus clearance ability. However, the virus clearance ability of an ultrafiltration membrane that separates immunoglobulin monomers and immunoglobulin dimers has not been reported.

Patent Document 1: JP S62-3815 B
Patent Document 2: JP H6-279296 A
Patent Document 3: Japanese Patent No. 3746223
Patent Document 4: Japanese Patent No. 3828143
Patent Document 5: JP H7-78025 B
Patent Document 6: JP S61-69732 A
Patent Document 7: JP 2004-267830 A
Patent Document 8: WO02/013859
Non-Patent Document 1: Separation Science and Technology, 33(2), 169-185 (1998)

DISCLOSURE OF THE INVENTION

Problem to be Solved by the Invention

An object of the present invention is to provide a method of accurately separating immunoglobulin monomers by subjecting an immunoglobulin solution containing at least immunoglobulin monomers and immunoglobulin aggregates to cross-flow filtration using an ultrafiltration membrane, as well as an ultrafiltration membrane module and a cross-flow filtration apparatus for the method.

Means for Solving the Problem

The inventors of the present invention conducted extensive studies in order to achieve the above object. As a result, the inventors found that an increase in fractionation performance and an increase in throughput have a trade-off relationship in an immunoglobulin monomer-purification method that uses an ultrafiltration membrane having a molecular weight cut-off of 100,000 or more and less than 500,000, and high fractionation performance can be achieved without decreasing the throughput by optimizing the molecular weight cut-off of the ultrafiltration membrane and the concentration of the immunoglobulin solution. The inventors also found that a high-purity immunoglobulin monomer can be efficiently purified within a short time by maintaining a substantially constant concentration of the immunoglobulin solution during filtration.

The inventors thus conceived a method that can separate immunoglobulin monomers by subjecting an immunoglobulin solution containing at least immunoglobulin monomers and immunoglobulin aggregates and having an immunoglobulin concentration of 1 to 150 g/L to cross-flow filtration using an ultrafiltration membrane having a molecular weight cut-off of 100,000 or more and less than 500,000 so that immunoglobulin monomers passe through the ultrafiltration membrane with a permeability of 80% or more while achieving a fractionation performance in which the permeability ratio of immunoglobulin dimers to immunoglobulin monomers that pass through the ultrafiltration membrane is 0.20 or less, as well as an ultrafiltration membrane module and a cross-flow filtration apparatus for the method.

Specifically, the present invention provides the following.
[1] A method of separating immunoglobulin monomers comprising subjecting an immunoglobulin solution containing at least immunoglobulin monomers and immunoglobulin aggregates and having an immunoglobulin concentration of 1 to 150 g/L to cross-flow filtration using an ultrafiltration membrane having a molecular weight cut-off of 100,000 or more and less than 500,000.

[2] A method of separating immunoglobulin monomers from immunoglobulin aggregates comprising subjecting an immunoglobulin solution having an immunoglobulin concentration of 1 to 150 g/L to cross-flow filtration using an ultrafiltration membrane having a molecular weight cut-off of 100,000 or more and less than 500,000.

[3] The method according to [1] or [2], wherein the aggregates include at least an immunoglobulin dimer.

[4] The method according to any one of [1] to [3], wherein the immunoglobulin solution has an immunoglobulin concentration of 1 to 100 g/L.

[5] The method according to any one of [1] to [3], wherein the immunoglobulin solution has an immunoglobulin concentration of 5 to 100 g/L.

[6] The method according to any one of [1] to [5], wherein the cross-flow filtration is performed while maintaining a change in the immunoglobulin concentration within the range of 50 to 200 when the immunoglobulin concentration is referred to as 100.

[7] The method according to [6], wherein the cross-flow filtration is performed while maintaining a change in the immunoglobulin concentration within the range of 80 to 120.

[8] The method according to [6] or [7], wherein the cross-flow filtration is performed while maintaining a substantially constant immunoglobulin concentration.

[9] The method according to any one of [6] to [8], wherein 50% or more of immunoglobulin monomers are separated by the method.

[10] The method according to any one of [1] to [9], wherein the immunoglobulin solution further contains at least one biocomponent selected from a protein having a molecular weight of 300,000 or more and less than 1,000,000, a sugar chain, RNA, and DNA.

[11] The method according to [10], wherein the immunoglobulin solution further contains at least one biocomponent selected from a protein having a molecular weight of 300,000 or more and less than 1,000,000.

[12] The method according to [11], wherein the protein is at least one protein selected from the group consisting of an immunoglobulin aggregate, fibrinogen, and a composite aggregate of an immunoglobulin and protein A.

[13] The method according to any one of [1] to [12], wherein the immunoglobulin solution further contains a virus.

[14] The method according to [13], wherein the virus is a parvovirus.

[15] The method according to any one of [1] to [14], wherein the immunoglobulin is a monoclonal antibody.

[16] The method according to any one of [1] to [15], wherein the ultrafiltration membrane is formed of at least one polymer selected from the group consisting of a polysulfone polymer, an aromatic ether polymer, a (meth)acrylic polymer, a (meth)acrylonitrile polymer, a fluorinated polymer, an olefin polymer, a vinyl alcohol polymer, and a cellulose polymer.

[17] The method according to [16], wherein the polymer is a polysulfone polymer.

[18] The method according to [17], wherein the polysulfone polymer is at least one polysulfone polymer selected from polysulfone polymers shown by the following formulas (5) to (7), or a mixture of two or more of the polysulfone polymers shown by the following formulas (5) to (7),

[Chem 5]

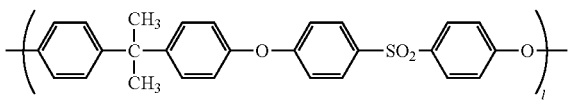

(5)

wherein l represents the number of repeating units,

[Chem 6]

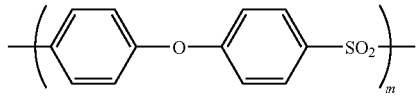

(6)

wherein m represents the number of repeating units,

[Chem 7]

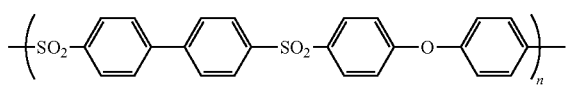

(7)

wherein n represents the number of repeating units.

[19] The method according to [17] or [18], wherein the polysulfone polymer has been hydrophilized with polyvinylpyrrolidone.

[20] The method according to [16], wherein the polymer is an aromatic ether polymer.

[21] The method according to [20], wherein the aromatic ether polymer is at least one aromatic ether polymer shown by the following formula (8), and has been hydrophilized with a block copolymer of polystyrene and a hydrophilic polymer,

[Chem 8]

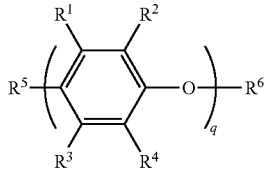

(8)

wherein $R^1$, $R^2$, $R^3$, $R^4$, $R^5$, and $R^6$ individually represent hydrogen, an organic functional group having 1 to 6 carbon atoms, or a non-protonic organic functional group having at most 6 carbon atoms and containing oxygen, nitrogen, or silicon. Each of them can be the same and different each other. And q represents the number of repeating units, provided that the aromatic ether polymer may be a copolymer containing two or more different repeating units.

[22] The method according to [21], wherein the hydrophilic polymer is a polyethylene glycol polymer and/or a polymer containing a segment derived from a polyethylene glycol polymer.

[23] The method according to any one of [1] to [22], wherein the immunoglobulin solution further contains a surfactant.

[24] The method according to [23], wherein the surfactant is an amphoteric surfactant.

[25] The method according to [24], wherein the amphoteric surfactant is selected from the group consisting of lysine, alanine, cysteine, glycine, serine, proline, arginine, and derivatives thereof.

[26] The method according to [25], wherein the amphoteric surfactant is arginine and/or an arginine derivative.

[27] The method according to [25], wherein the amphoteric surfactant is lysine and/or a lysine derivative.

[28] The method according to [23], wherein the surfactant is a non-ionic surfactant.

[29] The method according to [28], wherein the non-ionic surfactant is polyethylene glycol and/or a polyethylene glycol derivative.

[30] The method according to [29], wherein the polyethylene glycol and/or the polyethylene glycol derivative have a number average molecular weight of 50 to 30000 Da.

[31] The method according to any one of [1] to [30], further comprising recycling an immunoglobulin permeation solution to an immunoglobulin stock solution until a given time is reached after starting filtration.

[32] The method according to [31], wherein the given time for recycling an immunoglobulin permeation solution to an immunoglobulin stock solution is set as a time when the percentage of immunoglobulin dimers contained in the immunoglobulin permeation solution has reached 1% or less.

[33] The method according to [31], wherein the given time for recycling an immunoglobulin permeation solution to an immunoglobulin stock solution is set as a time when the ratio of immunoglobulin dimer permeability to immunoglobulin monomer permeability has reached 0.1 or less.

[34] The method according to any one of [1] to [33], the method being used after the step of purifying the immunoglobulin solution by affinity chromatography.

[35] The method according to [34], wherein the affinity chromatography utilizes protein A and/or a protein A derivative as an adsorbent.

[36] The method according to any one of [1] to [35], wherein the ultrafiltration membrane is a hollow fiber membrane.

[37] The method according to any one of [1] to [36], the method being implemented using an apparatus that comprises at least one of (a) means that monitors the concentration of the immunoglobulin stock solution, (b) means that controls the concentration of the immunoglobulin stock solution, (c) means that controls the linear velocity of the immunoglobulin stock solution, and (d) means that controls the filtration pressure through the ultrafiltration membrane.

[38] A module and an apparatus comprising a module and at least one of (a) means that monitors the concentration of the immunoglobulin stock solution, (b) means that controls the concentration of the immunoglobulin stock solution, (c) means that controls the linear velocity of the immunoglobulin stock solution, and (d) means that controls the filtration pressure through the ultrafiltration membrane, used to implement the method according to any one of [1] to [36].

[39] A separation/concentration method comprising a separation step that implements the method according to any one of [1] to [37], and a concentration step that concentrates the immunoglobulin permeation solution obtained by the separation step using a ultrafiltration membrane for concentration, the separation step and the concentration step being performed continuously.

[40] The separation/concentration method according to [39], wherein the ultrafiltration membrane for concentration has a molecular weight cut-off of 1,000 or more and less than 100,000.

[41] The separation/concentration method according to [39] or [40], wherein the concentration of the immunoglobulin permeation solution subjected to the separation step according to any one of [1] to [3] and [6] to [37] is 0.1 to 149 g/L, and cross-flow filtration is performed in the concentration step at a linear velocity of 0.01 to 100 cm/sec and a pressure of 0.01 to 0.5 MPa.

[42] The separation/concentration method according to [39] or [40], wherein the concentration of the immunoglobulin permeation solution subjected to the separation step that implements the method according to any one of [1] to [37] is 0.1 to 99 g/L, and cross-flow filtration is performed in the concentration step at a linear velocity of 0.01 to 100 cm/sec and a pressure of 0.01 to 0.5 MPa.

[43] The separation/concentration method according to any one of [39] to [42], the method being implemented using a module utilizing the ultrafiltration membrane, and at least one of (a) means that monitors the concentration of the immunoglobulin stock solution, (b) means that controls the concentration of the immunoglobulin stock solution, (c) means that controls the linear velocity of the immunoglobulin stock solution, and (d) means that controls the filtration pressure through the ultrafiltration membrane, and a module utilizing the ultrafiltration membrane for concentration, and at least one of (e) means that monitors the concentration of the immunoglobulin permeation solution before concentration, (f) means that monitors the concentration of the immunoglobulin permeation solution after concentration, (g) means that controls the linear velocity of the immunoglobulin permeation solution, and (h) means that controls the filtration pressure through the ultrafiltration membrane for concentration.

[44] An apparatus used to implement the separation/concentration method according to any one of [39] to [42], the apparatus comprising a module utilizing the ultrafiltration membrane, and at least one of (a) means that monitors the concentration of the immunoglobulin stock solution, (b) means that controls the concentration of the immunoglobulin stock solution, (c) means that controls the linear velocity of the immunoglobulin stock solution, and (d) means that controls the filtration pressure through the ultrafiltration membrane, and a module utilizing the ultrafiltration membrane for concentration, and at least one of (e) means that monitors the concentration of the immunoglobulin permeation solution before concentration, (f) means that monitors the concentration of the immunoglobulin permeation solution after concentration, (g) means that controls the linear velocity of the immunoglobulin permeation solution, and (h) means that controls the filtration pressure through the ultrafiltration membrane for concentration.

Effects of the Invention

The separation method according to the present invention can separate immunoglobulin monomers so that immunoglobulin monomers passes through the ultrafiltration membrane with a permeability of 80% or more while achieving fractionation performance in which the permeability ratio of immunoglobulin dimers to immunoglobulin monomers that pass through the ultrafiltration membrane is 0.20 or less.

According to the present invention, since the immunoglobulin solution is merely subjected to cross-flow filtration using an ultrafiltration membrane having a given molecular weight cut-off, the operation is very simple as compared with chromatography and the like. Therefore, a large amount of immunoglobulin can be processed. The present invention does not cause inactivation or modification of the immunoglobulin, differing from a chemical treatment. Moreover, since clogging of the membrane does not occur, though that is often the case with known separation method using a membrane, immunoglobulin monomers can be efficiently collected while efficiently removing immunoglobulin dimers.

EXPLANATION OF SYMBOLS

Figure 1:
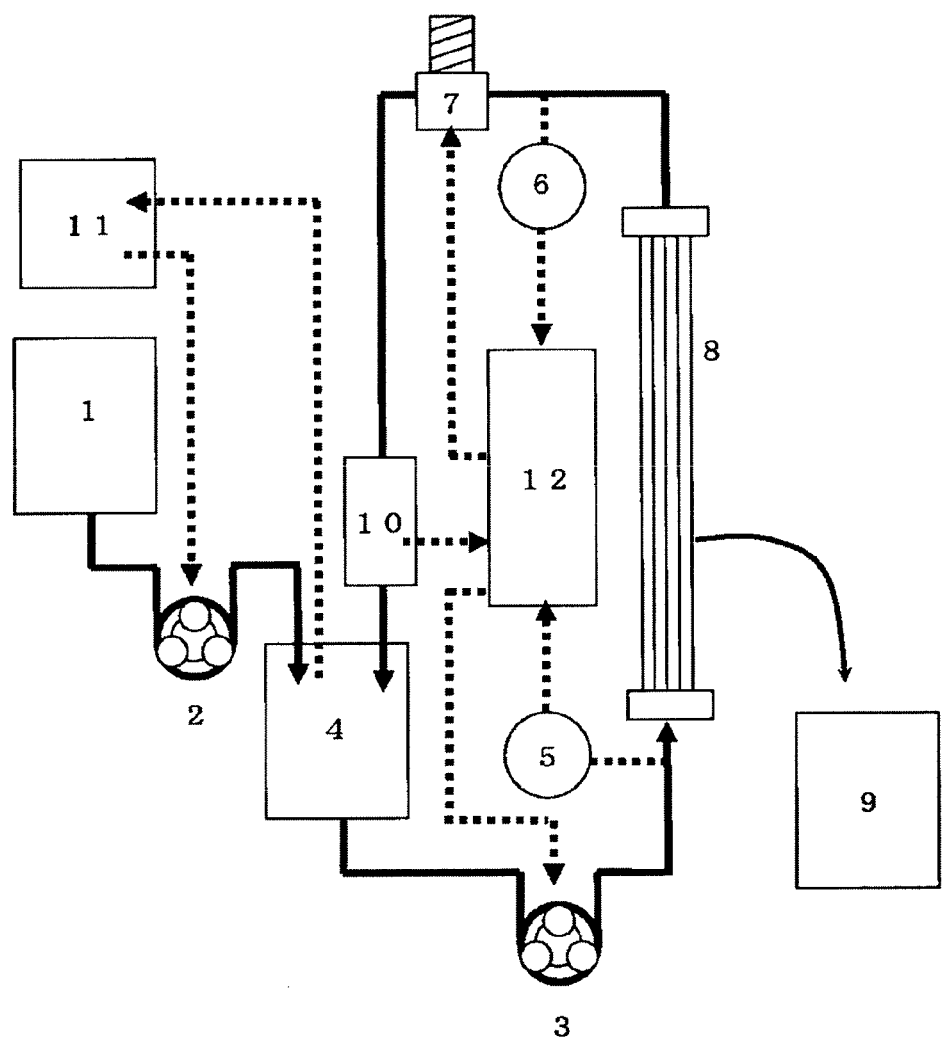
FIG. 1 is a view showing an example of cross-flow filtration apparatus according to the present invention.

1: Diluent tank
2: Supply pump 1
3: Supply pump 2
4: Immunoglobulin stock solution tank
5: Manometer 1
6: Manometer 2
7: Control valve 1
8: Ultrafiltration membrane module
9. Immunoglobulin permeation solution tank
10: Flowmeter 1
11: Concentration controller 1
12: Pressure/flow rate controller 1
13: UV flow cell
14: Concentration controller 2
15: Supply pump 3
16: Manometer 3
17: Manometer 4
18: Pressure/flow rate controller 2
19: Control valve 2
20: Absorption spectrometer
21: Concentrated immunoglobulin solution tank
22: Flowmeter 2
23: Switch valve
24: Ultrafiltration membrane-for-concentration module
31: Pressure regulator
32: Manometer 4
33: Immunoglobulin stock solution tank
34: Valve 1
35: Valve 2
36: Ultrafiltration membrane module
37: Permeation solution tank

BEST MODE FOR CARRYING OUT THE INVENTION

The method of accurately separating immunoglobulin monomers using an ultrafiltration membrane, the ultrafiltration membrane module, and the cross-flow filtration apparatus according to the present invention are described in detail below.

The term "immunoglobulin (antibody)" according to the present invention is used in the broadest sense. Specific examples of the immunoglobulin include a monoclonal antibody (including a whole monoclonal antibody), a polyclonal antibody, a multi-specific antibody (e.g., bispecific antibody), and the like.

The term "immunoglobulin aggregate" according to the present invention refers to immunoglobulins that form a dimer or a higher structure due to hydrophobic bonding or the like. Examples of the immunoglobulin aggregate include an immunoglobulin dimer, an immunoglobulin trimer, an immunoglobulin tetramer, an immunoglobulin pentamer, and the like.

The term "monoclonal antibody" according to the present invention refers to an antibody obtained from a substantially homogenous antibody population. Specifically, each antibody that forms the population is identical except for rare mutations that may occur naturally. The monoclonal antibody is very specific, and is directed toward a single antigenic site. Each monoclonal antibody is normally directed toward a single determinant on the antigen, differing from a polyclonal antibody that includes different antibodies. The modifier "monoclonal" refers to the feature of the antibody that is obtained from a substantially homogenous antibody population.

Examples of the immunoglobulin (antibody) according to the present invention include a natural human antibody, a humanized antibody, a human antibody, and a fully humanized antibody prepared by genetic recombination, a chimeric antibody, a mouse antibody, and the like.

Specific examples of the antibody according to the present invention include an anti-HER2 receptor antibody, an anti-CD20 antibody, an anti-IL-8 antibody, an anti-VEGF antibody, an anti-PSCA antibody, an anti-CD11a antibody, an anti-IgE antibody, an anti-Apo-2 receptor antibody, an anti-TNF-α antibody, an anti-tissue factor (TF) antibody, an anti-CD3 antibody, an anti-CD25 antibody, an anti-CD34 antibody, an anti-CD40 antibody, an anti-tac antibody, an anti-CD4 antibody, an anti-CD52 antibody, an anti-Fc receptor antibody, an anti-carcinoembryonic antigen (CEA) antibody, an antibody specific to breast epithelial cells, an antibody that binds to colonic cancer cells, an anti-CD33 antibody, an anti-CD22 antibody, an anti-EpCAM antibody, an anti-GpIIb/IIIa antibody, an anti-RSV antibody, an anti-CMV antibody, an anti-HIV antibody, an anti-hepatitis antibody, an anti-$\alpha v \beta 33$ antibody, an anti-human renal cell carcinoma antibody, an anti-human 17-1A antibody, an anti-human colorectal tumor antibody, an anti-human melanoma antibody, an anti-human squamous cell carcinoma antibody, an anti-human leucocyte antigen (HLA) antibody, and the like. More specific examples of the antibody according to the present invention include Muromomab (trade name: Orthclone (OKT3)), Rituximab (trade name: Ritaxan), Basiliximab (trade name: Simulect), Daclizumab (trade name: Zenapax), Palivizumab (trade name: Synagis), Infliximab (trade name: Remicade), Gemtuzumab zogamicn (trade name: Mylotarg), Alemtuzumab (trade name: Mabcampath), Adalimumab (trade name: Humira), Omalizumab (trade name: Xolair), Vevacizumab (trade name: Avastin), Cetuximab (trade name: Erbitux), and the like.

Examples of a molecular target (antigen) of the immunoglobulin (antibody) according to the present invention include CD proteins (e.g., CD3, CD4, CD8, CD19, CD20, CD34, and CD40); an HER receptor family (e.g., EGF receptor, HER2, HER3, or HER4 receptor); cell adhesion molecules (e.g., LFA-1, Mac1, p 150, 95, VLA-4, ICAM-1, VCAM, and members of the Av/b3 integrins including a subunit a orb (e.g., anti-CD11a, anti-CD18, or anti-CD11b antibody); growth factors (e.g., VEGF); IgE and a blood group antigen; an Flk2/flt3 receptor; an obesity (OB) receptor; an mpl receptor; a CTLA-4; protein C; and the like. A soluble antigen or a fragment that binds to another molecule is also a molecular target. For example, a fragment in the extracellular region of a receptor (transmembrane molecule) serves as an immunizing antigen. A cell that expresses a transmembrane molecule may also serve as an immunizing antigen.

The concentration of the immunoglobulin solution significantly affects formation of a cake layer. It is necessary to form an appropriate cake layer in order to exert fractionation performance. It is necessary to take account of the lower limit of the concentration of the immunoglobulin solution so that a cake layer is formed within a short time.

The lower limit of the concentration of the immunoglobulin solution according to the present invention is 1 g/L or more, and preferably 5 g/L or more, so that a cake layer that exhibits fractionation performance is formed.

A thick cake layer is formed when the concentration of the immunoglobulin solution is high so that the permeability of immunoglobulin monomers decreases. Therefore, it is necessary to take account of the upper limit of the concentration of the immunoglobulin solution so that clogging of the membrane does not occur.

The upper limit of the concentration of the immunoglobulin solution according to the present invention is 150 g/L or less, preferably 100 g/L or less, and more preferably 50 g/L or less, so that immunoglobulin monomers can pass through the membrane without causing a rapid clogging of the membrane.

Specifically, the concentration of the immunoglobulin solution is 1 to 150 g/L, preferably 1 to 100 g/L, more preferably 5 to 100 g/L, and still more preferably 5 to 50 g/L, so that an appropriate cake layer is formed.

It is preferable to filter the immunoglobulin solution without changing the concentration of the immunoglobulin solution during filtration in order to maintain the fractionation performance for immunoglobulin monomers and immunoglobulin dimers and the permeability of immunoglobulin monomers. For example, when the concentration of the immunoglobulin solution gradually increases during filtration, clogging may occur so that the permeability of immunoglobulin monomers may become insufficient.

When employing constant-volume cross-flow filtration that adds a diluent in an amount equal to the permeation amount (see Patent Documents 3 and 4), the concentration of the immunoglobulin solution decreases as filtration proceeds. In this case, the concentration of the immunoglobulin solution that passes through the membrane decreases in the second half of filtration. As a result, a long time is required to collect immunoglobulin monomers in high yield. Therefore, in order to achieve high fractionation performance and permeability within a short time, it is preferable to filter the immunoglobulin solution while maintaining a constant concentration of the immunoglobulin solution (constant-concentration filtration).

A change in the concentration of the immunoglobulin solution during filtration is, as a lower limit, 50 or more, preferably 70 or more, and more preferably 80 or more, and, as an upper limit, 200 or less, preferably 150 or less, and more preferably 120 or less, when the concentration of the immunoglobulin solution before filtration is referred to as 100. It is most preferable to subject the immunoglobulin solution to cross-flow filtration while maintaining the concentration of the immunoglobulin solution substantially constant. The expression "while maintaining the concentration . . . substantially constant" used herein has the same meaning as the expression "while suppressing the change in concentration". For example, a small change in concentration may occur when controlling the concentration of the immunoglobulin solution by an operation or by an apparatus. However, when the amount of the immunoglobulin solution has decreased in the second half of filtration so that filtration has become difficult, a diluent, a buffer solution, water, or a physiological saline solution is added in order to collect immunoglobulin monomers that remains in the membrane or a pipe of an apparatus. In this case, it is not necessary for the immunoglobulin solution be filtered while maintaining the concentration of the immunoglobulin solution constant.

When purifying immunoglobulin monomers according to the present invention, it is preferable that 50% or more, more preferably 60% or more, and most preferably 70% or more of immunoglobulin monomers be subjected to constant-concentration filtration. For example, constant-volume filtration may be continuously performed after filtering 50% of immunoglobulin monomers. Alternatively, the supply of a diluent may be stopped when 20% of immunoglobulin monomers has been subjected to constant-volume filtration to recover the concentration before filtration, followed by constant-concentration filtration. When combining constant-concentration filtration, constant-volume filtration, and filtration without supplying a diluent, the order of filtration is not limited insofar as 50% of immunoglobulin monomers is subjected to constant-concentration filtration. This makes it possible to purify immunoglobulin monomers in high yield within a short time.

It has been considered that it is difficult to separate immunoglobulin monomers with precision when the immunoglobulin solution contains a biocomponent other than the immunoglobulin. Surprisingly, it was found that highly pure immunoglobulin monomers can be obtained by utilizing the separation method according to the present invention even if the immunoglobulin solution contains a biocomponent other than the immunoglobulin.

Examples of a biocomponent other than the immunoglobulin contained in the immunoglobulin solution according to the present invention include proteins, sugar chains, RNA, DNA, and the like. Specific examples of a biocomponent other than the immunoglobulin include blood coagulation factors (e.g., immunoglobulin aggregate, fibrinogen, and composite aggregate of immunoglobulin and protein A), cell adhesion factors, cell growth factors, enzymes, ribosomal proteins, hormones, aggregates thereof, and the like.

In the present invention, the lower limit of the molecular weight of the biocomponent other than immunoglobulin is 300,000 or more, preferably 400,000 or more, and more preferably 500,000 or more. The upper limit of the molecular weight of the biocomponent other than immunoglobulin is less than 1,000,000, preferably 900,000 or less, and more preferably 800,000 or less. If molecular weight of the biocomponent is within the above range, the biocomponent can be separated from immunoglobulin monomers with precision. If molecular weight of the biocomponent is less than 300,000, immunoglobulin monomers may not be separated with precision. Immunoglobulin monomers can be separated with greater precision as the molecular weight of the biocomponent increases. However, if the molecular weight of the biocomponent is too high, clogging of the membrane tends to occur.

Specifically, the immunoglobulin solution according to the present invention may contain immunoglobulin monomers, aggregates thereof (e.g., dimer and trimer), and a biocomponent having a molecular weight of 300,000 or more and less than 1,000,000. In this case, the present invention separates immunoglobulin monomers from the immunoglobulin solution that contains immunoglobulin monomers, aggregates thereof (e.g., dimer and trimer), and a biocomponent having a molecular weight of 300,000 or more and less than 1,000,000. Note that the present invention also separates immunoglobulin monomers from the immunoglobulin solution that does not contain the above biocomponent or contains only a small amount of the above biocomponent.

The immunoglobulin solution according to the present invention may contain viruses.

Examples of such viruses include parvovirus and poliovirus having a diameter of about 18 to 24 nm, Japanese encephalitis virus and hepatitis virus having a diameter of about 40 to 45 nm, HIV having a diameter of about 80 to 100 nm, and the like. It is most necessary to remove the parvovirus. Parvovirus is the smallest virus confirmed until today. When performing size fractionation using a membrane, it is considered that other large viruses can be removed if parvovirus can be removed.

Since viruses cause serious infectious diseases such as hepatitis, acquired immunodeficiency, Japanese encephalitis, and polio, it is preferable that the membrane have a virus log reduction value (LRV) of four or more. The LRV is calculated by the following formula (1).

$$LRV = \log[(No \times Vo)/(Nf \times Vf)] \quad (1)$$

LRV: virus log reduction value
No: viral infectivity in immunoglobulin stock solution before filtration ($TICD_{50}$/ml)
Nf: viral infectivity in immunoglobulin permeation solution ($TICD_{50}$/ml)
Vo: volume of immunoglobulin stock solution before filtration (ml)
Vf: volume of immunoglobulin permeation solution (ml)

Examples of the parvovirus used to evaluate the virus removal performance include a human parvovirus (B19), a porcine parvovirus, a canine parvovirus, a felin panleukopenia virus, a minute virus of mice, and the like. These viruses have a diameter of about 18 to 24 nm, and the virus removal performance can be evaluated using any of these viruses. It is preferable to use a porcine parvovirus or a canine parvovirus for which a convenient infectivity evaluation method has been established.

The term "ultrafiltration membrane" according to the present invention refers to a membrane that is used to separate immunoglobulin monomers from at least immunoglobulin dimers.

The ultrafiltration membrane is not limited insofar as the membrane can be produced so that it has the desired molecular weight cut-off and does not adsorb the immunoglobulin. Examples of the ultrafiltration membrane include a polysulfone polymer membrane, an aromatic ether polymer membrane, a fluorinated polymer membrane, an olefin polymer membrane, a cellulose membrane, a (meth)acrylic polymer membrane, a (meth)acrylonitrile polymer membrane, a vinyl alcohol polymer membrane, and the like. Among these, the polysulfone polymer membrane and the aromatic ether polymer membrane are preferable.

The polysulfone polymer used in the present invention is not particularly limited. An arbitrary polymer having a sulfone group in the molecule may be used. Examples of the polysulfone polymer include a polysulfone shown by the following formula (9), a polyethersulfone shown by the following formula (10), a polyarylsulfone shown by the following formula (11), and the like. In the formulas (9), (10), and (11), l, m, and n indicate the number of repeating units.

[Chem 9]

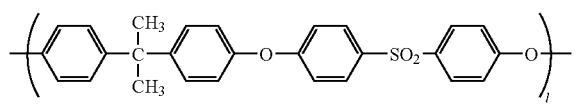

(9)

wherein l represents the number of repeating units.

[Chem 10]

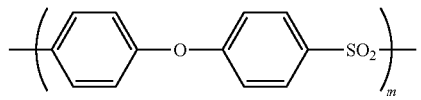

(10)

wherein m represents the number of repeating units.

[Chem 11]

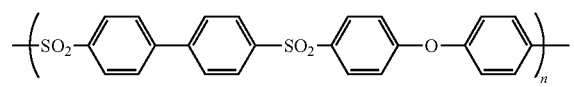

(11)

wherein n represents the number of repeating units.

These polymers may be used in combination. The polymer end and/or the main chain of the polysulfone polymer may be modified (e.g., esterified, etherified, or epoxidized). A chemical structure such as amino group, monoalkylamino group, dialkylamino group, carboxyl group, sulfonyl group, or sulfonic acid group may be introduced into the polysulfone polymer in order to ensure compatibility with the electrostatic characteristics of immunoglobulins.

The lower limit of the weight average molecular weight of the polysulfone polymer used in the present invention is 5,000 or more, preferably 10,000 or more, and more preferably 20,000 or more. The upper limit of the weight average molecular weight of the polysulfone polymer used in the present invention is 1,000,000 or less, preferably 500,000 or less, and more preferably 300,000 or less. If the weight average molecular weight of the polysulfone polymer is within the above range, the polysulfone polymer exhibits sufficient strength and membrane formability.

The type of hydrophilic polymer that confers hydrophilicity on the polysulfone polymer used in the present invention is not particularly limited. Examples of the hydrophilic polymer include polyvinylpyrrolidone, polyethylene glycol, polypropylene glycol, polyethylene oxide, a polyethylene glycol-polypropylene glycol block copolymer, polyvinyl alcohol, polyacrylamide, poly-N,N-dimethylacrylamide, poly-N-isopropylacrylamide, polyhydroxy acrylate, polyhydroxy methacrylate, carboxymethyl cellulose, starch, cornstarch, polychitosan, polychitin, and the like. Among these, it is preferable to use polyvinylpyrrolidone that exhibits excellent mutual solubility with the polysulfone polymer and increases the hydrophilicity of the entire membrane.

The lower limit of the weight average molecular weight of the hydrophilic polymer that provides the polysulfone polymer membrane used in the present invention with hydrophilicity is 1,000 or more, and preferably 5,000 or more. The upper limit of the weight average molecular weight of the hydrophilic polymer is 2,000,000 or less, and preferably 1,200,000 or less. For example, various grades of polyvinylpyrrolidone are commercially available from BASF. It is preferable to use polyvinylpyrrolidone having a weight average molecular weight of 9,000 (K17), 45,000 (K30), 450,000 (K60), 900,000 (K80), or 1,200,000 (K90). These grades of polyvinylpyrrolidone may be used either individually or in combination in order to achieve the desired application, characteristics, and structure. In the present invention, it is most preferable to use K90 alone.

The content of the hydrophilic polymer in the polysulfone polymer membrane used in the present invention is not particularly limited insofar as the immunoglobulin is not adsorbed on the membrane. For example, the lower limit of the content of the hydrophilic polymer is 0.1 wt % or more, preferably 0.3 wt % or more, and more preferably 0.5 wt % or more, and the upper limit of the content of the hydrophilic polymer is 10 wt % or less, preferably 8 wt % or less, and more preferably 5 wt % or less.

The molecular weight cut-off of the polysulfone polymer membrane used in the present invention is not particularly limited insofar as immunoglobulin monomers can be sufficiently separated from immunoglobulin dimers. The lower limit of the molecular weight cut-off of the polysulfone polymer membrane is 100,000 or more, preferably 150,000 or more, and more preferably 250,000 or more. The upper limit of the molecular weight cut-off of the polysulfone polymer membrane is 500,000 or less, preferably 450,000 or less, and more preferably 400,000 or less. If the molecular weight cut-off of the polysulfone polymer membrane is less than 100,000, the amount of immunoglobulins that passes through the membrane decreases. If the molecular weight cut-off of the polysulfone polymer membrane is more than 500,000, both immunoglobulin monomers and immunoglobulin dimers pass through the membrane (i.e., the fractionation performance decreases).

In the present invention, the molecular weight cut-off is calculated as a molecular weight that exhibits a blocking rate of 90% based on the correlation between molecular weight and blocking rate when performing a dead-end filtration using a protein such as albumin (66,000), γ-globulin (160,000), catalase (232,000), ferritin (440,000), thyroglobulin (669,000), polyethylene glycol (PEG), dextran, or the like.

A method of producing the polysulfone polymer membrane used in the present invention is not particularly limited. For example, a wet membrane-forming method may be used to produce the polysulfone polymer membrane. The wet membrane-forming method is a method that obtains a membrane by causing a membrane raw material solution in which a membrane material is dissolved in a good solvent to come in contact with a coagulation liquid (solvent) that is miscible with the good solvent in the membrane raw material solution, but is not mutually soluble with the membrane material so that concentration-induced phase separation occurs from the contact surface.

The membrane raw material solution used in the wet membrane-forming method to obtain the polymer membrane according to the present invention is not particularly limited insofar as a polysulfone polymer having the desired structure and performance can be produced. For example, the lower limit of the concentration of the polysulfone polymer in the membrane raw material solution is 1 wt % or more, preferably 2 wt % or more, and particularly preferably 3 wt % or more, based on the membrane raw material solution (=100 wt %). The upper limit of the concentration of the polysulfone polymer is 45 wt % or less, preferably 35 wt % or less, and particularly preferably 25 wt % or less. A solution in which the polysulfone polymer is homogeneously dissolved is preferably used. The lower limit of the concentration of the hydrophilic polymer is 0.1 wt % or more, and preferably 0.5 wt % or more. The upper limit of the concentration of the hydrophilic polymer is 20 wt % or less, and preferably 10 wt % or less. A solution in which the hydrophilic polymer is homogeneously dissolved is preferably used. The lower limit of the temperature of the membrane raw material solution is 0° C. or more, preferably 10° C. or more, and particularly preferably 25° C. or more. The upper limit of the temperature of the membrane raw material solution is preferably equal to or less than the boiling point of the good solvent contained in the membrane raw material solution. If the temperature of the membrane raw material solution is within the above range, the viscosity suitable for producing a membrane can be obtained.

The good solvent used in the wet membrane-forming method to obtain the polysulfone polymer membrane according to the present invention is not particularly limited insofar as the good solvent can be dissolved in 100 g of purified water at 20° C. in an amount of 10 g or more, preferably dissolves 5 wt % or more of the polysulfone polymer (membrane material), and is more preferably miscible with water. Specific examples of the good solvent include N-methyl-2-pyrrolidone, N,N-dimethylacetamide, dimethylsulfoxide, N,N-dimethylformamide, γ-butyrolactone, and the like. These good solvents may be used in combination.

The coagulation liquid used in the wet membrane-forming method to obtain the polysulfone polymer membrane according to the present invention is not particularly limited insofar as the coagulation liquid causes concentration-induced phase separation when coming in contact with the membrane raw material solution and forms a membrane from the contact surface. Examples of the coagulation liquid include purified water, a monohydric alcohol solvent, a polyol solvent, a mixture of two or more of these, and the like. Examples of the monohydric alcohol solvent include methanol, ethanol, propanol, and the like. Examples of the polyol solvent include ethylene glycol, diethylene glycol, triethylene glycol, tetraethylene glycol, glycerol, propylene glycol, 1,2-butanediol, 1,4-butanediol, and the like. A water-soluble polymer such as polyvinyl alcohol, polyethylene glycol, polypropylene glycol, polyethylene oxide, a polyethylene glycol-polypropylene glycol block copolymer, polyacrylamide, polyvinylpyrrolidone, polyhydroxy acrylate, polyhydroxy methacrylate, polyacrylic acid, polymethacrylic acid, polyitaconic acid, polyfumaric acid, polycitraconic acid, poly-p-styrene sulfonic acid, sodium poly-p-styrene sulfonate, N,N-dimethylacrylamide, carboxymethyl cellulose, starch, cornstarch, polychitosan, or polychitin may be added to the coagulation liquid. The filtration performance of the membrane can be improved by adding such a water-soluble polymer, although the improvement effect varies depending on the molecular weight and the amount of the water-soluble polymer added.

It is also possible to add a good solvent such as N-methyl-2-pyrrolidone, N,N-dimethylacetamide, dimethyl sulfoxide, N,N-dimethylformamide, or γ-butyrolactone to the coagulation liquid. When using a coagulation liquid that contains a good solvent and a non-solvent, the concentration of the good solvent in the coagulation liquid (=100 wt %) is preferably 90 wt % or more, although the composition varies depending on the composition of the membrane raw material solution, the contact temperature of the membrane raw material solution and the coagulation liquid, and the like. If the concentration of the good solvent is within the above range, concentration-induced phase separation sufficient to form a membrane occurs.

The membrane-forming temperature in the wet membrane-forming method used in the present invention refers to a temperature at which the membrane raw material solution is caused to come in contact with the coagulation liquid so that concentration-induced phase separation occurs. When producing the hollow fiber membrane according to the present invention, the membrane-forming temperature is determined by the temperature of a double spinneret. The lower limit of the membrane-forming temperature is 0° C. or more, preferably 10° C. or more, and particularly preferably 25° C. or more. The upper limit of the membrane-forming temperature is equal to or less than the boiling point of the membrane raw material solution or the coagulation liquid, preferably a temperature lower than the boiling point of the membrane raw material solution or the coagulation liquid by 5° C. or more, and particularly preferably a temperature lower than the boiling point of the membrane raw material solution or the coagulation liquid by 10° C. or more. The membrane-forming temperature is determined by the temperature of a double spinneret when producing a hollow fiber membrane. The membrane-forming temperature is determined by the temperature of the coagulation liquid when producing a flat membrane.

It is desirable to remove dissolved gas from the membrane raw material solution and the coagulation liquid (particularly a coagulation liquid that is passed through a fiber when producing a hollow fiber membrane (hereinafter referred to as "internal coagulation liquid")) used in the wet membrane-forming method to obtain the polysulfone polymer membrane according to the present invention after homogeneously dissolving each component. Defects of the membrane due to foaming of the dissolved gas can be significantly suppressed by removing the dissolved gas. In particular, removal of oxygen reduces an oxidation reaction of the material during membrane processing at a high temperature. This step may be omitted when gas is not dissolved in the membrane raw material solution, the coagulation liquid, and the internal coagulation liquid.

When producing a hollow fiber membrane using the wet membrane-forming method according to the present invention, in order to cause the membrane raw material solution discharged from a double spinneret to promptly coagulate due to the internal coagulation liquid, a bath (hereinafter referred to as "coagulation bath") may be provided directly under the spinneret, and the membrane raw material solution may be caused to come in contact with a coagulation liquid (hereinafter referred to as "external coagulation liquid") provided in the coagulation bath.

When producing a hollow fiber membrane using the wet membrane-forming method according to the present invention, the distance from the spinneret to the liquid surface of the external coagulation liquid (hereinafter referred to as "air gap distance") and the temperature and the humidity in the space from the spinneret to the liquid surface of the external coagulation liquid may be adjusted in order to arbitrarily control the cross-sectional structure of the hollow fiber membrane (e.g., uniform structure or non-uniform structure). For example, the lower limit of the air gap distance is 0.001 m or more, preferably 0.005 m or more, and particularly preferably 0.01 m or more, and the upper limit of the air gap distance is 2.0 m or less, preferably 1.5 m or less, and particularly preferably 1.2 m or less. The lower limit of the temperature in the space from the spinneret to the liquid surface of the external coagulation liquid is 10° C. or more, preferably 20° C. or more, and particularly preferably 25° C. or more. The lower limit of the humidity in the space from the spinneret to the liquid surface of the external coagulation liquid is 0% or more, preferably 10% or more, and particularly preferably 30% or more, and the upper limit of the humidity is 100% or less, although the humidity varies depending on the temperature.

The take-up speed when producing a hollow fiber membrane using the wet membrane-forming method according to the present invention is generally 300 m/h to 9,000 m/h, although the take-up speed varies depending on the production conditions, the shape of the spinneret, the composition of the spinning raw solution, the compositions of the internal coagulation liquid and the external coagulation liquid, the temperatures of the spinning raw solution and the coagulation liquids, and the like.

In the wet membrane-forming method according to the present invention, it is possible to accelerate removal of the solvent after coagulation with the coagulation liquid by immersing the membrane in a solvent removal liquid in order to increase the strength of the membrane. The solvent removal liquid is a liquid that can remove the solvent remaining after concentration-induced phase separation using the coagulation liquid. Any solvent may be used insofar as the membrane is not dissolved. Water, ethanol, or the like is generally used.

An undried ultrafiltration membrane obtained by the wet membrane-forming method is dried at a temperature at which breakage of the membrane does not occur during drying. For example, the lower limit of the drying temperature is 20° C. or more, and preferably 30° C. or more, and the upper limit of the drying temperature is 150° C. or less, and preferably 140° C. or less. The drying time is determined based on the drying temperature. The drying time is generally 0.01 to 48 hours.

The aromatic ether polymer membrane used in the present invention is not particularly limited. Examples of the aromatic ether polymer include an aromatic ether polymer shown by the following formula (12).

[Chem 12]

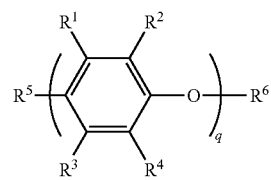

(12)

wherein $R^1$, $R^2$, $R^3$, $R^4$, $R^5$, and $R^6$ individually represent hydrogen, an organic functional group having 1 to 6 carbon atoms, or a non-protonic organic functional group having at most 6 carbon atoms and containing oxygen, nitrogen, or silicon. q represents the number of repeating units. The aromatic ether polymer may be a copolymer containing two or more different repeating units.

The phenolic hydroxyl group on the end of the aromatic ether polymer used in the present invention may optionally be modified by esterification, etherification, epoxidation, or the like in order to maintain the pH at which the aromatic ether polymer can be stably present in the immunoglobulin solution. A chemical structure such as an amino group, a monoalkylamino group, a dialkylamino group, a carboxyl group, a sulfonyl group, or a sulfonic acid group may optionally be introduced into the polymer end in order to ensure compatibility with the electrostatic characteristics of the immunoglobulin.

The aromatic ether polymer membrane used in the present invention is mainly formed of the aromatic ether polymer. The aromatic ether polymer membrane may contain other polymer substances and additives insofar as the characteristics of the aromatic ether polymer are not adversely affected. Such polymers may be used in combination. For example, the aromatic ether polymer membrane may contain polystyrene and a derivative thereof.

The lower limit of the weight average molecular weight of the aromatic ether polymer used in the present invention is 5,000 or more, preferably 10,000 or more, and particularly preferably 20,000 or more. The upper limit of the weight average molecular weight of the aromatic ether polymer is 1,000,000 or less, preferably 500,000 or less, and particularly preferably 300,000 or less. If the weight average molecular weight of the aromatic ether polymer is within the above range, the aromatic ether polymer exhibits sufficient strength and membrane formability.

In the present invention, it is preferable to use a hydrophilic polymer together with the aromatic ether polymer in order to control the pore size of the membrane and provide the membrane with hydrophilicity. Hydrophilization allows the immunoglobulin solution subjected to separation to advantageously come in contact with the ultrafiltration membrane formed of the aromatic ether polymer according to the present invention.

The hydrophilic polymer used in the present invention is not particularly limited insofar as the hydrophilic polymer can provide the membrane with hydrophilicity. In order to reduce electrical interaction with the immunoglobulin, the hydrophilic polymer is preferably a nonionic polymer that does not have a charged structure.

The molecular weight of the hydrophilic polymer used in the present invention is not particularly limited.

Examples of the hydrophilic polymer include hydrophilic polymer compounds such as polyethylene glycol, polypropylene glycol, polyethylene oxide, a polyethylene glycol-polypropylene glycol block copolymer, polyvinyl alcohol, polyacrylamide, poly-N,N-dimethylacrylamide, poly-N-isopropylacrylamide, polyvinylpyrrolidone, polyhydroxy acrylate, polyhydroxy methacrylate, carboxymethyl cellulose, starch, cornstarch, polychitosan, and polychitin. A surfactant, a block copolymer, or a graft copolymer that contains the above compound as a hydrophilic segment and a hydrophobic segment may also be used as the hydrophilic polymer. For example, a polystyrene-polyethylene glycol block copolymer or the like is preferably used.

Since the polystyrene-polyethylene glycol block copolymer contains highly hydrophilic polyethylene glycol as a hydrophilic segment, the polystyrene-polyethylene glycol block copolymer can be effectively used as the hydrophilic polymer according to the present invention. These hydrophilic polymers may be used in combination. Among these, polyethylene glycol, a block copolymer or a graft copolymer containing polyethylene glycol as a hydrophilic segment is particularly suitably used as the hydrophilic polymer. In particular, a polystyrene-polyethylene glycol block copolymer can be suitably used as the hydrophilic polymer that improves the hydrophilicity of the aromatic ether polymer membrane.

The molecular weight of the hydrophilic polymer used in the present invention is appropriately selected according to the production method and the production conditions. For example, when producing a membrane using the wet membrane-forming method utilizing a halogen-free water soluble organic solvent, the aromatic ether polymer having high solvent resistance exhibits very low solubility. Therefore, when blending the hydrophilic polymer with the membrane raw material solution, the molecular weight and the amount of the hydrophilic polymer must be appropriately selected in order to obtain a homogeneous membrane raw material solution. In order to use a sufficient amount of hydrophilic polymer, the number average molecular weight of the hydrophilic polymer is preferably 300 to 100,000, for example. The hydrophilic polymer having a molecular weight within the above range can be sufficiently dissolved in the good solvent used to produce a membrane. The lower limit of the molecular weight of the hydrophilic polymer is more preferably 400 or more, and particularly preferably 500 or more, and the upper limit of the molecular weight of the hydrophilic polymer is more preferably 70,000 or less, and particularly preferably 50,000 or less.

When the hydrophilic polymer used in the present invention is a compound that includes a hydrophobic segment and a hydrophilic segment, the number average molecular weight of the hydrophilic segment is preferably 300 to 100,000. The hydrophilic polymer of which the hydrophilic segment has a molecular weight within the above range can be sufficiently dissolved in the good solvent used to produce a membrane. The lower limit is more preferably 400 or more, and particularly preferably 500 or more, and the upper limit is more preferably 70,000 or less, and particularly preferably 50,000 or less.

The polystyrene-polyethylene glycol block copolymer used in the present invention is a block copolymer that includes segments derived from a polystyrene polymer and segments derived from a polyethylene glycol polymer.

As the polystyrene polymer that forms the segments derived from the polystyrene polymer included in the polystyrene-polyethylene glycol block copolymer used in the present invention, a polystyrene polymer having repeating units shown by the following formula (3) is preferable.

[Chem 13]

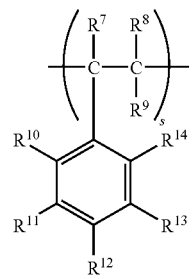

(13)

wherein $R^7$, $R^8$, $R^9$, $R^{10}$, $R^{11}$, $R^{12}$, $R^{13}$, and $R^{14}$ individually represent hydrogen, a halogen atom excluding fluorine, an organic functional group having 1 to 6 carbon atoms, or a functional group having at most 6 carbon atoms and containing oxygen, nitrogen, or silicon. s represents the number of repeating units. The polystyrene polymer may be a copolymer containing two or more different repeating units having the above structure.

In the polystyrene-polyethylene glycol block copolymer used in the present invention, the number average molecular weight of the segment derived from the polystyrene polymer is 300 to 1,000,000. If the number average molecular weight of the segment derived from the polystyrene polymer is within the above range, the polymer can be sufficiently dissolved in the good solvent used to produce a membrane. Moreover, elution of the polymer in an aqueous solution can be reduced. The lower limit of the molecular weight of the segment derived from the polystyrene polymer is more preferably 500 or more, and particularly preferably 700 or more, and the upper limit of the molecular weight of the segment derived from the polystyrene polymer is more preferably 500,000 or less, and particularly preferably 300,000 or less.

As the polyethylene glycol polymer that forms the segment derived from the polyethylene glycol polymer included in the polystyrene-polyethylene glycol block copolymer used in the present invention, a polyethylene glycol polymer having repeating units shown by the following formula (14) and/or repeating units shown by the following formula (15) is preferable.

[Chem 14]

(14)

[Chem 15]

(15)

wherein $R^{15}$ represents an organic functional group having 3 or more and less than 30 carbon atoms. $R^{15}$ may contain an ether group, an ester group, a hydroxyl group, a ketone group, or a carboxylic acid group insofar as hydrophilicity does not decrease to a large extent. t and u represent the number of repeating units.

In the polystyrene-polyethylene glycol block copolymer used in the present invention, the number average molecular weight of the segment derived from the polyethylene glycol polymer is 300 to 100,000, for example. If the number average molecular weight of the segment derived from the polyethylene glycol polymer is within the above range, the polymer can be sufficiently dissolved in the good solvent used to produce a membrane. Moreover, the resulting membrane exhibits sufficient hydrophilicity. The lower limit is more preferably 400 or more, and particularly preferably 500 or more, and the upper limit is more preferably 70,000 or less, and particularly preferably 50,000 or less.

Regarding the ratio of the segment derived from the polystyrene polymer to the segment derived from the polyethylene glycol polymer in the polystyrene-polyethylene glycol block copolymer used in the present invention, the content of the segment derived from the polystyrene polymer in the polystyrene-polyethylene glycol block copolymer is 10 to 99 wt %. The polystyrene-polyethylene glycol block copolymer having a segment ratio within the above range exhibits sufficient hydrophilicity and low elution property. The lower limit of the content of the segment derived from the polystyrene polymer is more preferably 20 wt % or more, and particularly preferably 30 wt % or more, and the upper limit of the content of the segment derived from the polystyrene polymer is more preferably 98 wt % or less, and particularly preferably 97 wt % or less.

The polystyrene-polyethylene glycol block copolymer used in the present invention may be a diblock copolymer that includes two segments, a triblock copolymer that includes three segments, or a multi-block copolymer that includes four or more segments. The polystyrene-polyethylene glycol block copolymer may be a mixture of these block copolymers. The number average molecular weight of each segment may be either the same or different.

The segments derived from the polystyrene polymer and the segments derived from the polyethylene glycol polymer included in the polystyrene-polyethylene glycol block copolymer used in the present invention must be directly and chemically bonded on polymer ends. If necessary, a low-molecular-weight compound and/or an organic functional group may be used as a spacer that connects the segments derived from the polystyrene polymer and the segments derived from the polyethylene glycol polymer. When the number average molecular weight of the low-molecular-weight compound and/or the organic functional group is 500 or less, the effects of the segment derived from the polystyrene polymer and the segment derived from the polyethylene glycol polymer are not adversely affected. For example, what may be used is a low-molecular-weight compound formed between polystyrene and polyethylene glycol when polymerizing styrene using a radical polymerization initiator having a reactive functional group, and then condensing polyethylene glycol with the resulting polystyrene.

The polystyrene-polyethylene glycol block copolymer used in the present invention may be produced using a radical polymerization initiator having a reactive functional group, for example. Specifically, polystyrene having an acid chloride group on the end is obtained by chemically converting a carboxylic acid group into an acid chloride group using an azo radical polymerization initiator having a carboxylic acid group, and then radically polymerizing styrene. The resulting polystyrene is condensed with polyethylene glycol to obtain a polystyrene-polyethylene glycol block copolymer (KOBUNSHI RONBUNSHU, 1976, Vol. 33, p. 131). A polystyrene-polyethylene glycol block copolymer can also be obtained by radically polymerizing styrene using a Macro azo initiator containing a polyethylene glycol unit. Alternatively, the polystyrene-polyethylene glycol block copolymer may be synthesized by utilizing living polymerization. Specifically, styrene is polymerized by living radical polymerization using a nitroxide compound to obtain a polymer to which the nitroxide compound is bonded on the polymer end. The polymer end is then converted into a hydroxyl group by hydrolysis, and a coupling reaction with polyethylene glycol is carried out to obtain a polystyrene-polyethylene glycol block copolymer (Polymer, 1998, Vol. 39, No. 4, p. 911).

The method for hydrophilizing the ultrafiltration membrane formed of the aromatic ether polymer using the hydrophilic polymer of the present invention includes; e.g., a blending method that mixes the hydrophilic polymer in advance when forming a membrane, a coating method that immerses the membrane in a solution containing the hydrophilic polymer, and dries the membrane to allow the hydrophilic polymer to remain on the surface of the membrane, a method that grafts a hydrophilic acrylic monomer, methacrylic monomer, acrylamide monomer, or the like to the surface of the membrane. These methods may be used in combination. It is preferable to use the blending method or the coating method that does not chemically modify the aromatic ether polymer.

From the viewpoint of production, it is particularly preferable to use the blending method that can hydrophilize the membrane by a single step.

The molecular weight cut-off of the aromatic ether polymer membrane used in the present invention is not particularly limited insofar as immunoglobulin monomers can be sufficiently separated from immunoglobulin dimers. The lower limit of the molecular weight cut-off of the aromatic ether polymer membrane is 100,000 or more, preferably 150,000 or more, and more preferably 250,000 or more. The upper limit of the molecular weight cut-off of the aromatic ether polymer membrane is 500,000 or less, preferably 450,000 or less, and more preferably 400,000 or less. If the molecular weight cut-off of the aromatic ether polymer membrane is less than 100,000, the amount of immunoglobulin that passes through the membrane decreases. If the molecular weight cut-off of the aromatic ether polymer membrane is more than 500,000, immunoglobulin monomers and immunoglobulin dimers pass through the membrane (i.e., the fractionation performance decreases).

In the present invention, the molecular weight cut-off is calculated as a molecular weight that provides a blocking rate of 90% based on the correlation between molecular weight and blocking rate when performing dead-end filtration using a protein such as albumin (66,000), γ-globulin (160,000), catalase (232,000), ferritin (440,000), thyroglobulin (669,000), PEG, dextran, or the like.

A method of producing the aromatic ether polymer membrane used in the present invention is not particularly limited. For example, a wet membrane-forming method may be used to produce the aromatic ether polymer membrane. The wet membrane-forming method is a method that obtains a membrane by causing a membrane raw material solution in which a membrane material is dissolved in a good solvent to come in contact with a coagulation liquid (solvent) that is miscible with the good solvent in the membrane raw material solution, but is not mutually soluble with the membrane material so that concentration-induced phase separation occurs from the contact surface.

As the good solvent used in the wet membrane-forming method used to produce the aromatic ether polymer used in the present invention, any solvent may be used insofar as the solvent can stably dissolve the aromatic ether polymer (membrane material) in an amount of 5 wt % or more under the membrane-forming conditions. It is preferable to use a halogen-free water-soluble organic solvent from the viewpoint of the environment and cost. The term "water-soluble organic solvent" used herein refers to a solvent that can be dissolved in 100 g of purified water (20° C.) in an amount of 10 g or more, and is preferably miscible with water. Specific examples of the water-soluble organic solvent include N-methyl-2-pyrrolidone, N,N-dimethylacetamide, dimethylsulfoxide, N,N-dimethylformamide, γ-butyrolactone, and the like. These water-soluble organic solvents may be used in combination.

As the membrane raw material solution used in the wet membrane-forming method used to produce the aromatic ether polymer membrane used in the present invention, a solution in which the hydrophilic polymer is homogeneously dissolved in the good solvent in an amount of 0.1 wt % or more, preferably 0.5 wt % or more, and particularly preferably 1 wt % or more, but 45 wt % or less, preferably 35 wt % or less, and particularly preferably 25 wt % or less, is preferably used.

The aromatic ether polymer is used in an amount of 1 wt % or more, preferably 2 wt % or more, and particularly preferably 3 wt % or more, based on the membrane raw material solution (=100 wt %). The aromatic ether polymer is used in an amount of 45 wt % or less, preferably 35 wt % or less, and particularly preferably 25 wt % or less, based on the membrane raw material solution (=100 wt %). A solution in which the aromatic ether polymer is homogeneously dissolved is preferably used.

The lower limit of the temperature of the membrane raw material solution is 25° C. or more, preferably 65° C. or more, and particularly preferably 80° C. or more, and the upper limit of the temperature of the membrane raw material solution is equal to or less than the boiling point of the good solvent. The solubility of the aromatic ether polymer can be increased under the said temperature condition. Moreover, the membrane raw material solution has a viscosity suitable for producing a membrane.

The coagulation liquid used in the wet membrane-forming method used to produce the hydrophilic aromatic ether polymer membrane according to the present invention refers to a substance that causes concentration-induced phase separation when coming in contact with the membrane raw material solution so that a membrane is formed from the contact surface. As the coagulation liquid, purified water, a monohydric alcohol solvent, a polyol solvent shown by the following formula (16), a mixture thereof, or the like is preferably used.

[Chem 16]

$$\text{HO—R}^{16}\text{—OH} \quad (16)$$

wherein $R^{16}$ represents an organic functional group having 1 to 20 carbon atoms or a structure containing one or more oxygen atoms and 1 to 20 carbon atoms, and may contain at least one of a hydroxyl group, an ether bond, an ester group, a ketone group, and a carboxylic acid group.

Examples of the polyol solvent shown by the formula (16) include ethylene glycol, diethylene glycol, triethylene glycol, tetraethylene glycol, glycerol, propylene glycol, 1,2-butanediol, 1,4-butanediol, and the like.

The water permeability of the aromatic ether polymer membrane can be controlled by adjusting the viscosity of the coagulation liquid used in the wet membrane-forming method used to produce the aromatic ether polymer membrane. It was found that the coagulation liquid gradually permeates the membrane raw material solution as a result of increasing the viscosity of the coagulation liquid so that water permeability of the resulting membrane is improved. The viscosity (20° C.) of the coagulation liquid is preferably 3 cp or more in order to obtain high water permeability. The viscosity (20° C.) of the coagulation liquid is more preferably 5 cp or more. A water-soluble polymer such as polyvinyl alcohol, polyethylene glycol, polypropylene glycol, polyethylene oxide, a polyethylene glycol-polypropylene glycol block copolymer, polyacrylamide, polyvinylpyrrolidone, polyhydroxy acrylate, polyhydroxy methacrylate, polyacrylic acid, polymethacrylic acid, polyitaconic acid, polyfumaric acid, polycitraconic acid, poly-p-styrene sulfonic acid, sodium poly-p-styrene sulfonate, N,N-dimethylacrylamide, carboxymethyl cellulose, starch, cornstarch, polychitosan, or polychitin may be added to the coagulation liquid to increase the viscosity of the coagulation liquid. It is also preferable to add a highly viscous solvent having a viscosity (20° C.) of 5 cp or more (e.g., the polyol solvent) to the coagulation liquid.

The viscosity of the coagulation liquid used in the present invention refers to a value measured using a glass capillary viscometer. Specifically, the coagulation liquid is placed in a glass capillary viscometer in a thermostat water bath (20° C.), and allowed to stand for 30 minutes or more until the temperature of the coagulation liquid becomes constant. The kinematic viscosity of the coagulation liquid is then measured. The viscosity of the coagulation liquid is calculated from the kinematic viscosity using the following formula (2). An Ubbelohde viscometer (manufactured by Shibata Scientific Technology, Ltd.) or the like may be used as the glass capillary viscometer.

$$v=\eta/\rho \quad (2)$$

where, v indicates the kinematic viscosity (mm$^2$/s), $\eta$ indicates the viscosity (cp), and $\rho$ indicates the density (g/cm$^3$).

A good solvent such as N-methyl-2-pyrrolidone, N,N-dimethylacetamide, dimethylsulfoxide, N,N-dimethylformamide, or γ-butyrolactone may be added to the coagulation liquid used in the wet membrane-forming method used to produce the aromatic ether polymer membrane according to the present invention. When using a coagulation liquid that contains a good solvent and a non-solvent, the content of the good solvent in the coagulation liquid (100 wt %) is preferably 0 wt % or more and 90 wt % or less, although the composition of the coagulation liquid varies depending on the composition of the membrane raw material solution, the contact temperature of the membrane raw material solution and the coagulation liquid, and the like. If the content of the good solvent is within the above range, concentration-induced phase separation sufficient to form a membrane occurs.

The membrane-forming temperature in the wet membrane-forming method used in the present invention refers to a temperature at which the membrane raw material solution is caused to come in contact with the coagulation liquid so that concentration-induced phase separation occurs. When producing the hollow fiber membrane according to the present invention, the membrane-forming temperature is determined by the temperature of a double spinneret. The membrane-forming temperature is determined by the temperature of the coagulation liquid when producing a flat membrane. The lower limit of the membrane-forming temperature is 25° C. or more, preferably 80° C. or more, and particularly preferably 90° C. or more. The upper limit of the membrane-forming temperature is equal to or less than the boiling point of the membrane raw material solution or the coagulation liquid, preferably a temperature lower than the boiling point of the membrane raw material solution or the coagulation liquid by 5° C. or more, and particularly preferably a temperature lower than the boiling point of the membrane raw material solution or the coagulation liquid by 10° C. or more. A membrane having a high strength can be obtained when causing the membrane raw material solution to come in contact with the coagulation liquid at a membrane-forming temperature that is equal to or higher than 80° C. and is lower than the boiling point of the membrane raw material solution or the coagulation liquid by 10° C. or more.

It is desirable to remove dissolved gas from the membrane raw material solution and the coagulation liquid (particularly a coagulation liquid that is passed through a fiber when producing a hollow fiber membrane (hereinafter referred to as "internal coagulation liquid")) used in the wet membrane-forming method to obtain the aromatic ether polymer membrane according to the present invention after homogeneously dissolving each component. Defects of the membrane due to foaming of the dissolved gas can be significantly suppressed by removing the dissolved gas. In particular, removal of oxygen reduces an oxidation reaction of a material during membrane processing at a high temperature.

When producing a hollow fiber membrane using the wet membrane-forming method according to the present invention, in order to cause the membrane raw material solution discharged from a double spinneret to promptly coagulate due to the internal coagulation liquid, a bath (hereinafter referred to as "coagulation bath") may be provided directly under the spinneret, and the membrane raw material solution may be caused to come in contact with a coagulation liquid (hereinafter referred to as "external coagulation liquid") provided in the coagulation bath.

When producing a hollow fiber membrane using the wet membrane-forming method according to the present invention, the distance from the spinneret to the liquid surface of the external coagulation liquid (hereinafter referred to as "air gap distance") and the temperature and the humidity in the space from the spinneret to the liquid surface of the external coagulation liquid may be adjusted in order to arbitrarily control the cross-sectional structure of the hollow fiber membrane (e.g., uniform structure or non-uniform structure).

When producing a hollow fiber membrane using the wet membrane-forming method according to the present invention, the lower limit of the air gap distance is 0.01 m or more, preferably 0.05 m or more, and particularly preferably 0.1 m or more, and the upper limit of the air gap distance is 2.0 m or less, preferably 1.5 m or less, and particularly preferably 1.2 m or less. The lower limit of the temperature in the space from the spinneret to the liquid surface of the internal coagulation liquid is 20° C. or more, preferably 50° C. or more, and particularly preferably 80° C. or more. The lower limit of the humidity in the space from the spinneret to the liquid surface of the external coagulation liquid is 0% or more, preferably 25% or more, and particularly preferably 50% or more, and the upper limit of the humidity is 100% or less, although the humidity varies depending on the temperature.

The take-up speed when producing a hollow fiber membrane using the wet membrane-forming method according to the present invention is generally 600 m/h to 9,000 m/h, although the take-up speed varies depending on the production conditions, the shape of the spinneret, the composition of the spinning raw solution, the compositions of the internal coagulation liquid and the external coagulation liquid, the temperatures of the raw solution and the coagulation liquids, and the like.

An aromatic ether polymer membrane having sufficient degrees strength and of elongation can be obtained using the wet membrane-forming method according to the present invention. Moreover, a porous membrane having a graded structure, which is difficult to obtain when using a melt membrane-forming method that utilizes temperature-induced phase separation, can be easily produced using the wet membrane-forming method according to the present invention by utilizing concentration-induced phase separation so that the resulting membrane can be provided with high water permeability.

In the wet membrane-forming method according to the present invention, it is possible to accelerate removal of the solvent after coagulation with the coagulation liquid by immersing the membrane in a solvent removal liquid in order to increase the strength of the membrane. The solvent removal liquid is a liquid that can remove the solvent remaining after concentration-induced phase separation using the coagulation liquid. Any solvent may be used insofar as the membrane is not dissolved. Water, ethanol, or the like is generally used as the solvent removal liquid.

The membrane-forming temperature in the wet membrane-forming method used in the present invention refers to a temperature at which the membrane raw material solution is caused to come in contact with the coagulation liquid so that concentration-induced phase separation occurs. Specifically, the membrane-forming temperature is determined by the temperature of the membrane raw material solution, the temperature of the coagulation liquid, the temperature of the double spinneret when producing a hollow fiber membrane, the temperature of a metal plate that supports membrane formation when producing a flat membrane, and the like. The lower limit of the membrane-forming temperature is 20° C. or more, preferably 25° C. or more, and particularly preferably 30° C. or more. The upper limit of the membrane-forming temperature is equal to or less than the boiling point of the membrane raw material solution or the coagulation liquid, preferably a temperature lower than the boiling point of the membrane raw material solution or the coagulation liquid by 5° C. or more, and particularly preferably a temperature lower than the boiling point of the membrane raw material solution or the coagulation liquid by 10° C. or more. A membrane having a high strength can be obtained when causing the membrane raw material solution to come in contact with the coagulation liquid at a membrane-forming temperature that is equal to or higher than 80° C. and is lower than the boiling point of the membrane raw material solution or the coagulation liquid by 10° C. or more.

An undried aromatic ether polymer membrane obtained by the wet membrane-forming method is dried at a temperature at which breakage of the membrane does not occur (e.g., a temperature between 20° C. and a temperature equal to or lower than the melting point of the aromatic ether polymer). The drying temperature is preferably 50 to 150° C., more preferably 60 to 140° C., and particularly preferably 70 to 130° C. The drying time is determined based on the drying temperature. The drying time is generally 0.01 to 48 hours.

The (meth)acrylic polymer membrane used in the present invention is not particularly limited. Examples of the (meth) acrylic polymer include a (meth)acrylic polymer shown by the following formula (17).

[Chem 17]

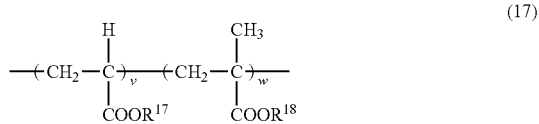

(17)

wherein $R^{17}$ and $R^{18}$ represent an alkyl group or an aralkyl group having 1 to 14 carbon atoms, provided that a hydrogen atom of the alkyl group or a hydrogen atom of the aralkyl group may be replaced by an alkoxy group having 1 to 10 carbon atoms. v and w represent the number of repeating units.

Specifically, poly(meth)acrylic acid, a poly(meth)acrylate, or the like may be used. It is preferable to use polyacrylic acid, polymethacrylic acid, polymethyl acrylate, polyethyl acrylate, polymethyl methacrylate, polyethyl methacrylate, or a copolymer thereof. The polymer ends and/or the main chain of the (meth)acrylic polymer may be modified (e.g., esterified, etherified, or epoxidized), if necessary. A chemical structure such as an amino group, a monoalkylamino group, a dialkylamino group, a carboxyl group, a sulfonyl group, or a sulfonic acid group may be introduced into the (meth)acrylic polymer in order to ensure compatibility with the electrostatic characteristics of the immunoglobulin.

The (meth)acrylic polymer membrane used in the present invention is mainly formed of a poly(meth)acrylate. The (meth)acrylic polymer membrane may contain other polymer substances and additives insofar as the characteristics of the poly(meth)acrylate are not adversely affected. These polymers may be used in combination.

The lower limit of the weight average molecular weight of the (meth)acrylic polymer used in the present invention is 5,000 or more, preferably 10,000 or more, and particularly preferably 20,000 or more. The upper limit of the weight average molecular weight of the (meth)acrylic polymer is 1,000,000 or less, preferably 500,000 or less, and particularly preferably 300,000 or less. If the weight average molecular weight of the (meth)acrylic polymer is within the above range, the (meth)acrylic polymer exhibits sufficient strength and membrane formability.

In the present invention, it is preferable to use a hydrophilic polymer together with the (meth)acrylic polymer in order to control the pore size of the membrane and provide the membrane with hydrophilicity. Examples of the hydrophilic polymer include polyvinylpyrrolidone, polyethylene glycol, polypropylene glycol, polyethylene oxide, a polyethylene glycol-polypropylene glycol block copolymer, polyvinyl alcohol, poly(meth)acrylamide, poly-N,N-dimethyl(meth) acrylamide, poly-N-isopropyl(meth)acrylamide, polyhydroxy acrylate, polyhydroxy methacrylate, carboxymethyl cellulose, starch, cornstarch, polychitosan, polychitin, and the like. Among these, it is preferable to use polyvinylpyrrolidone that exhibits excellent mutual solubility with the (meth)acrylic polymer and increases the hydrophilicity of the entire membrane.

The lower limit of the weight average molecular weight of the hydrophilic polymer that confers hydrophilicity on the (meth)acrylic polymer membrane used in the present invention is 1,000 or more, and preferably 5,000 or more. The upper limit of the weight average molecular weight of the hydrophilic polymer is 2,000,000 or less, preferably 1,000,000 or less, and particularly preferably 500,000 or less. For example, various grades of polyvinylpyrrolidone are commercially available from BASF. It is preferable to use polyvinylpyrrolidone having a weight average molecular weight of 9,000 (K17), 45,000 (K30), 450,000 (K60), 900,000 (K80), or 1,200,000 (K90). These grades of polyvinylpyrrolidone may be used either individually or in combination according to the desired application, characteristics, and structure.

The molecular weight cut-off of the (meth)acrylic polymer membrane used in the present invention is not particularly limited insofar as immunoglobulin monomers can be sufficiently separated from immunoglobulin dimers. The lower limit is 100,000 or more, preferably 150,000 or more, and more preferably 250,000 or more. The upper limit is 500,000 or less, preferably 450,000 or less, and more preferably 400,000 or less. If the molecular weight cut-off is less than 100,000, the amount of immunoglobulin that passes through the membrane decreases. If the molecular weight cut-off is more than 500,000, immunoglobulin monomers and immunoglobulin dimers pass through the membrane (i.e., the fractionation performance decreases).

In the present invention, the molecular weight cut-off is calculated as a molecular weight that gives a blocking rate of 90% based on the correlation between molecular weight and blocking rate when performing dead-end filtration using a protein such as albumin (66,000), γ-globulin (160,000), catalase (232,000), ferritin (440,000), thyroglobulin (669,000), PEG, dextran, or the like.

A method of producing the (meth)acrylic polymer membrane used in the present invention is not particularly limited. For example, a wet membrane-forming method may be used to produce the (meth)acrylic polymer membrane. The wet membrane-forming method is a method that obtains a membrane by causing a membrane raw material solution in which a membrane material is dissolved in a good solvent to come in contact with a coagulation liquid (solvent) that is miscible with the good solvent in the membrane raw material solution, but is not mutually soluble with the membrane material so that concentration-induced phase separation occurs from the contact surface.

The good solvent used in the wet membrane-forming method to obtain the (meth)acrylic polymer membrane according to the present invention is not particularly limited insofar as the good solvent is miscible with water. It is preferable to use a good solvent that can be dissolved in 100 g of purified water (20° C.) in an amount of 10 g or more, and dissolves 5 wt % or more of the (meth)acrylic polymer (membrane material). Specific examples of the good solvent include N-methyl-2-pyrrolidone, N,N-dimethylacetamide, dimethylsulfoxide, N,N-dimethylformamide, acetone, γ-butyrolactone, and the like. It is preferable to use dimethyl sulfoxide, N,N-dimethylacetamide, or N-methyl-2-pyrrolidone from the viewpoint of safety and non-toxicity. These solvents may be used either individually or in combination.

The membrane raw material solution used in the wet membrane-forming method to obtain the (meth)acrylic polymer membrane according to the present invention is not particularly limited insofar as a (meth)acrylic polymer membrane having the desired structure and performance can be produced. Membrane formability is improved as the concentration of the (meth)acrylic polymer in the membrane raw material solution increases. On the other hand, the porosity of the membrane decreases as the concentration of the (meth) acrylic polymer increases so that water permeability tends to decrease. The (meth)acrylic polymer is used in an amount of 2 wt % or more, preferably 5 wt % or more, and particularly preferably 10 wt % or more, based on the membrane raw material solution (=100 wt %), although the concentration of the (meth)acrylic polymer varies depending on the molecular weight of the (meth)acrylic polymer. The upper limit of the concentration of the (meth)acrylic polymer is 50 wt % or less, preferably 40 wt % or less, and particularly preferably 30 wt % or less. A solution in which the (meth)acrylic polymer is homogeneously dissolved is preferably used.

The lower limit of the temperature of the membrane raw material solution is 0° C. or more, preferably 10° C. or more, and particularly preferably 25° C. or more. The upper limit of the temperature of the membrane raw material solution is preferably equal to or less than the boiling point of the good solvent contained in the membrane raw material solution. If the temperature of the membrane raw material solution is within the above range, a viscosity suitable for producing a membrane can be obtained.

If necessary, additives such as an antioxidant, a nucleating agent, an antistatic agent, a flame retardant, a lubricant, and a UV absorber may be added to the membrane raw material solution used in the present invention insofar as the performance of the resulting membrane is not adversely affected.

The hydrophilic polymer used in the wet membrane-forming method used to obtain the (meth)acrylic polymer membrane according to the present invention mainly promotes formation of a porous structure of an outer porous support layer, and increases the viscosity of the membrane raw material solution. The molecular weight and the amount of the hydrophilic polymer added to the membrane raw material solution may be appropriately adjusted so that a membrane is stably formed. If the viscosity of the membrane raw material solution is low, breakage of the membrane may occur during production (i.e., the membrane may not be stably formed). If the viscosity of the membrane raw material solution is too high, the outer porous support layer may not be sufficiently formed (grown) so that the porosity of the outer-layer porous structure may become insufficient. As a result, a membrane having high permeability may not be obtained. Moreover, the membrane raw material solution discharged from the spinneret is feared to undergo a melt fracture phenomenon due to an increase in the viscosity of the membrane raw material solution.

In the wet membrane-forming method used to obtain the (meth)acrylic polymer membrane according to the present invention, the upper limit value of the concentration of the hydrophilic polymer in the membrane raw material solution is appropriately optimized based on the type and the molecular weight of the hydrophilic polymer. The upper limit value of the concentration of the hydrophilic polymer is normally 40 wt % or less, and preferably 30 wt % or less.

The coagulation liquid used in the wet membrane-forming method to obtain the (meth)acrylic polymer membrane according to the present invention is not particularly limited insofar as the coagulation liquid causes concentration-induced phase separation when coming in contact with the membrane raw material solution and forms a membrane from the contact surface. For example, purified water, a monohydric alcohol solvent, a polyol solvent, or a mixture thereof is preferably used as the coagulation liquid. Examples of the monohydric alcohol solvent include methanol, ethanol, propanol, and the like. Examples of the polyol solvent include ethylene glycol, diethylene glycol, triethylene glycol, tetraethylene glycol, glycerol, propylene glycol, 1,2-butanediol, 1,4-butanediol, and the like. A water-soluble polymer such as polyvinyl alcohol, polyethylene glycol, polypropylene glycol, polyethylene oxide, a polyethylene glycol-polypropylene glycol block copolymer, poly(meth)acrylamide, polyvinylpyrrolidone, polyhydroxy acrylate, polyhydroxy methacrylate, poly(meth)acrylic acid, polymethacrylic acid, polyitaconic acid, polyfumaric acid, polycitraconic acid, poly-p-styrene sulfonic acid, sodium poly-p-styrene sulfonate, N,N-dimethyl(meth)acrylamide, carboxymethylcellulose, starch, cornstarch, polychitosan, or polychitin may be added to the coagulation liquid. The filtration performance of the membrane can be improved by adding such a water-soluble polymer, although the improvement effect varies depending on the molecular weight and the amount of the water-soluble polymer. It is also possible to add a good solvent such as N-methyl-2-pyrrolidone, N,N-dimethylacetamide, dimethyl sulfoxide, N,N-dimethylformamide, or γ-butyrolactone to the coagulation liquid. When using a coagulation liquid that contains a good solvent and a nonsolvent, the concentration of the good solvent in the coagulation liquid (=100 wt %) is preferably 90 wt % or more, although the composition varies depending on the composition of the membrane raw material solution, the contact temperature of the membrane raw material solution and the coagulation liquid, and the like. If the concentration of the good solvent is within the above range, concentration-induced phase separation sufficient to form a membrane occurs.

The coagulation liquid that is passed through a fiber when producing a hollow fiber membrane (hereinafter referred to as "internal coagulation liquid") using the wet membrane-forming method used to obtain the (meth)acrylic polymer membrane according to the present invention may be a solution similar to the external coagulation liquid, or the (meth)acrylic polymer membrane may be produced using a dry-and-wet membrane-forming method that introduces a gas such as air, nitrogen, or ammonia gas into a fiber.

The membrane-forming temperature in the wet membrane-forming method used to produce the (meth)acrylic polymer membrane according to the present invention refers to a temperature at which the membrane raw material solution is caused to come in contact with the coagulation liquid so that concentration-induced phase separation occurs. The lower limit of the membrane-forming temperature is 0° C. or more, preferably 10° C. or more, and particularly preferably 25° C. or more. The upper limit of the membrane-forming temperature is equal to or less than the boiling point of the membrane raw material solution or the coagulation liquid, preferably a temperature lower than the boiling point of the membrane raw material solution or the coagulation liquid by 5° C. or more, and particularly preferably a temperature lower than the boiling point of the membrane raw material solution or the coagulation liquid by 10° C. or more. The membrane-forming temperature is determined by the temperature of a double spinneret when producing a hollow fiber membrane. The membrane-forming temperature is determined by the temperature of the coagulation liquid when producing a flat membrane.

It is desirable to remove dissolved gas from the membrane raw material solution and the coagulation liquid (particularly a coagulation liquid that is passed through a fiber when producing a hollow fiber membrane (hereinafter referred to as "internal coagulation liquid")) used in the wet membrane-forming method to obtain the (meth)acrylic polymer membrane according to the present invention after homogeneously dissolving each component. Defects of the membrane due to foaming of the dissolved gas can be significantly suppressed by removing the dissolved gas. In particular, removal of oxygen reduces an oxidation reaction of a material during membrane processing at a high temperature. This step may be omitted when gas is not dissolved in the membrane raw material solution, the coagulation liquid, and the internal coagulation liquid. This step is omitted when using a gas such as air, nitrogen, or ammonia gas as the coagulation agent (i.e., dry-and-wet membrane-forming method).

When producing a hollow fiber membrane using the wet membrane-forming method used to produce the (meth) acrylic polymer membrane according to the present invention, in order to allow the membrane raw material solution discharged from a double spinneret to promptly coagulate due to the internal coagulation liquid, a bath (hereinafter referred to as "coagulation bath") may be provided directly under the spinneret, and the membrane raw material solution may be caused to come in contact with a coagulation liquid (hereinafter referred to as "external coagulation liquid") provided in the coagulation bath.

When producing a hollow fiber membrane using the wet membrane-forming method used to produce the (meth) acrylic polymer membrane according to the present invention, the distance from the spinneret to the liquid surface of the external coagulation liquid (hereinafter referred to as "air gap distance") and the temperature and the humidity in the space from the spinneret to the liquid surface of the external coagulation liquid may be adjusted in order to arbitrarily control the cross-sectional structure of the hollow fiber membrane (e.g., uniform structure or non-uniform structure). For example, the lower limit of the air gap distance is 0.001 m or more, preferably 0.005 m or more, and particularly preferably 0.01 m or more, and the upper limit of the air gap distance is 2.0 m or less, preferably 1.5 m or less, and particularly preferably 1.2 m or less. The lower limit of the temperature in the space from the spinneret to the liquid surface of the external coagulation liquid is 10° C. or more, preferably 20° C. or more, and particularly preferably 25° C. or more. The lower limit of the humidity in the space from the spinneret to the liquid surface of the external coagulation liquid is 0% or more, preferably 10% or more, and particularly preferably 30% or more, and the upper limit of the humidity is 100% or less, although the humidity varies depending on the temperature.

The take-up speed when producing a hollow fiber membrane using the wet membrane-forming method used to produce the (meth)acrylic polymer membrane according to the present invention is generally 300 m/h to 9,000 m/h, although the take-up speed varies depending on the production conditions, the shape of the spinneret, the composition of the spinning raw solution, the compositions of the internal coagulation liquid and the external coagulation liquid, the temperatures of the raw solution and the coagulation liquids, and the like.

In the wet membrane-forming method used to produce the (meth)acrylic polymer membrane according to the present invention, it is possible to accelerate removal of the solvent after coagulation with the coagulation liquid by immersing the membrane in a solvent removal liquid in order to increase the strength of the membrane. The solvent removal liquid is a liquid that can remove the solvent remaining after concentration-induced phase separation using the coagulation liquid. Any solvent may be used insofar as the membrane is not dissolved. Water, ethanol, or the like is generally used as the solvent removal liquid.

An undried (meth)acrylic polymer membrane obtained by the wet membrane-forming method according to the present invention is dried at a temperature at which breakage of the membrane does not occur (e.g., a temperature between 20° C. and a temperature equal to or lower than the melting point of the (meth)acrylic polymer). The lower limit of the drying temperature is 30° C. or more, and preferably 40° C. or more. The upper limit of the drying temperature is 80° C. or less, and preferably 70° C. or less. The drying time is determined based on the drying temperature. The drying time is generally 0.01 to 48 hours.

The (meth)acrylonitrile polymer membrane used in the present invention is not particularly limited. Examples of the (meth)acrylonitrile polymer include a (meth)acrylonitrile polymer shown by the following formula (18).

[Chem 18]

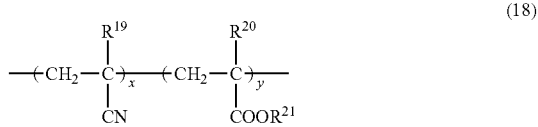

(18)

wherein $R^{19}$ and $R^{20}$ represent hydrogen or a methyl group. $R^{21}$ represents an alkyl group or an aralkyl group having 1 to 14 carbon atoms, provided that a hydrogen atom of the alkyl group or a hydrogen atom of the aralkyl group may be replaced by an alkoxy group having 1 to 10 carbon atoms. x and y represent the number of repeating units.

Specifically, poly(meth)acrylonitrile, a poly(meth)acrylonitrile acid ester, or the like may be used. It is preferable to use polyacrylonitrile or polymethacrylonitrile.

Regarding the monomer composition of the (meth)acrylonitrile polymer according to the present invention, the content of (meth)acrylonitrile is at least 50 wt % or more, and preferably 60 wt % or more, and the content of one or more vinyl compounds copolymerizable with (meth)acrylonitrile is 50 wt % or less, and preferably 40 wt % or less. The vinyl compound is not particularly limited insofar as the vinyl compound is copolymerizable with (meth)acrylonitrile. Examples of a preferable copolymerization component include (meth)acrylic acid, methyl (meth)acrylate, ethyl (meth)acrylate, itaconic acid, vinyl acetate, sodium (meth)acrylsulfonate, sodium p-styrenesulfonate, hydroxyethyl methacrylate, ethyl methacrylate triethylammonium chloride, ethyl methacrylate trimethylammonium chloride, vinylpyrrolidone, and the like. For example, the copolymer may be an acrylonitrile-methyl acrylate-PVP copolymer.

The polymer ends and/or the main chain of the (meth)acrylonitrile polymer may be modified (e.g., esterified, etherified, or epoxidized), if necessary. A chemical structure such as an amino group, a monoalkylamino group, a dialkylamino group, a carboxyl group, a sulfonyl group, or a sulfonic acid group may be introduced into the (meth)acrylonitrile polymer in order to ensure compatibility with the electrostatic characteristics of the immunoglobulin.

The (meth)acrylonitrile polymer membrane used in the present invention is mainly formed of the (meth)acrylonitrile polymer. The (meth)acrylonitrile polymer membrane may contain other polymer substances and additives insofar as the characteristics of the (meth)acrylonitrile polymer are not adversely affected. These polymers may be used in combination.

The lower limit of the weight average molecular weight of the (meth)acrylonitrile polymer used in the present invention is 5,000 or more, preferably 10,000 or more, and particularly preferably 20,000 or more. The upper limit of the weight average molecular weight of the (meth)acrylonitrile polymer is 1,000,000 or less, preferably 500,000 or less, and particularly preferably 300,000 or less. If the weight average molecular weight of the (meth)acrylonitrile polymer is within the above range, the (meth)acrylonitrile polymer exhibits sufficient strength and membrane formability.

In the present invention, it is preferable to use a hydrophilic polymer together with the (meth)acrylonitrile polymer in order to control the pore size of the membrane and provide the membrane with hydrophilicity. Examples of the hydrophilic polymer include polyvinylpyrrolidone, polyethylene glycol, polypropylene glycol, polyethylene oxide, a polyethylene glycol-polypropylene glycol block copolymer, polyvinyl alcohol, poly(meth)acrylamide, poly-N,N-dimethyl(meth)acrylamide, poly-N-isopropyl(meth)acrylamide, polyhydroxy acrylate, polyhydroxy methacrylate, carboxymethyl cellulose, starch, cornstarch, polychitosan, polychitin, and the like. Among these, it is preferable to use polyvinylpyrrolidone that exhibits excellent mutual solubility with the (meth)acrylonitrile polymer and increases the hydrophilicity of the entire membrane.

The lower limit of the weight average molecular weight of the hydrophilic polymer that provides the (meth)acrylonitrile polymer membrane used in the present invention with hydrophilicity is 1,000 or more, and preferably 5,000 or more. The upper limit of the weight average molecular weight of the hydrophilic polymer is 2,000,000 or less, preferably 1,000,000 or less, and particularly preferably 500,000 or less. For example, various grades of polyvinylpyrrolidone are commercially available from BASF. It is preferable to use polyvinylpyrrolidone having a weight average molecular weight of 9,000 (K17), 45,000 (K30), 450,000 (K60), 900,000 (K80), or 1,200,000 (K90). These grades of polyvinylpyrrolidone may be used either individually or in combination according to the desired application, characteristics, and structure.

The molecular weight cut-off of the (meth)acrylonitrile polymer membrane used in the present invention is not particularly limited insofar as immunoglobulin monomers can be sufficiently separated from immunoglobulin dimers. The lower limit of the molecular weight cut-off of the (meth)acrylonitrile polymer membrane is 100,000 or more, preferably 150,000 or more, and more preferably 250,000 or more. The upper limit of the molecular weight cut-off of the (meth)acrylonitrile polymer membrane is 500,000 or less, preferably 450,000 or less, and more preferably 400,000 or less. If the molecular weight cut-off of the (meth)acrylonitrile polymer membrane is less than 100,000, the amount of immunoglobulin that passes through the membrane decreases. If the molecular weight cut-off of the (meth)acrylonitrile polymer membrane is more than 500,000, immunoglobulin monomers and immunoglobulin dimers pass through the membrane (i.e., the fractionation performance decreases).

In the present invention, the molecular weight cut-off is calculated as a molecular weight that provides a blocking rate of 90% based on the correlation between molecular weight and blocking rate when performing dead-end filtration using a protein such as albumin (66,000), γ-globulin (160,000), catalase (232,000), ferritin (440,000), thyroglobulin (669,000), PEG, dextran, or the like.

A method of producing the (meth)acrylonitrile polymer membrane used in the present invention is not particularly limited. For example, a wet membrane-forming method may be used to produce the (meth)acrylonitrile polymer membrane. The wet membrane-forming method is a method that obtains a membrane by causing a membrane raw material solution in which a membrane material is dissolved in a good solvent to come in contact with a coagulation liquid (solvent) that is miscible with the good solvent in the membrane raw material solution, but is not mutually soluble with the membrane material so that concentration-induced phase separation occurs from the contact surface.

The good solvent used in the wet membrane-forming method to obtain the (meth)acrylonitrile polymer membrane according to the present invention is not particularly limited insofar as the good solvent is miscible with water. It is preferable to use a good solvent that can be dissolved in 100 g of purified water (20° C.) in an amount of 10 g or more, and dissolves 5 wt % or more of the (meth)acrylonitrile polymer (membrane material). Examples of the good solvent include N-methyl-2-pyrrolidone, N,N-dimethylacetamide, dimethylsulfoxide, N,N-dimethylformamide, acetone, γ-butyrolactone, and the like. It is preferable to use dimethyl sulfoxide, N,N-dimethylacetamide, or N-methyl-2-pyrrolidone from the viewpoint of safety and non-toxicity. These solvents may be used either individually or in combination.

The membrane raw material solution used in the wet membrane-forming method to obtain the (meth)acrylonitrile polymer membrane according to the present invention is not particularly limited insofar as a (meth)acrylonitrile polymer membrane having the desired structure and performance can be produced. Membrane formability is improved as the concentration of the (meth)acrylonitrile polymer in the membrane raw material solution increases. On the other hand, the porosity of the membrane decreases as the concentration of the (meth)acrylonitrile polymer increases so that water permeability tends to decrease. The (meth)acrylonitrile polymer is used in an amount of 2 wt % or more, preferably 5 wt % or more, and particularly preferably 10 wt % or more, based on the membrane raw material solution (=100 wt %). The upper limit of the concentration of the (meth)acrylonitrile polymer is 50 wt % or less, preferably 40 wt % or less, and particularly preferably 30 wt % or less. A solution in which the (meth)acrylonitrile polymer is homogeneously dissolved is preferably used. If the concentration of the (meth)acrylonitrile polymer is less than 2 wt %, the viscosity of the membrane raw material solution decreases so that it may be difficult to form a membrane. If the concentration of the (meth)acrylonitrile polymer is more than 50 wt %, the viscosity of the membrane raw material solution increases to a large extent so that it may be difficult to form a membrane. A plurality of non-solvents (e.g., water, salt, alcohol, ether, ketone, or glycol) may be added to control the viscosity and the solubility of the membrane raw material solution. The types and the amounts of the non-solvents may be appropriately determined corresponding to the combination.

The lower limit of the temperature of the membrane raw material solution is 0° C. or more, preferably 10° C. or more, and particularly preferably 25° C. or more. The upper limit is preferably equal to or less than the boiling point of the good solvent contained in the membrane raw material solution. If the temperature of the membrane raw material solution is within the above range, a viscosity suitable for producing a membrane can be obtained.

If necessary, additives such as an antioxidant, a nucleating agent, an antistatic agent, a flame retardant, a lubricant, and a UV absorber may be added to the membrane raw material solution used in the present invention insofar as the performance of the resulting membrane is not adversely affected.

The hydrophilic polymer used in the wet membrane-forming method used to obtain the (meth)acrylonitrile polymer membrane according to the present invention mainly promotes formation of a porous structure of an outer porous support layer, and increases the viscosity of the membrane raw material solution. The molecular weight and the amount of the hydrophilic polymer added to the membrane raw material solution may be appropriately adjusted so that a membrane is stably formed. If the viscosity of the membrane raw material solution is low, breakage of the fiber may occur during production (i.e., the fibers may not be stably formed). If the viscosity of the membrane raw material solution is too high, the outer porous support layer may not be sufficiently formed (grown) so that the porosity of the outer-layer porous structure may become insufficient. As a result, a membrane having high permeability may not be obtained. Moreover, the membrane raw material solution discharged from the spinneret is feared to undergo a melt fracture phenomenon due to an increase in the viscosity of the membrane raw material solution.

In the wet membrane-forming method used to obtain the (meth)acrylonitrile polymer membrane according to the present invention, the upper limit value of the concentration of the hydrophilic polymer in the membrane raw material solution is appropriately determined based on the type and the molecular weight of the hydrophilic polymer. The upper limit value of the concentration of the hydrophilic polymer is normally 40 wt % or less, and preferably 30 wt % or less.

The coagulation liquid used in the wet membrane-forming method to obtain the (meth)acrylonitrile polymer membrane according to the present invention is not particularly limited insofar as the coagulation liquid causes concentration-induced phase separation when coming in contact with the membrane raw material solution and forms a membrane from the contact surface. For example, purified water, a monohydric alcohol solvent, a polyol solvent, or a mixture thereof is preferably used as the coagulation liquid. Examples of the monohydric alcohol solvent include methanol, ethanol, propanol, and the like. Examples of the polyol solvent include ethylene glycol, diethylene glycol, triethylene glycol, tetraethylene glycol, glycerol, propylene glycol, 1,2-butanediol, 1,4-butanediol, and the like. A water-soluble polymer such as polyvinyl alcohol, polyethylene glycol, polypropylene glycol, polyethylene oxide, a polyethylene glycol-polypropylene glycol block copolymer, poly(meth)acrylamide, polyvinylpyrrolidone, polyhydroxy acrylate, polyhydroxy methacrylate, poly(meth)acrylic acid, polymethacrylic acid, polyitaconic acid, polyfumaric acid, polycitraconic acid, poly-p-styrene sulfonic acid, sodium poly-p-styrene sulfonate, N,N-dimethyl(meth)acrylamide, carboxymethylcellulose, starch, cornstarch, polychitosan, or polychitin may be added to the coagulation liquid. A liquid that does not dissolve the polymer (e.g., an aliphatic hydrocarbon such as n-hexane or n-heptane) may also be added to the coagulation liquid. The filtration performance of the membrane can be improved by adding such a water-soluble polymer, although the improvement effect varies depending on the molecular weight and the amount of the water-soluble polymer. It is also possible to add a good solvent such as N-methyl-2-pyrrolidone, N,N-dimethylacetamide, dimethyl sulfoxide, N,N-dimethylformamide, γ-butyrolactone, propylene carbonate, or ethylene carbonate to the coagulation liquid. When using a coagulation liquid that contains a good solvent and a non-solvent, the concentration of the good solvent in the coagulation liquid (=100 wt %) is preferably 90 wt % or more, although the composition varies depending on the composition of the membrane raw material solution, the contact temperature of the membrane raw material solution and the coagulation liquid, and the like. If the concentration of the good solvent is within the above range, concentration-induced phase separation sufficient to form a membrane occurs.

The membrane-forming temperature in the wet membrane-forming method used to produce the (meth)acrylonitrile polymer membrane according to the present invention refers to a temperature at which the membrane raw material solution is caused to come in contact with the coagulation liquid so that concentration-induced phase separation occurs. The lower limit of the membrane-forming temperature is 0° C. or more, preferably 10° C. or more, and particularly preferably 25° C. or more. The upper limit is equal to or less than the boiling point of the membrane raw material solution or the coagulation liquid, preferably a temperature lower than the boiling point of the membrane raw material solution or the coagulation liquid by 5° C. or more, and particularly preferably a temperature lower than the boiling point of the membrane raw material solution or the coagulation liquid by 10° C. or more. The membrane-forming temperature is determined by the temperature of a double spinneret when producing a hollow fiber membrane. The membrane-forming temperature is determined by the temperature of the coagulation liquid when producing a flat membrane.

It is desirable to remove dissolved gas from the membrane raw material solution and the coagulation liquid (particularly a coagulation liquid that is passed through a fiber when producing a hollow fiber membrane (hereinafter referred to as "internal coagulation liquid")) used in the wet membrane-forming method to obtain the (meth)acrylonitrile polymer membrane according to the present invention after homogeneously dissolving each component. Defects of the membrane due to foaming of the dissolved gas can be significantly suppressed by removing the dissolved gas. In particular, removal of oxygen reduces an oxidation reaction of a material during membrane processing at a high temperature. This step may be omitted when gas is not dissolved in the membrane raw material solution, the coagulation liquid, and the internal coagulation liquid.

When producing a hollow fiber membrane using the wet membrane-forming method used to produce the (meth)acrylonitrile polymer membrane according to the present invention, in order to allow the membrane raw material solution discharged from a double spinneret to promptly coagulate due to the internal coagulation liquid, a bath (hereinafter referred to as "coagulation bath") may be provided directly under the spinneret, and the membrane raw material solution may be caused to come in contact with a coagulation liquid (hereinafter referred to as "external coagulation liquid") provided in the coagulation bath.

When producing a hollow fiber membrane using the wet membrane-forming method used to produce the (meth)acrylonitrile polymer membrane according to the present invention, the distance from the spinneret to the liquid surface of the external coagulation liquid (hereinafter referred to as "air gap distance") and the temperature and the humidity in the space from the spinneret to the liquid surface of the external coagulation liquid may be adjusted in order to arbitrarily control the cross-sectional structure of the hollow fiber membrane (e.g., uniform structure or non-uniform structure). For example, the lower limit of the air gap distance is 0.001 m or more, preferably 0.005 m or more, and particularly preferably 0.01 m or more, and the upper limit of the air gap distance is 2.0 m or less, preferably 1.5 m or less, and particularly preferably 1.2 m or less. The lower limit of the temperature in the space from the spinneret to the liquid surface of the external coagulation liquid is 10° C. or more, preferably 20° C. or more, and particularly preferably 25° C. or more. The lower limit of the humidity in the space from the spinneret to the liquid surface of the external coagulation liquid is 0% or more, preferably 10% or more, and particularly preferably 30% or more, and the upper limit of the humidity is 100% or less, although the humidity varies depending on the temperature.

The take-up speed when producing a hollow fiber membrane using the wet membrane-forming method used to produce the (meth)acrylonitrile polymer membrane according to the present invention is generally 300 m/h to 9,000 m/h, although the take-up speed varies depending on the production conditions, the shape of the spinneret, the composition of the spinning raw solution, the compositions of the internal coagulation liquid and the external coagulation liquid, the temperatures of the raw solution and the coagulation liquids, and the like.

In the wet membrane-forming method used to produce the (meth)acrylonitrile polymer membrane according to the present invention, it is possible to accelerate removal of the solvent after coagulation with the coagulation liquid by immersing the membrane in a solvent removal liquid in order to increase the strength of the membrane. The solvent removal liquid is a liquid that can remove the solvent remaining after concentration-induced phase separation using the coagulation liquid. Any solvent may be used insofar as the membrane is not dissolved. Water, ethanol, or the like is generally used as the solvent removal liquid.

An undried (meth)acrylonitrile polymer membrane obtained by the wet membrane-forming method according to the present invention is dried at a temperature at which breakage of the membrane does not occur (e.g., a temperature between 20° C. and a temperature equal to or lower than the melting point of the (meth)acrylonitrile polymer). The drying temperature is preferably 30 to 75° C. The drying time is determined based on the drying temperature. The drying time is generally 0.01 to 48 hours.

The lower limit of the weight average molecular weight of the fluorinated polymer used in the present invention is 50,000 or more, preferably 100,000 or more, and particularly preferably 150,000 or more. The upper limit of the weight average molecular weight of the fluorinated polymer is 5,000,000 or less, preferably 2,000,000 or less, and particularly preferably 1,000,000 or less. It is normally difficult to measure the molecular weight of a resin having an average molecular weight of more than 1,000,000 by gel permeation chromatography (GPC). In this case, the viscosity average molecular weight measured by viscometry may be used. If the average molecular weight is less than 50,000, melt tension during melt-forming decreases so that formability deteriorates or the mechanical strength of the membrane decreases. If the average molecular weight is more than 5,000,000, uniform melt-mixing becomes difficult.

It is necessary to provide the membrane with hydrophilicity in order to prevent clogging of the membrane due to adsorption of the immunoglobulin. Examples of the hydrophilization method include a method that immerses the fluorinated polymer membrane in a solution containing a surfactant, and dries the fluorinated polymer membrane so that the surfactant remains in the fluorinated polymer membrane, a method that grafts the surface of the pores in the fluorinated polymer membrane with a hydrophilic acrylic monomer, methacrylic monomer, or the like by applying radiation (e.g., electron beams or γ-rays) or utilizing a peroxide, a method that mixes a hydrophilic polymer during membrane formation, a method that immerses the fluorinated polymer membrane in a solution containing a hydrophilic polymer, and dries the fluorinated polymer membrane so that the surface of the pores in the fluorinated polymer membrane is covered with a coat of the hydrophilic polymer, and the like. It is preferable to utilize graft polymerization taking account of the permanence of hydrophilization and the possibility of leakage of hydrophilic additives. In particular, the hydrophilization process utilizing radiation graft polymerization disclosed in JP S62-179540 A, JP S62-258711 A, and U.S. Pat. No. 4,885,086 is preferable since a uniform hydrophilic layer can be formed on the inner surface of the pores over the entire membrane.

The hydrophilic monomer used for graft polymerization in the present invention is not particularly limited insofar as the hydrophilic monomer contains a vinyl group. It is preferable to use a monomer that contains one vinyl group. A (meth) acrylic monomer that contains a sulfone group, a carboxyl group, an amide group, a neutral hydroxyl group, a sulfonyl group, a sulfonic acid group, or the like may also be preferably used. It is particularly preferable to use a monomer that contains a neutral hydroxyl group when filtering a solution containing the immunoglobulin. The term "hydrophilic monomer" used herein refers to a monomer that is uniformly dissolved under atmospheric pressure when mixed with purified water (25° C.) in an amount of 1 vol %. Examples of the hydrophilic monomer include vinyl monomers containing a hydroxyl group or a functional group that serves as a precursor of a hydroxyl group (e.g., hydroxypropyl acrylate), vinyl monomers containing an anion-exchange group (e.g., triethylammonium ethyl methacrylate), vinyl monomers containing a cation-exchange group (e.g., sulfopropyl methacrylate), vinyl monomers having an amide bond (e.g., vinylpyrrolidone), and the like. Among these, vinyl monomers containing one or more hydroxyl groups or a functional group that serves as a precursor of a hydroxyl group are preferable due to high immunoglobulin solution permeability. Specific examples of such vinyl monomers include esters of (meth)acrylic acid and a polyhydric alcohol (e.g., hydroxypropyl acrylate and 2-hydroxyethyl methacrylate), alcohols having an unsaturated bond (e.g., allyl alcohol), enol esters (e.g., vinyl acetate and vinyl propionate), and the like. A crosslinking agent containing two or more vinyl groups may be used together with a hydrophilic monomer containing one vinyl group in an amount of 20 to 1,000 mol % based on the hydrophilic monomer, and subjected to graft copolymerization so that sufficient hydrophilization is achieved.

The crosslinking agent used in the present invention contains two or more vinyl groups and is copolymerizable with the hydrophilic monomer. The crosslinking agent is introduced by causing the crosslinking agent to come in contact with the membrane simultaneously with the hydrophilic monomer. The lower limit of the number average molecular weight of the crosslinking agent is 200 or more, preferably 250 or more, and more preferably 300 or more, and the upper limit of the number average molecular weight of the crosslinking agent is 2,000 or less, preferably 1,000 or less, and more preferably 600 or less. If the number average molecular weight of the crosslinking agent is 200 to 2,000, a high speed for immunoglobulin solution filtration can be achieved. In the present invention, an arbitrary crosslinking agent containing two or more vinyl groups may be used. It is preferable to use a hydrophilic crosslinking agent. The term "hydrophilic crosslinking agent" used herein refers to a crosslinking agent that is uniformly dissolved under atmospheric pressure when mixed with purified water (25° C.) in an amount of 1 vol %.

Specific examples of the crosslinking agent used in the present invention include aromatic crosslinking agents such as divinylbenzene derivatives, and aliphatic crosslinking agents, e.g., methacrylic acid crosslinking agents such as ethylene glycol dimethacrylate and polyethylene glycol dimethacrylate, and acrylic acid crosslinking agents such as ethylene glycol diacrylate and polyethylene glycol diacrylate, and the like. A crosslinking agent containing three reactive groups (e.g., trimethylolpropane trimethacrylate) may also be used. A mixture of two or more crosslinking agents may also be used. In the present invention, it is most preferable to use polyethylene glycol dimethacrylate, polyethylene glycol diacrylate, or a mixture thereof from the viewpoint of immunoglobulin monomer permeability and immunoglobulin dimer removal performance.

The graft polymerization method used in the present invention is not particularly limited insofar as the method produces radicals. For example, the fluorinated polymer membrane is caused to produce radicals by adding a radiation initiator, applying ionizing radiation, causing a chemical reaction, or the like, and a monomer is graft-polymerized with the membrane starting from the radicals. In the present invention, an arbitrary means may be used to cause the fluorinated polymer membrane to produce radicals. It is preferable to apply ionizing radiation in order to cause the entire membrane to uniformly produce radicals. γ-rays, electron beams, β-rays, neutron beams, or the like may be utilized as ionizing radiation. It is preferable to use electron beams or γ-rays in industrial production. Ionizing radiation may be obtained from a radioactive isotope (e.g., cobalt-60, strontium-90, or cesium-137), X-ray equipment, an electron beam accelerator, an ultraviolet irradiator, or the like.

In the present invention, the dose of ionizing radiation is preferably 1 to 1,000 kGy. If the dose of ionizing radiation is less than 1 kGy, radicals may not be uniformly produced. If the dose of ionizing radiation is more than 1,000 kGy, the strength of the membrane may decrease. The graft polymerization method may be roughly classified as a pre-irradiation method that causes the membrane to produce radicals and then come in contact with reactive compounds, or a simultaneous irradiation method that causes the membrane in contact with reactive compounds to produce radicals. In the present invention, it is preferable to use the pre-irradiation method since it produces oligomers to a small extent.

The fluorinated polymer membrane that has produced radicals may contact with the hydrophilic monomer and the crosslinking agent in a gas phase or a liquid phase. In the present invention, it is preferable to cause the fluorinated polymer membrane to come in contact with the hydrophilic monomer and the crosslinking agent in a liquid phase so that the grafting reaction proceeds uniformly. It is desirable to cause the fluorinated polymer membrane to come in contact with the hydrophilic monomer and the crosslinking agent dissolved in a solvent so that the grafting reaction proceeds more uniformly. The solvent in which the hydrophilic monomer and the crosslinking agent are dissolved is not particularly limited insofar as the hydrophilic monomer and the crosslinking agent can be uniformly dissolved. Examples of the solvent include alcohols such as ethanol, isopropanol, and tert-butyl alcohol, ethers such as diethyl ether and tetrahydrofuran, ketones such as acetone and 2-butanone, water, a mixture thereof, and the like.

In the present invention, graft polymerization is preferably carried out by causing a reaction liquid that contains the hydrophilic monomer and the crosslinking agent in an amount of 0.3 to 30 vol % in total to react with 1 g of the fluorinated polymer membrane in a ratio of $10 \times 10^{-5}$ to $100 \times 10^{-5}$ m$^3$. If graft polymerization is carried out within the above range, a situation in which the pores are filled with the hydrophilic layer is prevented so that a uniform membrane is obtained.

In the present invention, the graft polymerization temperature is not particularly limited insofar as a polymerization reaction occurs. The graft polymerization temperature is normally 20 to 80° C.

In the present invention, when causing the fluorinated polymer membrane to come in contact with the hydrophilic monomer to effect graft polymerization, the hydrophilic monomer may be in the state of gas, liquid, or solution. It is preferable that the hydrophilic monomer be a liquid or a solution in order to form a uniform hydrophilic layer. It is particularly preferable that the hydrophilic monomer be a solution.

The hydrophilic fluorinated polymer membrane according to the present invention exhibits excellent immunoglobulin monomer permeability and immunoglobulin dimer blocking capability as a result of introducing a hydrophilic layer having a strong crosslinked structure into the hydrophobic fluorinated polymer membrane. The crosslinking agent is used in an amount of 20 mol % or more, and preferably 30 mol % or more, but 1,000 mol % or less, preferably 500 mol % or less, and more preferably 200 mol % or less, based on the hydrophilic monomer.

In the present invention, high immunoglobulin monomer permeability is implemented by introducing a hydrophilic layer into the hydrophobic fluorinated polymer membrane. The graft ratio of the hydrophobic fluorinated polymer membrane is 3% or more, preferably 4% or more, and more preferably 5% or more, but 50% or less, preferably 30% or less, and more preferably 20% or less. If the graft ratio is less than 3%, the membrane exhibits insufficient hydrophilicity so that the filtration speed rapidly decreases due to adsorption of proteins. If the graft ratio is more than 50%, smaller pores are filled with the hydrophilic layer so that a sufficient filtration speed may not be achieved. The graft ratio refers to a value defined by the following formula (3).

Graft ratio (%)=(weight of membrane after grafting− weight of membrane before grafting)/(weight of membrane before grafting)×100     (3)

The degree of hydrophilicity of the fluorinated polymer membrane according to the present invention may be evaluated by the contact angle. It is preferable that the average value of the advancing contact angle and the receding contact angle at 25° C. be 60 degree or less, more preferably 45 degree or less, and still more preferably 30 degree or less. If water voluntarily permeates the pores in the fluorinated polymer membrane when causing the fluorinated polymer membrane to come in contact with water, the fluorinated polymer membrane may be considered to have sufficient hydrophilicity.

The molecular weight cut-off of the hydrophilic fluorinated polymer membrane used in the present invention is not particularly limited insofar as immunoglobulin monomers can be sufficiently separated from immunoglobulin dimers. The lower limit of the molecular weight cut-off of the hydrophilic fluorinated polymer membrane is 100,000 or more, preferably 150,000 or more, and more preferably 250,000 or more. The upper limit of the molecular weight cut-off of the hydrophilic fluorinated polymer membrane is 500,000 or less, preferably 450,000 or less, and more preferably 400,000 or less. If the molecular weight cut-off of the hydrophilic fluorinated polymer membrane is less than 100,000, the amount of immunoglobulin that passes through the membrane decreases. If the molecular weight cut-off of the hydrophilic fluorinated polymer membrane is more than 500,000, immunoglobulin monomers and immunoglobulin dimers pass through the membrane (i.e., the fractionation performance decreases).

In the present invention, the molecular weight cut-off is calculated as a molecular weight that provides a blocking rate of 90% based on the correlation between molecular weight and blocking rate when performing dead-end filtration using a protein such as albumin (66,000), γ-globulin (160,000), catalase (232,000), ferritin (440,000), thyroglobulin (669,000), PEG, dextran, or the like.

A method of producing the fluorinated polymer membrane used in the present invention is not particularly limited. For example, a melt membrane-forming method or a wet membrane-forming method may be used to produce the fluorinated polymer membrane. The melt membrane-forming method includes uniformly mixing a membrane material and a plasticizer by heating, causing phase separation by cooling, and extracting the plasticizer from the resulting membrane film to obtain a membrane. The wet membrane-forming method is a method that obtains a membrane by causing a membrane raw material solution in which a membrane material is dissolved in a good solvent to come in contact with a coagulation liquid (solvent) that is miscible with the good solvent in the membrane raw material solution, but is not mutually soluble with the membrane material so that concentration-induced phase separation occurs from the contact surface.

A typical melt membrane-forming method used to produce the fluorinated polymer membrane used in the present invention includes the following steps (a) to (c).

(a) A composition containing the fluorinated polymer and the plasticizer is heated to a temperature equal to or higher than the crystalline melting point of the fluorinated polymer to effect uniform dissolution, and the composition is discharged from a discharge port to form a membrane.

(b) A nonvolatile liquid that partially dissolves the fluorinated polymer is caused to come in contact with one of the surfaces of the membrane at 100° C. or more, and the other surface of the membrane is cooled while withdrawing the membrane at a withdrawing speed so that the draft ratio defined by the following formula (4) is 1 to 15.

$$\text{Draft ratio} = (\text{membrane withdrawing speed})/(\text{composition discharge speed at discharge port}) \quad (4)$$

(c) The plasticizer and the nonvolatile liquid are substantially removed.

The lower limit of the polymer concentration employed in the melt membrane-forming method used to obtain the fluorinated polymer membrane used in the present invention is 20 wt % or more, preferably 30 wt % or more, and particularly preferably 35 wt % or more, based on the composition containing the fluorinated polymer and the plasticizer. The upper limit of the polymer concentration is 90 wt % or less, preferably 80 wt % or less, and more preferably 70 wt % or less. If the polymer concentration is less than 20 wt %, membrane formability may deteriorate, or a membrane having a sufficient mechanical strength may not be obtained. If the polymer concentration is more than 90 wt %, the pore size of the resulting fluorinated polymer membrane may decrease to a large extent. Moreover, the filtration speed may decrease to an impractical level due to a decrease in porosity.

As the plasticizer used in the melt membrane-forming method used to obtain the fluorinated polymer membrane used in the present invention, a nonvolatile solvent that can form a homogeneous solution at a temperature equal to or higher than the crystalline melting point of a resin when mixed with the fluorinated polymer to achieve a composition that produces the fluorinated polymer membrane is used. The term "nonvolatile solvent" used herein refers to a solvent having a boiling point of 250° C. or more under atmospheric pressure. The plasticizer may be liquid or solid at room temperature (approximately 20° C.). A solid-liquid phase separation-type plasticizer that has a thermally induced solid-liquid phase separation point at a temperature equal to or higher than room temperature when cooling a homogeneous solution of the plasticizer and the fluorinated polymer, may also be used. Some plasticizers have a thermally induced liquid-liquid phase separation point at a temperature equal to or higher than room temperature when cooling a homogeneous solution of the plasticizer and the fluorinated polymer. When using such a liquid-liquid phase separation-type plasticizer, the resulting fluorinated polymer membrane may have large pores. The plasticizer may be a single substance, or a mixture of a plurality of substances.

The thermally induced solid-liquid phase separation point may be determined by measuring the exothermic peak temperature of a sample prepared by melt-mixing a composition that includes the fluorinated polymer and the plasticizer and has a given concentration by thermal analysis such as differential scanning calorimetry (DSC). The crystallization point of the resin may be similarly determined by thermal analysis using a sample prepared by melt-mixing the resin.

In the present invention, the plasticizer disclosed in WO01/28667 may be used. Specifically, it is preferable to use a plasticizer of which the phase separation point-decrease constant α of the composition defined by the following formula (5) is 0° C. or more, preferably 1° C. or more, and more preferably 5° C. or more, but 40° C. or less, preferably 35° C. or less, and more preferably 30° C. or less. If the depression constant of the phase separation point is more than 40° C., the pore diameter homogeneity and the strength of the membrane decrease.

$$\alpha = 100 \times (T_c^0 - T_c) \div (100 - C) \quad (5)$$

α: depression constant of the phase separation point (° C.)
$T_c^0$: crystallization temperature (° C.) of fluorinated polymer
$T_c$: thermally induced solid-liquid phase separation point (° C.) of composition
C: concentration (wt %) of fluorinated polymer in composition As the plasticizer, a phthalate, an adipate, or a sebacate of which the carbon chain length of the ester chain is seven or less, a phosphate or a citrate of which the carbon chain length of the ester chain is eight or less, or the like may be suitably used. It is particularly preferable to use diheptyl phthalate, dicyclohexyl phthalate, dibutyl phthalate, diethyl phthalate, dimethyl phthalate, dibutyl adipate, dibutyl sebacate, triphenyl phosphate, tricresyl phosphate, diphenyl cresyl phosphate, tri(2-ethylhexyl) phosphate, tributyl phosphate, acetyl tributyl citrate, or the like as the plasticizer.

If necessary, additives such as an antioxidant, a nucleating agent, an antistatic agent, a flame retardant, a lubricant, and a UV absorber may be added to the composition used in the present invention insofar as the performance of the resulting membrane is not adversely affected.

The first method that obtains a homogeneous solution of a composition containing the fluorinated polymer and the plasticizer in the melt membrane-forming method used to obtain the fluorinated polymer membrane used in the present invention includes introducing the resin into a continuous resin mixer (e.g., extruder), introducing the plasticizer in an arbitrary ratio while melting the resin by heating, and mixing the mixture using a screw to obtain a homogeneous solution. The resin may be a powder, granules, or pellets. It is preferable that the plasticizer be liquid at room temperature when using the first method. As the extruder, a single-screw extruder, a counter-rotating twin-screw extruder, a co-rotating twin-screw extruder, or the like may be used.

The second method that obtains a homogeneous solution of a composition containing the fluorinated polymer and the plasticizer includes mixing and dispersing of the fluorinated polymer and the plasticizer beforehand using a stirrer (e.g., Henschel mixer), introducing the resulting composition into a continuous resin mixer (e.g., extruder), and melt-mixing the composition to obtain a homogeneous solution. The composition may be in the form of a slurry when the plasticizer is liquid at room temperature, and may be in the form of a powder, granules, or the like when the plasticizer is solid at room temperature.

The third method that obtains a homogeneous solution of a composition containing the fluorinated polymer and the plasticizer includes melt-mixing of the composition using a simple resin mixer (e.g., Brabender mixer or a mill) or a batch-type mixer. The third method is not necessarily productive due to the batch operation, but is convenient and highly flexible.

In the melt membrane-forming method used to obtain the fluorinated polymer membrane used in the present invention, a composition containing the fluorinated polymer and the plasticizer is heated to a temperature equal to or higher than the crystalline melting point of the fluorinated polymer to obtain a homogeneous solution, the solution is extruded into a flat membrane or a hollow fiber membrane from a discharge port of a T-die, a circular die, or a circular spinneret (step (a)), and the extruded product is cooled and solidified (step (b)) to form a membrane structure.

In the melt membrane-forming method used to obtain the fluorinated polymer membrane used in the present invention, the homogeneous solution of the composition containing the fluorinated polymer and the plasticizer obtained by heating is discharged from the discharge port, and is withdrawn at a withdrawing speed so that the draft ratio defined by the following formula (6) is 1 to 15 while causing a nonvolatile liquid that partially dissolves the fluorinated polymer to come in contact with the fluorinated polymer to form a membrane.

$$\text{Draft ratio} = (\text{membrane withdrawing speed})/(\text{composition discharge speed at discharge port}) \quad (6)$$

The draft ratio is 1.5 or more, and preferably 2 or more, but 10 or less, and preferably 7 or less. If the draft ratio is less than 1, tension is not applied to the membrane so that formability decreases. If the draft ratio is more than 15, the membrane is stretched so that it is difficult to form a coarsely structured layer having a sufficient thickness. The discharge speed of the composition from the discharge port is defined by the following formula (7).

$$\text{Discharge speed of composition from discharge port} = (\text{volume of composition discharged per unit time})/(\text{area of discharge port}) \quad (7)$$

The discharge speed is 1 m/min or more, and preferably 3 m/min or more, but 60 in/min or less, and preferably 40 m/min or less. If the discharge speed is less than 1 m/min, productivity decreases. Moreover, the discharge amount varies to a large extent. If the discharge speed exceeds 60 m/min, a turbulent flow may occur at the discharge port due to a large discharge amount (i.e., the discharge state may become unstable). The withdrawing speed may be set according to the discharge speed. The withdrawing speed is 1 m/min or more, and preferably 3 m/min or more, but 200 m/min or less, and preferably 150 m/min or less. If the withdrawing speed is less than 1 m/min, productivity and formability decrease. If the withdrawing speed exceeds 200 m/min, the membrane tends to break due to a decrease in cooling time and an increase in tension applied to the membrane.

In the present invention, an extraction solvent is used to remove the plasticizer. It is preferable that the extraction solvent be a poor solvent for the fluorinated polymer and a good solvent for the plasticizer, and have a boiling point higher than the melting point of the fluorinated polymer membrane. Examples of the extraction solvent include hydrocarbons such as hexane and cyclohexane, halogenated hydrocarbons such as methylene chloride and 1,1,1-trichloroethane, alcohols such as ethanol and isopropanol, ethers such as diethyl ether and tetrahydrofuran, ketones such as acetone and 2-butanone, and water.

In the present invention, the first method that removes the plasticizer includes immersing the fluorinated polymer membrane cut to given dimensions in a container that contains the extraction solvent, sufficiently washing the fluorinated polymer membrane with the extraction solvent, and air-drying the solvent adhering to the fluorinated polymer membrane, or drying the solvent by applying a hot air blast. It is preferable to repeat the immersion operation and the washing operation a number of times so that the amount of the plasticizer that remains in the fluorinated polymer membrane decreases. It is preferable to hold the ends of the fluorinated polymer membrane in order to suppress shrinkage of the fluorinated polymer membrane during the immersion operation, the washing operation, and the drying operation.

The second method that removes the plasticizer includes continuously introducing the fluorinated polymer membrane into a bath filled with the extraction solvent, immersing the fluorinated polymer membrane in the bath for a period of time sufficient to remove the plasticizer, and drying the solvent adhering to the fluorinated polymer membrane. The extraction efficiency can be improved by sequentially introducing the fluorinated polymer membrane into baths that differ in concentration of the extraction solvent (multi-stage method), or supplying the extraction solvent in the direction opposite to the travel direction of the fluorinated polymer membrane to form a concentration gradient (counter-flow method), for example. In the first and second methods, it is important to substantially remove the plasticizer from the fluorinated polymer membrane. The expression "substantially remove" means removing the plasticizer from the fluorinated polymer membrane to such an extent that the performance of the separation membrane is not adversely affected. The amount of the plasticizer that remains in the fluorinated polymer membrane is preferably 1 wt % or less, and more preferably 100 ppm by weight or less. The amount of the plasticizer that remains in the fluorinated polymer membrane may be determined by gas chromatography, liquid chromatography, or the like. Diffusion of the plasticizer and the solvent can be promoted by heating the extraction solvent to a temperature lower than the boiling point of the extraction solvent (preferably by 5° C. or less).

In the present invention, if the fluorinated polymer membrane is heated before, after, or before and after removing the plasticizer, shrinkage of the fluorinated polymer membrane upon removing the plasticizer can be suppressed, and the strength and the heat resistance of the fluorinated polymer membrane can be improved. The fluorinated polymer membrane may be heated by applying a hot air blast to the fluorinated polymer membrane, immersing the fluorinated polymer membrane in a heat medium, or causing the fluorinated polymer membrane to come in contact with a heated metal roll or the like. It is preferable to heat the fluorinated polymer membrane while fixing the dimensions of the fluorinated polymer membrane in order to prevent clogging of minute pores. The heating temperature is preferable equal to or lower than the melting point of the fluorinated polymer. When using polyvinylidene fluoride, the heating temperature is 121° C. or more, and preferably 125° C. or more, but 170° C. or less, and preferably 165° C. or less. If the heating temperature is higher than the melting point of the fluorinated polymer, the membrane may break during heating, or the pores in the membrane may be crushed.

A typical wet membrane-forming method used to obtain the fluorinated polymer membrane used in the present invention is described below.

The good solvent used in the wet membrane-forming method to obtain the fluorinated polymer membrane according to the present invention is not particularly limited insofar as the good solvent is miscible with water. It is preferable to use a good solvent that can be dissolved in 100 g of purified water (20° C.) in an amount of 10 g or more, and dissolves 5 wt % or more of the fluorinated polymer (membrane material). Examples of the good solvent include N-methyl-2-pyrrolidone, N,N-dimethylacetamide, dimethylsulfoxide, N,N-dimethylformamide, acetone, γ-butyrolactone, and the like. It is preferable to use dimethyl sulfoxide, N,N-dimethylacetamide, or N-methyl-2-pyrrolidone from the viewpoint of safety and non-toxicity. These solvents may be used either individually or in combination.

The membrane raw material solution used in the wet membrane-forming method to obtain the fluorinated polymer membrane according to the present invention is not particularly limited insofar as a fluorinated polymer membrane having the desired structure and performance can be produced. The membrane formability is improved as the concentration of the fluorinated polymer in the membrane raw material solution increases. On the other hand, the porosity of the membrane decreases as the concentration of the fluorinated polymer increases so that water permeability tends to decrease. The fluorinated polymer is used in an amount of 2 wt % or more, preferably 5 wt % or more, and particularly preferably 10 wt % or more, based on the membrane raw material solution (=100 wt %). The upper limit is 50 wt % or less, preferably 40 wt % or less, and particularly preferably 30 wt % or less. A solution in which the fluorinated polymer is homogeneously dissolved is preferably used.

The lower limit of the temperature of the membrane raw material solution is 0° C. or more, preferably 10° C. or more, and particularly preferably 25° C. or more. The upper limit of the temperature of the membrane raw material solution is preferably equal to or less than the boiling point of the good solvent contained in the membrane raw material solution. If the temperature of the membrane raw material solution is within the above range, a viscosity suitable for producing a membrane can be obtained.

If necessary, additives such as an antioxidant, a nucleating agent, an antistatic agent, a flame retardant, a lubricant, and a UV absorber may be added to the membrane raw material solution used in the present invention insofar as the performance of the resulting membrane is not adversely affected.

The hydrophilic polymer used in the wet membrane-forming method used to obtain the fluorinated polymer membrane according to the present invention mainly promotes formation of a porous structure of an outer porous support layer, and increases the viscosity of the membrane raw material solution. The molecular weight and the amount of the hydrophilic polymer added to the membrane raw material solution may be appropriately adjusted so that a membrane is stably formed. If the viscosity of the membrane raw material solution is low, breakage of the membrane may occur during production (i.e., the membrane may not be stably formed). If the viscosity of the membrane raw material solution is too high, the outer porous support layer may not be sufficiently formed (grown) so that the porosity of the outer-layer porous structure may become insufficient. As a result, a membrane having high permeability may not be obtained. Moreover, the membrane raw material solution discharged from the spinneret is feared to undergo a melt fracture phenomenon due to an increase in the viscosity of the membrane raw material solution.

In the wet membrane-forming method used to obtain the fluorinated polymer membrane according to the present invention, the upper limit value of the concentration of the hydrophilic polymer in the membrane raw material solution is appropriately determined based on the type and the molecular weight of the hydrophilic polymer. The upper limit value of the concentration of the hydrophilic polymer is normally 40 wt % or less, and preferably 30 wt % or less.

The coagulation liquid used in the wet membrane-forming method to obtain the fluorinated polymer membrane according to the present invention is not particularly limited insofar as the coagulation liquid causes concentration-induced phase separation when coming in contact with the membrane raw material solution and forms a membrane from the contact surface. Examples of the coagulation liquid include purified water, a monohydric alcohol solvent, a polyol solvent, a mixture of two or more of these, and the like. Examples of the monohydric alcohol solvent include methanol, ethanol, propanol, and the like. Examples of the polyol solvent include ethylene glycol, diethylene glycol, triethylene glycol, tetraethylene glycol, glycerol, propylene glycol, 1,2-butanediol, 1,4-butanediol, and the like. A water-soluble polymer such as polyvinyl alcohol, polyethylene glycol, polypropylene glycol, polyethylene oxide, a polyethylene glycol-polypropylene glycol block copolymer, poly(meth)acrylamide, polyvinylpyrrolidone, polyhydroxy acrylate, polyhydroxy methacrylate, poly(meth)acrylic acid, polymethacrylic acid, polyitaconic acid, polyfumaric acid, polycitraconic acid, poly-p-styrene sulfonic acid, sodium poly-p-styrene sulfonate, N,N-dimethyl(meth)acrylamide, carboxymethylcellulose, starch, cornstarch, polychitosan, or polychitin may be added to the coagulation liquid. The filtration performance of the membrane can be improved by adding such a water-soluble polymer, although the improvement effect varies depending on the molecular weight and the amount of the water-soluble polymer. It is also possible to add a good solvent such as N-methyl-2-pyrrolidone, N,N-dimethylacetamide, dimethyl sulfoxide, N,N-dimethylformamide, or γ-butyrolactone to the coagulation liquid. When using a coagulation liquid that contains a good solvent and a non-solvent, the concentration of the good solvent in the coagulation liquid (=100 wt %) is preferably 90 wt % or more, although the composition varies depending on the composition of the membrane raw material solution, the contact temperature of the membrane raw material solution and the coagulation liquid, and the like. If the concentration of the good solvent is within the above range, concentration-induced phase separation sufficient to form a membrane occurs.

The membrane-forming temperature in the wet membrane-forming method used to produce the fluorinated polymer membrane according to the present invention refers to a temperature at which the membrane raw material solution is caused to come in contact with the coagulation liquid so that concentration-induced phase separation occurs. The lower limit of the membrane-forming temperature is 0° C. or more, preferably 10° C. or more, and particularly preferably 25° C. or more. The upper limit is equal to or less than the boiling point of the membrane raw material solution or the coagulation liquid, preferably a temperature lower than the boiling point of the membrane raw material solution or the coagulation liquid by 5° C. or more, and particularly preferably a temperature lower than the boiling point of the membrane raw material solution or the coagulation liquid by 10° C. or more. The membrane-forming temperature is determined by the temperature of a double spinneret when producing a hollow fiber membrane. The membrane-forming temperature is determined by the temperature of the coagulation liquid when producing a flat membrane.

It is desirable to remove dissolved gas from the membrane raw material solution and the coagulation liquid (particularly a coagulation liquid that is caused to flow through a fiber when producing a hollow fiber membrane (hereinafter referred to as "internal coagulation liquid")) used in the wet membrane-forming method to produce the fluorinated polymer membrane according to the present invention after homogeneously dissolving each component. Defects of the membrane due to foaming of the dissolved gas can be significantly suppressed by removing the dissolved gas. In particular, removal of oxygen reduces an oxidation reaction of a material during membrane processing at a high temperature. This step may be omitted when gas is not dissolved in the membrane raw material solution, the coagulation liquid, and the internal coagulation liquid.

When producing a hollow fiber membrane using the wet membrane-forming method used to produce the fluorinated polymer membrane according to the present invention, in order to allow the membrane raw material solution discharged from a double spinneret to promptly coagulate due to the internal coagulation liquid, a bath (hereinafter referred to as "coagulation bath") may be provided directly under the spinneret, and the membrane raw material solution may be caused to come in contact with a coagulation liquid (hereinafter referred to as "external coagulation liquid") provided in the coagulation bath.

When producing a hollow fiber membrane using the wet membrane-forming method used to produce the fluorinated polymer membrane according to the present invention, the distance from the spinneret to the liquid surface of the external coagulation liquid (hereinafter referred to as "air gap distance") and the temperature and the humidity in the space from the spinneret to the liquid surface of the external coagulation liquid, may be adjusted in order to arbitrarily control the cross-sectional structure of the hollow fiber membrane (e.g., uniform structure or non-uniform structure). For example, the lower limit of the air gap distance is 0.001 m or more, preferably 0.005 m or more, and particularly preferably 0.01 m or more, and the upper limit of the air gap distance is 2.0 m or less, preferably 1.5 m or less, and particularly preferably 1.2 m or less. The lower limit of the temperature in the space from the spinneret to the liquid surface of the external coagulation liquid is 10° C. or more, preferably 20° C. or more, and particularly preferably 25° C. or more. The lower limit of the humidity in the space from the spinneret to the liquid surface of the external coagulation liquid is 0% or more, preferably 10% or more, and particularly preferably 30% or more, and the upper limit of the humidity is 100% or less, although the humidity varies depending on the temperature.

The take-up speed when producing a hollow fiber membrane using the wet membrane-forming method used to produce the fluorinated polymer membrane according to the present invention is generally 300 m/h to 9,000 m/h, although the take-up speed varies depending on the production conditions, the shape of the spinneret, the composition of the spinning raw solution, the compositions of the internal coagulation liquid and the external coagulation liquid, the temperatures of the raw solution and the coagulation liquids, and the like.

In the wet membrane-forming method used to produce the fluorinated polymer membrane according to the present invention, it is possible to accelerate removal of the solvent after coagulation with the coagulation liquid by immersing the membrane in a solvent removal liquid in order to increase the strength of the membrane. The solvent removal liquid is a liquid that can remove the solvent remaining after concentration-induced phase separation using the coagulation liquid. Any solvent may be used insofar as the membrane is not dissolved. Water, ethanol, or the like is generally used as the solvent removal liquid.

An undried fluorinated polymer membrane obtained by the wet membrane-forming method according to the present invention is dried at a temperature at which breakage of the membrane does not occur (e.g., a temperature between 20° C. and a temperature equal to or lower than the melting point of the fluorinated polymer). The lower limit of the drying temperature is 30° C. or more, and preferably 40° C. or more. The upper limit of the drying temperature is 120° C. or less, and preferably 100° C. or less. The drying time is determined based on the drying temperature. The drying time is generally 0.01 to 48 hours.

The olefin polymer membrane used in the present invention is mainly formed of an olefin polymer. The olefin polymer membrane may contain other polymer substances and additives insofar as the characteristics of the olefin polymer are not adversely affected. These polymers may be used in combination.

The olefin polymer used in the present invention is synthesized using an olefin or an alkene as a monomer. Examples of the olefin polymer include polyethylene, polypropylene, poly-4-methyl-1-pentene. The above homopolymer and copolymer may be used in combination. Among these, it is preferable to use polyethylene.

The lower limit of the weight average molecular weight of the olefin polymer used in the present invention is 50,000 or more, preferably 100,000 or more, and particularly preferably 150,000 or more. The upper limit of the weight average molecular weight of the olefin polymer is 5,000,000 or less, preferably 2,000,000 or less, and particularly preferably 1,000,000 or less. It is normally difficult to measure the molecular weight of a resin having an average molecular weight of more than 1,000,000 by GPC. In this case, a viscosity average molecular weight measured by viscometry may be used. If the average molecular weight is less than 50,000, melt tension during melt-forming decreases so that formability deteriorates or the mechanical strength of the membrane decreases. If the average molecular weight is more than 5,000,000, uniform melt-mixing becomes difficult.

It is necessary to provide the membrane with hydrophilicity in order to prevent clogging of the membrane due to adsorption of the immunoglobulin. Examples of the hydrophilization method include a method that immerses the olefin polymer membrane in a solution containing a surfactant, and dries the olefin polymer membrane so that the surfactant remains in the olefin polymer membrane, a method that grafts the surface of the pores in the olefin polymer membrane with a hydrophilic (meth)acrylic monomer or the like by applying radiation (e.g., electron beams or γ-rays) or utilizing a peroxide, a method that mixes a hydrophilic polymer during membrane formation, and a method that immerses the olefin polymer membrane in a solution containing a hydrophilic polymer, and dries the olefin polymer membrane so that the surface of the pores in the olefin polymer membrane is covered with a coat of the hydrophilic polymer, and the like. It is preferable to utilize graft polymerization taking account of the permanence of hydrophilization and the possibility of leakage of the hydrophilic additives. In particular, the hydrophilization process utilizing radiation graft polymerization disclosed in JP S62-179540 A, JP S62-258711 A, and U.S. Pat. No. 4,885,086 is preferable since a uniform hydrophilized layer can be formed on the inner surface of the pores over the entire membrane.

The hydrophilic monomer used for graft polymerization in the present invention is not particularly limited insofar as the hydrophilic monomer contains a vinyl group. It is preferable to use a monomer that contains one vinyl group. A (meth) acrylic monomer that contains a sulfone group, a carboxyl group, an amide group, a neutral hydroxyl group, a sulfonyl group, a sulfonic acid group, or the like may also be preferably used. It is particularly preferable to use a monomer that contains a neutral hydroxyl group when filtering a solution containing the immunoglobulin. The term "hydrophilic monomer" used herein refers to a monomer that is uniformly dissolved under atmospheric pressure when mixed with purified water (25° C.) in an amount of 1 vol %. Examples of the hydrophilic monomer include vinyl monomers containing a hydroxyl group or a functional group that serves as a precursor of a hydroxyl group (e.g., hydroxypropyl acrylate), vinyl monomers containing an anion-exchange group (e.g., triethylammonium ethyl methacrylate), vinyl monomers containing a cation-exchange group (e.g., sulfopropyl methacrylate), vinyl monomers having an amide bond (e.g., vinylpyrrolidone), and the like. Among these, vinyl monomers containing one or more hydroxyl groups or a functional group that serves as a precursor of a hydroxyl group are preferable due to high immunoglobulin solution permeability.

Specific examples of such vinyl monomers include esters of (meth)acrylic acid and a polyhydric alcohol (e.g., hydroxypropyl acrylate and 2-hydroxyethyl methacrylate), alcohols having an unsaturated bond (e.g., allyl alcohol), enol esters (e.g., vinyl acetate and vinyl propionate), and the like. A crosslinking agent containing two or more vinyl groups may be used together with a hydrophilic monomer containing one vinyl group in an amount of 20 to 1,000 mol % based on the hydrophilic monomer, and subjected to graft copolymerization so that sufficient hydrophilization is achieved.

The crosslinking agent used in the present invention contains two or more vinyl groups and is copolymerizable with the hydrophilic monomer. The crosslinking agent is introduced by causing the crosslinking agent to come in contact with the membrane simultaneously with the hydrophilic monomer. The number average molecular weight of the crosslinking agent is preferably 200 to 2000, more preferably 250 to 1000, and most preferably 300 to 600. If the number average molecular weight of the crosslinking agent is 200 to 2000, a high speed for immunoglobulin solution filtration can be achieved. In the present invention, any crosslinking agent containing two or more vinyl groups may be used. It is preferable to use a hydrophilic crosslinking agent. The term "hydrophilic crosslinking agent" used herein refers to a crosslinking agent that is uniformly dissolved under atmospheric pressure when mixed with purified water (25° C.) in an amount of 1 vol %.

Specific examples of the crosslinking agent used in the present invention include aromatic crosslinking agents such as divinylbenzene derivatives, aliphatic crosslinking agents, e.g., methacrylic acid crosslinking agents such as ethylene glycol dimethacrylate and polyethylene glycol dimethacrylate, and acrylic acid crosslinking agents such as ethylene glycol diacrylate and polyethylene glycol diacrylate, and the like. A crosslinking agent containing three reactive groups (e.g., trimethylolpropane trimethacrylate) may also be used. A mixture of two or more crosslinking agents may also be used. In the present invention, it is most preferable to use polyethylene glycol dimethacrylate, polyethylene glycol diacrylate, or a mixture thereof from the viewpoint of immunoglobulin monomer permeability and immunoglobulin dimer removal performance.

The graft polymerization method used in the present invention is not particularly limited insofar as the method produces radicals. For example, the olefin polymer membrane is caused to produce radicals by adding a radiation initiator, applying ionizing radiation, causing a chemical reaction, or the like, and a monomer is graft-polymerized with the membrane from the radicals (as starting points). In the present invention, an arbitrary means may be used to cause the olefin polymer membrane to produce radicals. It is preferable to apply ionizing radiation in order to cause the entire membrane to uniformly produce radicals. γ-rays, electron beams, β-rays, neutron beams, or the like may be utilized as ionizing radiation. It is preferable to use electron beams or γ-rays in industrial production. Ionizing radiation is obtained from a radioactive isotope (e.g., cobalt-60, strontium-90, or cesium-137), X-ray equipment, an electron beam accelerator, an ultraviolet irradiator, or the like.

In the present invention, the dose of ionizing radiation is preferably 1 to 1,000 kGy. If the dose of ionizing radiation is less than 1 kGy, radicals may not be uniformly produced. If the dose of ionizing radiation is more than 1,000 kGy, the strength of the membrane may decrease. The graft polymerization method may be roughly classified as a pre-irradiation method that causes the membrane to produce radicals and come in contact with a reactive compound, or a simultaneous irradiation method that causes the membrane that comes in contact with a reactive compound to produce radicals simultaneously. In the present invention, it is preferable to use the pre-irradiation method since it produces oligomers to only a small extent.

The olefin polymer membrane that has produced radicals may be caused to come in contact with the hydrophilic monomer and the crosslinking agent in a gas phase or a liquid phase. In the present invention, it is preferable to cause the olefin polymer membrane to come in contact with the hydrophilic monomer and the crosslinking agent in a liquid phase so that the grafting reaction proceeds uniformly. It is desirable to cause the olefin polymer membrane to come in contact with the hydrophilic monomer and the crosslinking agent dissolved in a solvent so that the grafting reaction proceeds more uniformly. The solvent in which the hydrophilic monomer and the crosslinking agent are dissolved is not particularly limited insofar as the hydrophilic monomer and the crosslinking agent can be uniformly dissolved. Examples of the solvent include alcohols such as ethanol, isopropanol, and tert-butyl alcohol, ethers such as diethyl ether and tetrahydrofuran, ketones such as acetone and 2-butanone, water, a mixture thereof, and the like.

In the present invention, graft polymerization is preferably carried out by causing a reaction liquid that contains the hydrophilic monomer and the crosslinking agent in an amount of 0.3 to 30 vol % in total to react with 1 g of the olefin polymer membrane in a ratio of $10 \times 10^{-5}$ to $100 \times 10^{-5}$ m$^3$. If graft polymerization is carried out within the above range, a situation in which the pores are filled with the hydrophilic layer is prevented so that a uniform membrane is obtained.

In the present invention, the graft polymerization temperature is not particularly limited insofar as the polymerization reaction occurs. The graft polymerization temperature is normally 20 to 80° C.

In the present invention, when causing the olefin polymer membrane to come in contact with the hydrophilic monomer to effect graft polymerization, the hydrophilic monomer may be a gas, a liquid, or a solution. It is preferable that the hydrophilic monomer be a liquid or a solution in order to form a uniform hydrophilic layer. It is particularly preferable that the hydrophilic monomer be a solution.

The hydrophilic olefin polymer membrane according to the present invention exhibits excellent immunoglobulin monomer permeability and immunoglobulin dimer blocking capability as a result of introducing a hydrophilic layer having a strong crosslinked structure into the hydrophobic olefin polymer membrane. The crosslinking agent is used in an amount of 20 mol % or more, and preferably 30 mol % or more, but 1,000 mol % or less, preferably 500 mol % or less, and more preferably 200 mol % or less, based on the hydrophilic monomer.

In the present invention, high immunoglobulin monomer permeability is implemented by introducing a hydrophilic layer into the hydrophobic olefin polymer membrane. The graft ratio of the hydrophobic olefin polymer membrane is 3% or more, preferably 4% or more, and more preferably 5% or more, but 50% or less, preferably 30% or less, and more preferably 20% or less. If the graft ratio is less than 3%, the membrane exhibits insufficient hydrophilicity so that the filtration speed rapidly decreases due to adsorption of proteins. If the graft ratio is more than 50%, relatively small pores are filled with the hydrophilic layer so that a sufficient filtration speed may not be achieved. The graft ratio refers to a value defined by the following formula (8).

Graft ratio (%)=(weight of membrane after grafting– weight of membrane before grafting)/(weight of membrane before grafting)×100    (8)

The degree of hydrophilicity of the olefin polymer membrane according to the present invention may be evaluated by the contact angle. It is preferable that the average value of the advancing contact angle and the receding contact angle at 25° C. be 60 degree or less, more preferably 45 degree or less, and still more preferably 30 degree or less. If water voluntarily permeates the pores in the olefin polymer membrane when causing the olefin polymer membrane to come in contact with water, the olefin polymer membrane may be determined to have sufficient hydrophilicity.

The molecular weight cut-off of the olefin polymer membrane used in the present invention is not particularly limited insofar as immunoglobulin monomers can be sufficiently separated from immunoglobulin dimers. The lower limit of the molecular weight cut-off of the olefin polymer membrane is 100,000 or more, preferably 150,000 or more, and more preferably 250,000 or more. The upper limit of the molecular weight cut-off of the olefin polymer membrane is 500,000 or less, preferably 450,000 or less, and more preferably 400,000 or less. If the molecular weight cut-off of the olefin polymer membrane is less than 100,000, the amount of immunoglobulin that passes through the membrane decreases. If the molecular weight cut-off of the olefin polymer membrane is more than 500,000, immunoglobulin monomers and immunoglobulin dimers pass through the membrane (i.e., the fractionation performance decreases).

In the present invention, the molecular weight cut-off is calculated as a molecular weight that provides a blocking rate of 90% based on the correlation between molecular weight and blocking rate when performing dead-end filtration using a protein such as albumin (66,000), γ-globulin (160,000), catalase (232,000), ferritin (440,000), thyroglobulin (669,000), PEG, dextran, or the like.

A method of producing the olefin polymer membrane used in the present invention is not particularly limited. For example, a melt membrane-forming method may be used to produce the olefin polymer membrane. The melt membrane-forming method includes uniformly mixing a membrane material and a plasticizer by heating, causing phase separation by cooling, and extracting the plasticizer from the resulting membrane film to obtain a membrane.

A typical melt membrane-forming method used to produce the olefin polymer membrane used in the present invention includes the following steps (a) to (c).

(a) A composition containing the olefin polymer and the plasticizer is heated to a temperature equal to or higher than the crystalline melting point of the olefin polymer to effect uniform dissolution, and the composition is discharged from a discharge port to form a membrane.

(b) A nonvolatile liquid that partially dissolves the olefin polymer is caused to come in contact with one of the surfaces of the membrane at 100° C. or more, and the other surface of the membrane is cooled while withdrawing the membrane at a withdrawing speed so that the draft ratio defined by the following formula (9) is 1 to 15.

Draft ratio=(membrane withdrawing speed)/(composition discharge speed at discharge port)    (9)

(c) The plasticizer and the nonvolatile liquid are substantially removed.

The lower limit of the polymer concentration employed in the melt membrane-forming method used to obtain the olefin polymer membrane used in the present invention is 20 to 90 wt %, preferably 30 to 80 wt %, and most preferably 35 to 70 wt %, based on the composition containing the olefin polymer and the plasticizer. If the polymer concentration is less than 20 wt %, membrane formability may deteriorate, or a membrane having a sufficient mechanical strength may not be obtained. If the polymer concentration is more than 90 wt %, the pore size of the resulting olefin polymer membrane may decrease to a large extent. Moreover, the filtration speed may decrease to an impractical level due to a decrease in porosity.

As the plasticizer used in the melt membrane-forming method used to obtain the olefin polymer membrane used in the present invention, a nonvolatile solvent that can form a homogeneous solution at a temperature equal to or higher than the crystalline melting point of the resin when mixed with the olefin polymer to achieve a composition that produces the olefin polymer membrane is used. The term "nonvolatile solvent" used herein refers to a solvent having a boiling point of 250° C. or more under atmospheric pressure. The plasticizer may be liquid or solid at room temperature (approximately 20° C.). A solid-liquid phase separation-type plasticizer that has a thermally induced solid-liquid phase separation point at a temperature equal to or higher than room temperature when cooling a homogeneous solution of the plasticizer and the olefin polymer, may also be used. Some plasticizers have a thermally induced liquid-liquid phase separation point at a temperature equal to or higher than room temperature when cooling a homogeneous solution of the plasticizer and the olefin polymer. When using such a liquid-liquid phase separation-type plasticizer, the resulting olefin polymer membrane may have large pores. The plasticizer may be a single substance, or a mixture of a plurality of substances.

The thermally induced solid-liquid phase separation point may be determined by measuring the exothermic peak temperature of a sample prepared by melt-mixing a composition that includes the olefin polymer and the plasticizer and has a given concentration by thermal analysis such as differential scanning calorimetry (DSC). The crystallization point of the resin may be similarly determined by thermal analysis using a sample prepared by melt-mixing the resin.

In the present invention, the plasticizer disclosed in WO01/28667 may be used. Specifically, it is preferable to use a plasticizer of which the depression constant of the phase separation point a of the composition defined by the following formula (10) is 0 to 40° C., preferably 1 to 35° C. or more, and more preferably 5 to 30° C. If the depression constant of the phase separation point is more than 40° C., the pore diameter homogeneity and the strength of the membrane decrease.

$$\alpha = 100 \times (T_c^0 - T_c) \div (100 - C) \quad (10)$$

$\alpha$: depression constant of the phase separation point (° C.)
$T_c^0$: crystallization temperature (° C.) of olefin polymer
$T_c$: thermally induced solid-liquid phase separation point (° C.) of composition
C: concentration (wt %) of olefin polymer in composition As the plasticizer, a phthalate, an adipate, or a sebacate of which the carbon chain length of the ester chain is seven or less, a phosphate or a citrate of which the carbon chain length of the ester chain is eight or less, or the like may be suitably used. It is particularly preferable to use diheptyl phthalate, dicyclohexyl phthalate, dibutyl phthalate, diethyl phthalate, dimethyl phthalate, dibutyl adipate, dibutyl sebacate, triphenyl phosphate, tricresyl phosphate, diphenyl cresyl phosphate, tri(2-ethylhexyl)phosphate, tributyl phosphate, acetyl tributyl citrate, or the like as the plasticizer.

If necessary, additives such as an antioxidant, a nucleating agent, an antistatic agent, a flame retardant, a lubricant, and a UV absorber may be added to the composition used in the present invention insofar as the performance of the resulting membrane is not adversely affected.

The first method that obtains a homogeneous solution of a composition containing the olefin polymer and the plasticizer in the melt membrane-forming method used to obtain the olefin polymer membrane used in the present invention includes introducing the resin into a continuous resin mixer (e.g., extruder), introducing the plasticizer in an arbitrary ratio while melting the resin by heating, and mixing the mixture using a screw to obtain a homogeneous solution. The resin may be a powder, granules, or pellets. It is preferable that the plasticizer be liquid at room temperature when using the first method. As the extruder, a single-screw extruder, a counter-rotating twin-screw extruder, a co-rotating twin-screw extruder, or the like may be used.

The second method that obtains a homogeneous solution of a composition containing the olefin polymer and the plasticizer includes mixing and dispersing the olefin polymer and the plasticizer beforehand using a stirrer (e.g., Henschel mixer), introducing the resulting composition into a continuous resin mixer (e.g., extruder), and melt-mixing the composition to obtain a homogeneous solution. The composition may be in the form of a slurry when the plasticizer is liquid at room temperature, and may be in the form of a powder, granules, or the like when the plasticizer is solid at room temperature.

The third method that obtains a homogeneous solution of a composition containing the olefin polymer and the plasticizer includes melt-mixing the composing using a simple resin mixer (e.g., Brabender mixer or mill) or a batch-type mixer. The third method is not necessarily productive due to the batch operation, but is convenient and highly flexible.

In the melt membrane-forming method used to obtain the olefin polymer membrane used in the present invention, a composition containing the olefin polymer and the plasticizer is heated to a temperature equal to or higher than the crystalline melting point of the olefin polymer to obtain a homogeneous solution, the solution is extruded into a flat membrane or a hollow fiber membrane from a discharge port of a T-die, a circular die, or a circular spinneret (step (a)), and the extruded product is cooled and solidified (step (b)) to form a membrane structure.

In the melt membrane-forming method used to obtain the olefin polymer membrane used in the present invention, the homogeneous solution of the composition containing the olefin polymer and the plasticizer obtained by heating is discharged from the discharge port, and is withdrawn at a withdrawing speed so that the draft ratio defined by the following formula (11) is 1 to 15 while causing a nonvolatile liquid that partially dissolves the olefin polymer to come in contact with the olefin polymer to form a membrane.

$$\text{Draft ratio} = (\text{membrane withdrawing speed})/(\text{composition discharge speed at discharge port}) \quad (11)$$

The draft ratio is 1.5 or more, and preferably 2 or more, but 10 or less, and preferably 7 or less. If the draft ratio is less than 1, tension is not applied to the membrane so that formability decreases. If the draft ratio is more than 15, the membrane is stretched so that it is difficult to form a coarse structure layer having a sufficient thickness.

The discharge speed of the composition from the discharge port is defined by the following formula (12).

$$\text{Discharge speed of composition from discharge port} = (\text{volume of composition discharged per unit time})/(\text{area of discharge port}) \quad (12)$$

The discharge speed is 1 m/min or more, and preferably 3 m/min or more, but 60 m/min or less, and preferably 40 m/min or less. If the discharge speed is less than 1 m/min, productivity decreases. Moreover, the discharge amount changes to a large extent. If the discharge speed exceeds 60 m/min, a turbulent flow may occur at the discharge port due to a large discharge amount (i.e., the discharge state may become unstable). The withdrawing speed may be set corresponding to the discharge speed. The withdrawing speed is 1 m/min or more, and preferably 3 in/min or more, but 200 m/min or less, and preferably 150 m/min or less. If the withdrawing speed is less than 1 in/min, productivity and formability decrease. If the withdrawing speed exceeds 200 in/min, the membrane tends to break due to a decrease in cooling time and an increase in tension applied to the membrane.

In the present invention, an extraction solvent is used to remove the plasticizer. It is preferable that the extraction solvent be a poor solvent for the olefin polymer and a good solvent for the plasticizer, and have a boiling point higher than the melting point of the olefin polymer membrane. Examples of the extraction solvent include hydrocarbons such as hexane and cyclohexane, halogenated hydrocarbons such as methylene chloride and 1,1,1-trichloroethane, alcohols such as ethanol and isopropanol, ethers such as diethyl ether and tetrahydrofuran, ketones such as acetone and 2-butanone, and water.

In the present invention, the first method that removes the plasticizer includes immersing the olefin polymer membrane cut to given dimensions in a container that contains the extraction solvent, sufficiently washing the olefin polymer membrane with the extraction solvent, and air-drying the solvent adhering to the olefin polymer membrane, or drying the solvent by applying a hot air blast. It is preferable to repeat the immersion operation and the washing operation a number of times so that the amount of the plasticizer that remains in the olefin polymer membrane decreases. It is preferable to hold the ends of the olefin polymer membrane in order to suppress shrinkage of the olefin polymer membrane during the immersion operation, the washing operation, and the drying operation.

The second method that removes the plasticizer includes continuously introducing the olefin polymer membrane into a bath filled with the extraction solvent, immersing the olefin polymer membrane in the bath for a period of time sufficient to remove the plasticizer, and drying the solvent adhering to the olefin polymer membrane. The extraction efficiency can be improved by sequentially introducing the olefin polymer membrane baths that differ in concentration of the extraction solvent (multi-stage method), or supplying the extraction solvent in the direction opposite to the travel direction of the olefin polymer membrane to form a concentration gradient (counter-flow method), for example.

In the first and second methods, it is important to substantially remove the plasticizer from the olefin polymer membrane. The expression "substantially remove" means removing the plasticizer from the olefin polymer membrane to such an extent that the performance of the separation membrane is not adversely affected. The amount of the plasticizer that remains in the olefin polymer membrane is preferably 1 wt % or less, and more preferably 100 ppm by weight or less. The amount of the plasticizer that remains in the olefin polymer membrane may be determined by gas chromatography, liquid chromatography, or the like. Diffusion of the plasticizer and the solvent can be promoted by heating the extraction solvent to a temperature lower than the boiling point of the extraction solvent (preferably by 5° C. or less).

In the present invention, if the olefin polymer membrane is heated before, after, or before and after removing the plasticizer, shrinkage of the olefin polymer membrane when removing the plasticizer can be suppressed, and the strength and the heat resistance of the olefin polymer membrane can be improved. The olefin polymer membrane may be heated applying a hot air blast to the olefin polymer membrane, immersing the olefin polymer membrane in a heat medium, or causing the olefin polymer membrane to come in contact with a heated metal roll or the like. It is preferable to heat the olefin polymer membrane while fixing the dimensions of the olefin polymer membrane in order to prevent clogging of minute pores. The heating temperature is preferably equal to or lower than the melting point of the olefin polymer. When using polyethylene, the heating temperature is 60° C. or more, and preferably 65° C. or more, but 100° C. or less, and preferably 95° C. or less. If the heating temperature is higher than the melting point of the olefin polymer, the membrane may break during heating, or the pores in the membrane may be crushed. The drying time is determined based on the drying temperature. The drying time is generally 0.01 to 48 hours.

The vinyl alcohol polymer used in the present invention is a copolymer (including a block copolymer and a graft copolymer) obtained by copolymerizing polyvinyl alcohol or a modified polyvinyl alcohol (e.g., partially acetalized polyvinyl alcohol) with ethylene, propylene, vinylpyrrolidone, vinyl chloride, vinyl fluoride, methyl methacrylate, acrylonitrile, itaconic acid, or the like, or a derivative thereof. Among these, an ethylene-vinyl alcohol copolymer is preferable.

The degree of saponification of the vinyl alcohol polymer used in the present invention is 80 mol % or more, and preferably 85 mol % or more. The degree of saponification of the vinyl alcohol polymer is 100 mol % or less, and preferably 95 mol % or less.

The polyvinyl alcohol content in the vinyl alcohol polymer chain used in the present invention is preferably 30 wt % or more, and more preferably 50 wt % or more. If the polyvinyl alcohol content is less than 30 wt %, the hydrophilicity of the membrane decreases, for example.

The vinyl alcohol polymer membrane used in the present invention is mainly formed of a vinyl alcohol polymer. The vinyl alcohol polymer membrane may contain other polymer substances and additives insofar as the characteristics of the vinyl alcohol polymer are not adversely affected. These polymers may be used in combination.

The lower limit of the weight average molecular weight of the vinyl alcohol polymer used in the present invention is 5,000 or more, preferably 10,000 or more, and particularly preferably 50,000 or more. The upper limit is 2,000,000 or less, preferably 900,000 or less, and particularly preferably 800,000 or less. It is normally difficult to measure the molecular weight of a resin having an average molecular weight of more than 1,000,000 by GPC. In this case, a viscosity average molecular weight measured by viscometry may be used. If the average molecular weight of the vinyl alcohol polymer is less than 5000, the mechanical strength of the membrane decreases. If the average molecular weight of the vinyl alcohol polymer is more than 2,000,000, uniform melt-mixing becomes difficult.

In the present invention, an additional treatment may be performed insofar as the vinyl alcohol polymer membrane is not adversely affected. Examples of the additional treatment include cross-linking, introduction of a functional group due to chemical surface modification, and the like.

The molecular weight cut-off of the vinyl alcohol polymer membrane used in the present invention is not particularly limited insofar as immunoglobulin monomers can be sufficiently separated from immunoglobulin dimers. The lower limit of the molecular weight cut-off of the vinyl alcohol polymer membrane is 100,000 or more, preferably 150,000 or more, and more preferably 250,000 or more. The upper limit of the molecular weight cut-off of the vinyl alcohol polymer membrane is 500,000 or less, preferably 450,000 or less, and more preferably 400,000 or less. If the molecular weight cut-off of the vinyl alcohol polymer membrane is less than 100,000, the amount of immunoglobulin that passes through the membrane decreases. If the molecular weight cut-off of the vinyl alcohol polymer membrane is more than 500,000, immunoglobulin monomers and immunoglobulin dimers pass through the membrane (i.e., the fractionation performance decreases).

In the present invention, the molecular weight cut-off is calculated as a molecular weight that provides a blocking rate of 90% based on the correlation between molecular weight and blocking rate when performing dead-end filtration using a protein such as albumin (66,000), γ-globulin (160,000), catalase (232,000), ferritin (440,000), thyroglobulin (669,000), PEG, dextran, or the like.

A method of producing the vinyl alcohol polymer membrane used in the present invention is not particularly limited. For example, a wet membrane-forming method may be used to produce the vinyl alcohol polymer membrane. The wet membrane-forming method is a method that obtains a membrane by causing a membrane raw material solution in which a membrane material is dissolved in a good solvent to come in contact with a coagulation liquid (solvent) that is miscible with the good solvent in the membrane raw material solution, but is not mutually soluble with the membrane material so that concentration-induced phase separation occurs from the contact surface.

The good solvent used in the wet membrane-forming method to obtain the vinyl alcohol polymer membrane used in the present invention preferably dissolves the vinyl alcohol polymer (membrane material) in an amount of 5 wt % or more. Examples of the good solvent include water, alcohols, dimethyl sulfoxide, N,N-dimethylformamide, N,N-dimethylacetamide, N-methyl-2-pyrrolidone, and the like. These solvents may be used either individually or in combination. It is most preferable to use water from an industrial point of view. Boric acid that promotes coagulation, a surfactant that improves membrane formation stability, an anti-foaming agent, and the like may also be appropriately added.

The membrane raw material solution used in the wet membrane-forming method to obtain the vinyl alcohol polymer membrane according to the present invention is not particularly limited insofar as a vinyl alcohol polymer membrane having the desired structure and performance can be produced. A solution in which the vinyl alcohol polymer and a pore-forming agent are dissolved in a common solvent is normally used as the pore-forming agent. The membrane formability is improved as the concentration of the vinyl alcohol polymer in the membrane raw material solution increases. On the other hand, the porosity of the membrane decreases as the concentration of the vinyl alcohol polymer increases so that water permeability tends to decrease. The vinyl alcohol polymer is used in an amount of 2 wt % or more, preferably 5 wt % or more, and particularly preferably 10 wt % or more, based on the membrane raw material solution (=100 wt %). The upper limit of the concentration of the vinyl alcohol polymer is 50 wt % or less, preferably 40 wt % or less, and particularly preferably 30 wt % or less. A solution in which the vinyl alcohol polymer is homogeneously dissolved is preferably used.

In the wet membrane-forming method used to obtain the vinyl alcohol polymer membrane according to the present invention, the lower limit of the temperature of the membrane raw material solution is 0° C. or more, preferably 10° C. or more, and particularly preferably 25° C. or more. The upper limit of the temperature of the membrane raw material solution is preferably equal to or less than the boiling point of the good solvent contained in the membrane raw material solution. If the temperature of the membrane raw material solution is within the above range, a viscosity suitable for producing a membrane can be obtained.

If necessary, additives such as an antioxidant, a nucleating agent, an antistatic agent, a flame retardant, a lubricant, and a UV absorber may be added to the membrane raw material solution used in the present invention insofar as the performance of the resulting membrane is not adversely affected.

Examples of the pore-forming agent used in the wet membrane-forming method to obtain the vinyl alcohol polymer membrane used in the present invention include glycols such as polyethylene glycol having an average molecular weight of 200 to 4,000,000, polypropylene glycol, tetraethylene glycol, triethylene glycol, and ethylene glycol, alcohols such as methanol, ethanol, and propanol, polyhydric alcohols such as glycerol and butanediol, esters such as ethyl lactate and butyl lactate, and the like. These compounds are used either individually or in combination.

In the present invention, the amount of the pore-forming agent is appropriately changed corresponding to the type of the vinyl alcohol polymer and the type of the pore-forming agent. It is preferable to use the pore-forming agent in such an amount that the membrane raw material solution has the upper critical solution point described later. The upper critical solution point refers to a temperature at which a solution changes from a transparent solution to a cloudy solution when adjusting the membrane raw material solution to a transparent, uniform state at a high temperature and gradually decreasing the temperature of the membrane raw material solution. The upper critical solution point is synonymous with a whitening point or a cloud point.

The hydrophilic polymer used in the wet membrane-forming method used to obtain the vinyl alcohol polymer membrane according to the present invention mainly promotes formation of a porous structure of an outer porous support layer, and increases the viscosity of the membrane raw material solution. The molecular weight and the amount of the hydrophilic polymer added to the membrane raw material solution may be appropriately adjusted so that a membrane is stably formed. If the viscosity of the membrane raw material solution is low, breakage of the membrane may occur during production (i.e., the membrane may not be stably formed). If the viscosity of the membrane raw material solution is too high, the outer porous support layer may not be sufficiently formed (grown) so that the porosity of the outer-layer porous structure may become insufficient. As a result, a membrane having high permeability may not be obtained. Moreover, the membrane raw material solution discharged from the spinneret is feared to undergo a melt fracture phenomenon due to an increase in the viscosity of the membrane raw material solution.

In the wet membrane-forming method used to obtain the vinyl alcohol polymer membrane according to the present invention, the upper limit value of the concentration of the hydrophilic polymer in the membrane raw material solution is appropriately determined based on the type and the molecular weight of the hydrophilic polymer. The upper limit value of the concentration of the hydrophilic polymer is normally 40 wt % or less, and preferably 30 wt % or less.

The coagulation liquid used in the wet membrane-forming method to obtain the vinyl alcohol polymer membrane according to the present invention is not particularly limited insofar as the coagulation liquid causes concentration-induced phase separation when coming in contact with the membrane raw material solution and forms a membrane from the contact surface. Examples of an aqueous coagulant include purified water, an aqueous solution of a dehydrating salt such as sodium sulfate, an aqueous solution of an alkaline substance such as sodium hydroxide or aqueous ammonia, and the like. These compounds may be used either individually or in combination. Further examples of the coagulation liquid include methanol, ethanol, propanol, and the like. Examples of the polyol solvent include organic coagulants that cause coagulation of the vinyl alcohol polymer, such as ethylene glycol, diethylene glycol, triethylene glycol, tetraethylene glycol, glycerol, propylene glycol, 1,2-butanediol, 1,4-butanediol, and the like. The polyol solvent may be used in combination with water. A water-soluble polymer such as polyvinyl alcohol, polyethylene glycol, polypropylene glycol, polyethylene oxide, a polyethylene glycol-polypropylene glycol block copolymer, polyacrylamide, polyvinylpyrrolidone, polyhydroxy acrylate, polyhydroxy methacrylate, polyacrylic acid, polymethacrylic acid, polyitaconic acid, polyfumaric acid, polycitraconic acid, poly-p-styrene sulfonic acid, sodium poly-p-styrene sulfonate, N,N-dimethylacrylamide, carboxymethylcellulose, starch, corn starch, polychitosan, or polychitin may be added to the coagulation liquid. The filtration performance of the membrane can be improved by adding such a water-soluble polymer, although the improvement effect varies depending on the molecular weight and the amount of the water-soluble polymer. It is also possible to add a good solvent such as N-methyl-2-pyrrolidone, N,N-dimethylacetamide, dimethyl sulfoxide, N,N-dimethylformamide, or γ-butyrolactone to the coagulation liquid. When using a coagulation liquid that contains a good solvent and a non-solvent, the concentration of the good solvent in the coagulation liquid (=100 wt %) is preferably 90 wt % or more, although the composition varies depending on the composition of the membrane raw material solution, the contact temperature of the membrane raw material solution and the coagulation liquid, and the like. If the concentration of the good solvent is within the above range, concentration-induced phase separation sufficient to form a membrane occurs.

The coagulation liquid that is passed through a fiber when producing a hollow fiber membrane (hereinafter referred to as "internal coagulation liquid") using the wet membrane-forming method used to obtain the vinyl alcohol polymer membrane according to the present invention may be a solution similar to the external coagulation liquid, or an organic solvent (e.g., hexane or liquid paraffin) that does not cause coagulation of the vinyl alcohol polymer and is not miscible with the solvent of the membrane raw material solution. It is also possible to use a dry-and-wet membrane-forming method that introduces a gas such as air, nitrogen, or ammonia gas.

The membrane-forming temperature in the wet membrane-forming method used to produce the vinyl alcohol polymer membrane according to the present invention refers to a temperature at which the membrane raw material solution is caused to come in contact with the coagulation liquid so that concentration-induced phase separation occurs. The lower limit of the membrane-forming temperature is 0° C. or more, preferably 10° C. or more, and particularly preferably 25° C. or more. The upper limit of the membrane-forming temperature is equal to or less than the boiling point of the membrane raw material solution or the coagulation liquid, preferably a temperature lower than the boiling point of the membrane raw material solution or the coagulation liquid by 5° C. or more, and particularly preferably a temperature lower than the boiling point of the membrane raw material solution or the coagulation liquid by 10° C. or more. The membrane-forming temperature is determined by the temperature of a double spinneret when producing a hollow fiber membrane. The membrane-forming temperature is determined by the temperature of the coagulation liquid when producing a flat membrane.

It is desirable to remove dissolved gas from the membrane raw material solution and the coagulation liquid (particularly a coagulation liquid that is passed through a fiber when producing a hollow fiber membrane) used in the wet membrane-forming method to obtain the vinyl alcohol polymer membrane according to the present invention after homogeneously dissolving each component. Defects of the membrane due to foaming of the dissolved gas can be significantly suppressed by removing the dissolved gas. In particular, removal of oxygen reduces an oxidation reaction of a material during membrane processing at a high temperature. This step may be omitted when gas is not dissolved in the membrane raw material solution, the coagulation liquid, and the internal coagulation liquid. This step is omitted when using a gas such as air, nitrogen, or ammonia gas as the coagulation agent (i.e., dry-and-wet membrane-forming method).

When producing a hollow fiber membrane using the wet membrane-forming method used to produce the vinyl alcohol polymer membrane according to the present invention, in order to allow the membrane raw material solution discharged from a double spinneret to promptly coagulate due to the internal coagulation liquid, a bath (hereinafter referred to as "coagulation bath") may be provided directly under the spinneret, and the membrane raw material solution may be caused to come in contact with a coagulation liquid (hereinafter referred to as "external coagulation liquid") provided in the coagulation bath.

When producing a hollow fiber membrane using the wet membrane-forming method used to produce the vinyl alcohol polymer membrane according to the present invention, the distance from the spinneret to the liquid surface of the external coagulation liquid (hereinafter referred to as "air gap distance") and the temperature and the humidity in the space from the spinneret to the liquid surface of the external coagulation liquid may be adjusted in order to arbitrarily control the cross-sectional structure of the hollow fiber membrane (e.g., uniform structure or non-uniform structure). For example, the lower limit of the air gap distance is 0.001 m or more, preferably 0.005 m or more, and particularly preferably 0.01 m or more, and the upper limit of the air gap distance is 2.0 m or less, preferably 1.5 m or less, and particularly preferably 1.2 m or less. The lower limit of the temperature in the space from the spinneret to the liquid surface of the external coagulation liquid is 10° C. or more, preferably 20° C. or more, and particularly preferably 25° C. or more. The lower limit of the humidity in the space from the spinneret to the liquid surface of the external coagulation liquid is 0% or more, preferably 10% or more, and particularly preferably 30% or more, and the upper limit of the humidity is 100% or less, although the humidity varies depending on the temperature.

The take-up speed when producing a hollow fiber membrane using the wet membrane-forming method according to the present invention is generally 300 m/h to 9,000 m/h, although the take-up speed varies depending on the production conditions, the shape of the spinneret, the composition of the spinning raw solution, the compositions of the internal coagulation liquid and the external coagulation liquid, the temperatures of the raw solution and the coagulation liquids, and the like.

In the wet membrane-forming method used to produce the vinyl alcohol polymer membrane according to the present invention, a treatment such as stretching, neutralization, washing with water, a wet-heat treatment, substitution with ammonium sulfate, or drying, may be performed after coagulation with the coagulation liquid. It is possible to accelerate solvent removal by immersing the membrane in a solvent removal liquid in order to increase the strength of the membrane. The solvent removal liquid is a liquid that can remove the solvent remaining after concentration-induced phase separation using the coagulation liquid. Any solvent may be used insofar as the membrane is not dissolved. Water, ethanol, or the like is generally used. It is also possible to perform a modification such as acetalization using a monoaldehyde and/or polyaldehyde such as formaldehyde, glutaraldehyde, benzaldehyde, glyoxal, or nonanedial, esterification, or etherification, or crosslinking using a methylol compound and a polyisocyanate. These treatments may be performed either individually or in combination. A hot stretching and/or heat treatment may be performed after spinning, or the above modification may be performed after the hot stretching and/or heat treatment.

An undried vinyl alcohol polymer membrane obtained by the wet membrane-forming method according to the present invention is dried at a temperature at which breakage of the membrane does not occur (e.g., a temperature between 20° C. and a temperature equal to or lower than the melting point of the vinyl alcohol polymer). The drying temperature is preferably 30 to 80° C. The drying time is determined based on the drying temperature. The drying time is generally 0.01 to 48 hours.

The degree of hydrophilicity of the vinyl alcohol polymer membrane according to the present invention may be evaluated by the contact angle. It is preferable that the average value of the advancing contact angle and the receding contact angle at 25° C. be 60 degree or less, more preferably 45 degree or less, and still more preferably 30 degree or less. If water voluntarily permeates the pores in the vinyl alcohol polymer membrane when causing the olefin polymer membrane to come in contact with water, the vinyl alcohol polymer membrane may be determined to have sufficient hydrophilicity.

The cellulose polymer membrane used in the present invention is mainly formed of a cellulose polymer. The cellulose polymer membrane may contain other polymer substances and additives insofar as the characteristics of the cellulose polymer are not adversely affected. These polymers may be used in combination.

Examples of the cellulose polymer used in the present invention include cellulose ester compounds such as cuprammonium regenerated cellulose, cellulose diacetate, cellulose triacetate, cellulose propionate, cellulose butyrate, and cellulose phenyl carbanilate, cellulose ethers such as methyl cellulose and ethyl cellulose, blend compounds thereof, and the like. Among these, cuprammonium regenerated cellulose is preferable.

The lower limit of the weight average molecular weight of the cellulose polymer used in the present invention is 5,000 or more, preferably 10,000 or more, and particularly preferably 50,000 or more. The upper limit of the weight average molecular weight of the cellulose polymer is 1,000,000 or less, preferably 900,000 or less, and particularly preferably 800,000 or less. If the weight average molecular weight of the cellulose polymer is within the above range, the cellulose polymer exhibits sufficient strength and membrane formability.

The molecular weight cut-off of the cellulose polymer membrane used in the present invention is not particularly limited insofar as immunoglobulin monomers can be sufficiently separated from immunoglobulin dimers. The lower limit of the molecular weight cut-off of the cellulose polymer membrane is 100,000 or more, preferably 150,000 or more, and more preferably 250,000 or more. The upper limit is 500,000 or less, preferably 450,000 or less, and more preferably 400,000 or less. If the molecular weight cut-off of the cellulose polymer membrane is less than 100,000, the amount of immunoglobulin that passes through the membrane decreases. If the molecular weight cut-off of the cellulose polymer membrane is more than 500,000, immunoglobulin monomers and immunoglobulin dimers pass through the membrane (i.e., the fractionation performance decreases).

In the present invention, the molecular weight cut-off is calculated as a molecular weight that provides a blocking rate of 90% based on the correlation between molecular weight and blocking rate when performing dead-end filtration using a protein such as albumin (66,000), γ-globulin (160,000), catalase (232,000), ferritin (440,000), thyroglobulin (669,000), PEG, dextran, or the like.

A method of producing the cellulose polymer hollow fiber membrane according to the present invention is not particularly limited. For example, a spinning raw solution is discharged from an outer spinneret of a circular double spinneret while discharging an internal coagulation liquid (i.e., a microphase separation/coagulation liquid for the spinning raw solution) from a center spinneret of the circular double spinneret so that the spinning raw solution and the coagulation liquid are introduced into a spinning tube. The spinning tube is a tube that is directly connected to the spinneret. The spinning tube is filled with an external coagulation liquid so that the spinning raw solution comes in contact with the external coagulation liquid immediately after discharge. The external coagulation liquid is regularly supplied to the spinning tube, and flows down through a descending tube together with the spinning raw solution. Particles are thus formed by microphase separation, and a three-dimensional membrane structure is obtained to complete a porous membrane structure.

The good solvent used in the wet membrane-forming method to obtain the cellulose polymer membrane according to the present invention is not particularly limited insofar as the good solvent dissolves the cellulose polymer. Examples of the good solvent include a cuprammonium solution and the like.

The membrane raw material solution used in the wet membrane-forming method to obtain the cellulose polymer membrane according to the present invention is not particularly limited insofar as a cellulose polymer membrane having the desired structure and performance can be produced. The membrane formability is improved as the concentration of the cellulose polymer in the membrane raw material solution increases. On the other hand, the porosity of the membrane decreases as the concentration of the cellulose polymer increases so that water permeability tends to decrease. The cellulose polymer is used in an amount of 2 wt % or more, preferably 5 wt % or more, and particularly preferably 10 wt % or more, based on the membrane raw material solution (=100 wt %). The upper limit of the concentration of the cellulose polymer is 25 wt % or less, preferably 20 wt % or less, and particularly preferably 15 wt % or less. A solution in which the cellulose polymer is homogeneously dissolved is preferably used. If the cellulose concentration is less than 2 wt %, the resulting hollow fiber membrane may have insufficient mechanical properties. If the cellulose concentration is more than 25 wt %, it may be difficult to prepare the spinning solution and perform the spinning operation.

The lower limit of the temperature of the membrane raw material solution according to the present invention is 0° C. or more, preferably 10° C. or more, and particularly preferably 25° C. or more. The upper limit of the temperature of the membrane raw material solution is preferably equal to or less than the boiling point of the good solvent contained in the membrane raw material solution. If the temperature of the membrane raw material solution is within the above range, a viscosity suitable for producing a membrane can be obtained.

If necessary, additives such as an antioxidant, a nucleating agent, an antistatic agent, a flame retardant, a lubricant, and a UV absorber may be added to the membrane raw material solution used in the present invention insofar as the performance of the resulting membrane is not adversely affected.

The coagulation liquid used in the wet membrane-forming method to obtain the cellulose polymer membrane according to the present invention is not particularly limited insofar as the coagulation liquid causes concentration-induced phase separation when coming in contact with the membrane raw material solution and forms a membrane from the contact surface. Examples of the coagulant include a liquid that does not coagulate or coagulate to only a small extent due to the spinning solution, such as purified water, water, tetrachloroethylene, trichloroethylene, trichlorotrifluoroethane, methanol, ethanol, propanol, acetone, methyl ethyl ketone, sodium hydroxide, sulfuric acid, ammonium sulfate, formic acid, acetic acid, propionic acid, glycerol, and polyethylene glycol. The coagulant is appropriately selected depending on the type of the spinning solution. A solution containing at least coagulation liquid selected from these coagulation liquids, or a mixture of these coagulation liquids is preferably used. It is preferable to use a mixed solution of acetone, ammonia, and water.

The internal coagulation liquid and the external coagulation liquid used in the wet membrane-forming method to obtain the cellulose polymer membrane according to the present invention may be the same or different.

The cellulose polymer membrane according to the present invention may be produced using a dry-and-wet membrane-forming method that utilizes a gas such as air, nitrogen, carbon dioxide, argon, oxygen, flon gas (e.g., tetrafluoromethane or hexafluoroethane), or a halogen gas.

The membrane-forming temperature in the wet membrane-forming method used to produce the cellulose polymer membrane according to the present invention refers to a temperature at which the membrane raw material solution is caused to come in contact with the coagulation liquid so that concentration-induced phase separation occurs. The lower limit of the membrane-forming temperature is 0° C. or more, preferably 10° C. or more, and particularly preferably 25° C. or more. The upper limit of the membrane-forming temperature is equal to or less than the boiling point of the membrane raw material solution or the coagulation liquid, preferably a temperature lower than the boiling point of the membrane raw material solution or the coagulation liquid by 5° C. or more, and particularly preferably a temperature lower than the boiling point of the membrane raw material solution or the coagulation liquid by 10° C. or more. The membrane-forming temperature is determined by the temperature of a double spinneret when producing a hollow fiber membrane. The membrane-forming temperature is determined by the temperature of the coagulation liquid when producing a flat membrane.

It is desirable to remove dissolved gas from the membrane raw material solution and the coagulation liquid (particularly the internal coagulation liquid that is caused to flow through a fiber when producing a hollow fiber membrane) used in the wet membrane-forming method to obtain the cellulose polymer membrane according to the present invention after homogeneously dissolving each component. Defects of the membrane due to foaming of the dissolved gas can be significantly suppressed by removing the dissolved gas. In particular, removal of oxygen reduces an oxidation reaction of a material during membrane processing at a high temperature. This step may be omitted when gas is not dissolved in the membrane raw material solution, the coagulation liquid, and the internal coagulation liquid. This step is omitted when using a gas such as air, nitrogen, or ammonia gas as the coagulation agent (i.e., dry-and-wet membrane-forming method).

In the wet membrane-forming method used to obtain the cellulose polymer membrane according to the present invention, the spinning raw solution may be introduced into the external coagulation liquid after traveling over an air gap distance from the spinneret to the liquid surface of the external coagulation liquid, or may be directly introduced into the external coagulation liquid. The air gap distance is preferably set so that the spinning raw solution linearly enters the external coagulation liquid. The air gap distance is 0.5 m or less, preferably 0.2 m or less, and particularly preferably 0.1 m or less. Formability deteriorates as the air gap distance increases so that the shape of the hollow fibers may not be maintained.

The lower limit of the temperature in the air gap is 10° C. or more, preferably 20° C. or more, and particularly preferably 25° C. or more. The lower limit of the humidity in the air gap is 0% or more, preferably 10% or more, and particularly preferably 30% or more, and the upper limit of the humidity is 100% or less, although the humidity varies depending on the temperature.

The spinning raw solution is shaped into a hollow fiber membrane when the spinning raw solution flows through the descending tube. The hollow fiber membrane is withdrawn through the opening of an ascending tube, and wound.

The take-up speed when producing a hollow fiber membrane using the wet membrane-forming method used to produce the cellulose polymer membrane according to the present invention varies depending on the production conditions, the shape of the spinneret, the composition of the spinning raw solution, the compositions of the internal coagulation liquid and the external coagulation liquid, the temperatures of the raw solution and the coagulation liquids, and the like. The lower limit of the take-up speed is 100 m/h or more, and preferably 200 m/h or more, and the upper limit of the take-up speed is 1,000 m/h or less, and preferably 500 m/h or less.

In the wet membrane-forming method used to produce the cellulose polymer membrane according to the present invention, it is possible to accelerate removal of the solvent after coagulation with the coagulation liquid by immersing the membrane in a solvent removal liquid in order to increase the strength of the membrane. The solvent removal liquid is a liquid that can remove the solvent remaining after concentration-induced phase separation using the coagulation liquid. Any solvent may be used insofar as the membrane is not dissolved. Water, ethanol, or the like is generally used.

An undried cellulose polymer membrane obtained by the wet membrane-forming method according to the present invention is dried at a temperature at which breakage of the membrane does not occur (e.g., a temperature between 20° C. and a temperature equal to or lower than the melting point of the cellulose polymer). The lower limit of the drying temperature is 30° C. or more, and preferably 40° C. or more. The upper limit of the drying temperature is 80° C. or less, and preferably 70° C. or less. The drying time is determined based on the drying temperature. The drying time is generally 0.01 to 48 hours. The membrane may be refined using water and an inorganic salt aqueous solution, and dried after applying a known pore-diameter-holding agent such as glycerol or polyethylene glycol.

In the present invention, if the flow rate of the external coagulation liquid inside the spinning tube (external coagulation liquid speed) is much lower than the take-up speed, stretching occurs inside the spinning tube. In the present invention, the difference between the speed of the external coagulation liquid and the take-up speed is preferably 20% or less.

It is preferable that the speed of the external coagulation liquid be high in order to reduce the bath resistance in the coagulation bath. However, if the speed of the external coagulation liquid is too high, the hollow fiber membrane swings to a large extent so that spinning becomes difficult. Therefore, it is necessary to appropriately set the speed of the external coagulation liquid. It is most preferable to select the maximum flow rate within the range in which the hollow fiber membrane does not swing.

If the diameter of the spinning tube is large, the spinning operation is facilitated. However, it is desirable to reduce the diameter of the spinning tube or it increases the amount of the coagulation liquid required. The lower limit of the diameter of the spinning tube is 3 mm or more, and preferably 5 mm or more, and the upper limit of the diameter of the spinning tube is 20 mm or less, and preferably 10 mm or less.

It is preferable to appropriately set the length of the spinning tube corresponding to the spinning speed of the hollow fiber membrane in order to provide an appropriate coagulation time for formation of the hollow fiber membrane structure. The spinning tube may be formed of any material that can withstand the coagulation liquid. It is desirable to use a transparent material that allows the spinning state to be observed. For example, glass, polyethylene, polypropylene, polytetrafluoroethylene, or the like may be used as the material for the spinning tube. Among these, it is preferable to use polytetrafluoroethylene to which the spinning raw solution adheres to only a small extent so that the spinning operation is facilitated.

The thickness of the ultrafiltration membrane according to the present invention is 15 µm or more, and preferably 20 µm or more, but 2,000 µm or less, and preferably 1,000 µm or less, and particularly preferably 500 µm or less. If the thickness of the ultrafiltration membrane is less than 15 µm, the ultrafiltration membrane may have insufficient strength. If the thickness of the ultrafiltration membrane is more than 2,000 µm, the ultrafiltration membrane may have insufficient immunoglobulin monomer permeability.

When the ultrafiltration membrane according to the present invention has a dense layer on the inner surface of the hollow fiber or on one side of a flat membrane, the thickness of the dense layer is normally 100 µm or less, preferably 10 µm or less, and more preferably 1 µm or less in order to improve the immunoglobulin solution permeability.

The lower limit of the porosity of the ultrafiltration membrane according to the present invention is 30% or more, preferably 40% or more, and particularly preferably 50% or more. The upper limit of the porosity of the ultrafiltration membrane is 95% or less, preferably 90% or less, and particularly preferably 85% or less. If the porosity is less than 30%, the filtration speed may be insufficient. If the porosity is more than 95%, the ultrafiltration membrane may have insufficient strength. The porosity refers to a value determined from the apparent volume calculated from the cross-sectional area and the length of the membrane, the weight of the membrane, and the true density of the membrane material.

The shape of the ultrafiltration membrane according to the present invention is not particularly limited insofar as the ultrafiltration membrane exhibits fractionation performance. For example, the ultrafiltration membrane may be in the form of a hollow fiber, a flat membrane, a tube, or the like. It is effective that the ultrafiltration membrane be in the form of a hollow fiber since a large effective filtration membrane area is obtained with respect to the volume.

The membrane surface structure of the ultrafiltration membrane according to the present invention is not particularly limited. The membrane surface structure may have individual pores (e.g., circular or oval), continuously connected pores, reticulated micropores, slit-like micropores, or the like.

It suffices that the ultrafiltration membrane according to the present invention have a configuration in which at least the surface of the membrane that comes in contact with the immunoglobulin is an ultrafiltration membrane. A base material (support) formed of any material may be used to maintain the structure. For example, a support formed of fabric or nonwoven fabric or a porous inorganic body may be used as the base material (support) in order to improve the physical strength of the ultrafiltration membrane, and an ultrafiltration membrane may be formed on the base material.

Cross-flow filtration or dead-end filtration has been utilized as a general-purpose filtration method. Cross-flow filtration is characterized in that a treatment target liquid that contains fine particles (e.g., protein) is filtered while supplying the treatment target liquid to the membrane to separate particles having a different diameter. The fractionation performance is maintained by scraping the particles (cake layer) deposited on the surface of the membrane by utilizing a shear force caused by a parallel flow of the particle solution to maintain a stable cake layer for a long period of time. Dead-end filtration is characterized in that particles are caused to flow perpendicularly to the surface of the membrane. Therefore, the particles are accumulated on the surface of the membrane. The permeation resistance gradually increases as the filtration time increases so that the concentration of particles that pass through the membrane changes. Dead-end filtration is also referred to as vertical filtration or normal filtration.

Cross-flow filtration (also referred to as parallel filtration or tangential-flow filtration) according to the present invention is characterized in that an immunoglobulin solution is caused to flow parallel to the membrane and particles accumulated on the surface of the membrane are removed by a shear force to form a constant cake layer in which a dynamic equilibrium is established, so that a continuous operation is enabled while maintaining the fractionation performance.

The term "filtration linear velocity" used herein refers to the velocity of a solution that flows parallel to the membrane. The filtration linear velocity is not particularly limited insofar as the cake layer does not change to a large extent and fractionation performance can be achieved. For example, the lower limit of the filtration linear velocity is 0.1 cm/sec or more, preferably 1 cm/sec or more, and more preferably 10 cm/sec or more, and the upper limit of the filtration linear velocity is 200 cm/sec or less, and preferably 100 cm/sec or less. If the filtration linear velocity is more than 200 cm/sec, stress is applied to the immunoglobulin so that aggregation or cloudiness may occur. If the filtration linear velocity is less than 0.1 cm/sec, the throughput of immunoglobulin decreases so that cost increases.

In the present invention, the filtration pressure is not particularly limited insofar as fractionation performance can be achieved. In Patent Document 4, a back pressure is applied from the side of the immunoglobulin permeation so that a uniform pressure is applied to the entire membrane, and the immunoglobulin solution is filtered at a pressure equal to or lower than the transmembrane pressure (TMP) to achieve fractionation performance. However, since an apparatus that applies a back pressure is required, and filtration is performed at a low pressure, the throughput decreases. The separation method according to the present invention can maintain the fractionation performance even if the immunoglobulin is filtered at a pressure higher than the TMP so that the immunoglobulin permeability (permeation rate (throughput)) increases.

The lower limit of the filtration pressure is 0.001 MPa or more, and preferably 0.005 MPa or more. The upper limit of the filtration pressure is 0.3 MPa or less, and preferably 0.20 MPa or less.

If the filtration pressure is less than 0.001 MPa, productivity decreases due to a decrease in throughput. If the filtration pressure is more than 0.3 MPa, a cake layer may be rapidly formed so that clogging of the membrane may occur.

A cross-flow filtration apparatus used in the present invention is not particularly limited insofar as the apparatus can control the immunoglobulin concentration, linear velocity, pressure, and the like. For example, the cross-flow filtration apparatus may include a device that monitors the concentration of the immunoglobulin solution using an absorption spectrometer, and supplies a diluent in order to achieve a constant concentration of the immunoglobulin solution, and a device that controls the linear velocity in the direction tangential to the ultrafiltration membrane and the pressure across the ultrafiltration membrane.

Specifically, the cross-flow filtration apparatus may have a configuration shown in FIG. 1. The concentration of a solution contained in an immunoglobulin stock solution tank (4) is monitored using a concentration controller (11) provided with an absorption spectrometer. A signal generated by the concentration controller (11) is transmitted to a pump 1 (2) to control the rotation of the pump. The concentration of the solution contained in the immunoglobulin stock solution tank (4) is controlled while adding a diluent contained in a diluent tank (1) to the immunoglobulin stock solution tank (4). The pressure and the flow rate are monitored using a manometer 1 (5), a manometer 2 (6), and a flowmeter (10). A signal is transmitted from a pressure/flow rate controller (12) to a control valve (7) and a pump 2 (3) to control an ultrafiltration membrane module (8) so that the linear velocity in the tangential direction and the pressure across the ultrafiltration membrane are set to the desired values. An apparatus (e.g., absorption spectrometer or GPC) that can measure: the concentration of the immunoglobulin permeation solution that has passed through the ultrafiltration membrane and is contained in an immunoglobulin permeation solution tank (9) and; the ratio of immunoglobulin monomers to immunoglobulin dimers, may be connected to the cross-flow filtration apparatus.

The term "immunoglobulin stock solution" used herein refers to an immunoglobulin solution used to evaluate fractionation performance. The immunoglobulin stock solution may contain biocomponents other than immunoglobulin and viruses. The term "immunoglobulin permeation solution" used herein refers to a solution that has passed through and has been separated by the ultrafiltration membrane.

Figure 2:
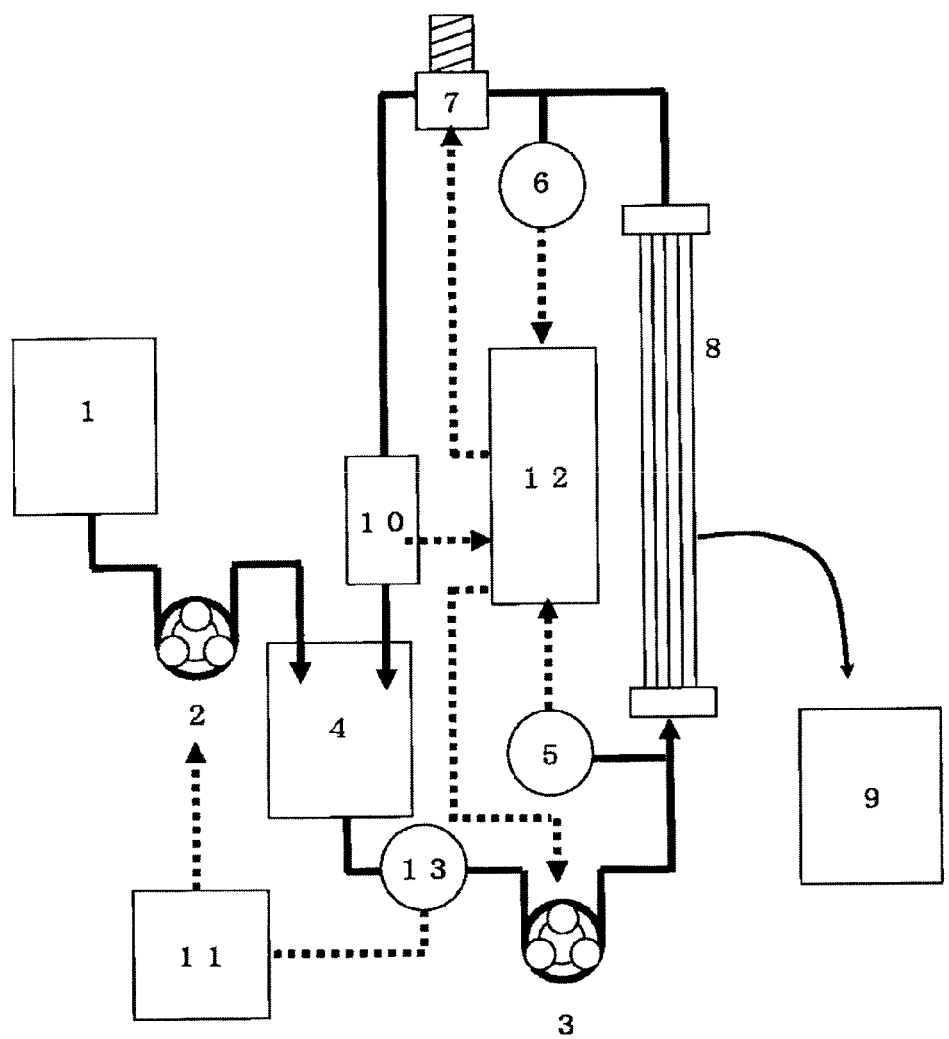
FIG. 2 is a view showing an example of cross-flow filtration apparatus according to the present invention.

The cross-flow filtration apparatus may also have a configuration shown in FIG. 2. An apparatus (e.g., UV flow cell (13)) that can monitor concentration is provided between the immunoglobulin stock solution tank (4) and the ultrafiltration membrane module (8). The concentration of the solution contained in the immunoglobulin stock solution tank (4) is monitored using the concentration controller (11). A signal generated by the concentration controller (11) is transmitted to the pump 1 (2) to control the rotation of the pump. The concentration of the solution contained in the immunoglobulin stock solution tank (4) is controlled while adding a diluent contained in the diluent tank (1) to the immunoglobulin stock solution tank (4). The pressure and the flow rate are monitored using the manometer 1 (5), the manometer 2 (6), and the flowmeter (10). A signal is transmitted from the pressure/flow rate controller (12) to the control valve (7) and the pump 2 (3) to control the ultrafiltration membrane module (8) so that the linear velocity in the tangential direction and the pressure across the ultrafiltration membrane are set to the desired values. An apparatus (e.g., absorption spectrometer or GPC) that can measure: the concentration of the immunoglobulin permeation solution that has permeated the ultrafiltration membrane and is contained in an immunoglobulin permeation solution tank (9) and; the ratio of immunoglobulin monomers to immunoglobulin dimers, may be connected to the cross-flow filtration apparatus.

The solvent or the diluent used in the present invention in order to adjust the immunoglobulin concentration is not particularly limited insofar as modification or aggregation of the immunoglobulin does not occur. Examples of the solvent or the diluent used to adjust the immunoglobulin concentration include calcium phosphate-phosphate buffered saline (PBS), phosphate buffered saline, Good buffers such as N-[tris(hydroxymethyl)methyl]glycine (tricine), N,N-bis(2-hydroxyethyl)glycine, N-tris(hydroxymethyl)methyl-3-aminopropanesulfonic acid (TAPS), 3-[(1,1-dimethyl-2-hydroxyethyl)amino-2-hydroxypropanesulfonic acid] (AMPSO), N-cyclohexyl-2-aminoethanesulfonic acid (CHES), N-cyclohexyl-2-hydroxy-3-aminopropanesulfonic acid (CAPSO), 2-amino-2-methyl-1-propanol (AMP), N-cyclohexyl-3-aminopropanesulfonic acid (CAPS), and piperazine-1,4-bis(2-ethanesulfonic acid) (PIPES), acetates, glycine, citrates, phosphates, Veronal, borate, succinates, tris (hydroxymethyl)aminomethane, imidazole, and the like. A diluent prepared by adding the immunoglobulin to the above buffer may also be used.

The concentration of the buffer used in the present invention is not particularly limited insofar as modification or aggregation of the immunoglobulin does not occur. For example, the lower limit of the concentration of the buffer is 1 mM or more, preferably 10 mM or more, and more preferably 50 mM or more, and the upper limit of the concentration of the buffer is 1 M or less, preferably 500 mM or less, and more preferably 200 mM or less.

The pH of the buffer used in the present invention is not particularly limited insofar as modification or aggregation of the immunoglobulin does not occur. For example, the lower limit of the pH of the buffer is 3 or higher, preferably 4 or higher, and more preferably 5 or higher, and the upper limit of the pH of the buffer is 10 or lower, preferably 9 or lower, and more preferably 8 or lower.

An aggregation inhibitor, a stabilizer, a preservative, and the like may be added to the immunoglobulin solution, as required.

Aggregation and cloudiness may occur during filtration because of the stress applied to the immunoglobulin. In this case, a surfactant, a saccharide, or the like may be added as the aggregation inhibitor.

The surfactant is an amphiphilic molecule having a hydrophilic site (hydrophilic group) and a hydrophobic site (hydrophobic group) in the molecule. It is considered that the hydrophobic group of the surfactant interacts with the hydrophobic site of the immunoglobulin to increase the solubility of the immunoglobulin in water and that the hydrophobic group of the surfactant suppresses hydrophobic interaction among immunoglobulins to inhibit aggregation.

The surfactant used in the present invention is not particularly limited insofar as modification or aggregation of the immunoglobulin does not occur and fractionation performance is not adversely affected. Examples of the surfactant include an amphoteric surfactant, a nonionic surfactant, a cationic surfactant, an anionic surfactant, and the like.

Examples of the amphoteric surfactant used in the present invention include amino acids, amino acid derivatives, sodium salts of alkylaminofatty acids, alkyl betaines, alkyl amine oxides, and the like. Among these, amino acids and/or amino acid derivatives are preferable. The amino acid used as the amphoteric surfactant is not particularly limited insofar as the amino acid suppresses aggregation of the immunoglobulin and can be dissolved in the immunoglobulin solution. For example, lysine, arginine, alanine, cysteine, glycine, serine, proline, or the like may be used. Among these, lysine, arginine, and alanine are preferable (lysine is particularly effective).

The amino acid derivative used in the present invention is a substance obtained by chemically modifying an amino acid. Examples of the amino acid derivatives include acetylated amino acids, acylated amino acids, and the like. The amino acid and/or the amino acid derivative may be used as acid addition salts. Examples of the acids that may form an acid addition salt include hydrochloric acid, sulfuric acid, and the like. These amphoteric surfactants may be used in combination. These amphoteric surfactants may be used in combination with other aggregation inhibitors.

Examples of the nonionic surfactant used in the present invention include polyoxyethylene alkyl ethers, polyoxyethylene alkyl phenyl ethers, sucrose fatty acid esters, sorbitan fatty acid esters, polyoxyethylene sorbitan fatty acid esters, fatty acid alkanol amides, and the like. Among these, polyoxyethylene alkyl ether polymers and/or derivatives thereof are preferable. The polyoxyethylene alkyl ether used as the nonionic surfactant is not particularly limited insofar as the polyoxyethylene alkyl ether suppresses aggregation of the immunoglobulin and can be dissolved in the immunoglobulin solution. For example, polyethylene glycol and/or polyethylene glycol derivatives may be used. Polyethylene glycol, polyethylene oxide, a polyethylene glycol-polypropylene glycol block copolymer, as well as a surfactant, a block copolymer and a graft copolymer containing polyethylene glycol as a hydrophilic segment, may be used as the aggregation inhibitor. These nonionic surfactants may be used in combination. These nonionic surfactants may be used in combination with other aggregation inhibitors.

Examples of the cationic surfactant used in the present invention include alkyltrimethylammonium salts, dialkyldimethylammonium salts, and the like.

Examples of the anionic surfactant used in the present invention include sodium salts of fatty acids, potassium salts of fatty acids, sodium salts of α-sulfo fatty acid esters, linear sodium alkylbenzenesulfonates, sodium salts of alkyl sulfate esters, sodium salts of alkyl ether sulfates, sodium α-olefin sulphonates, sodium alkyl sulfonates, and the like.

The lower limit of the molecular weight of the surfactant used in the present invention is 30 Da or more, and preferably 50 Da or more. The upper limit of the molecular weight of the surfactant is 50,000 Da or less, and preferably 30,000 Da or less. If the molecular weight of the surfactant is less than 30 Da, a sufficient aggregation-inhibiting effect is not obtained. If the molecular weight of the surfactant is more than 30,000 Da, the surfactant or a composite of the surfactant and the immunoglobulin causes clogging or fouling of the membrane.

The saccharide used in the present invention is not particularly limited insofar as the saccharide suppresses aggregation of the immunoglobulin and can be dissolved in the immunoglobulin solution. Specific examples of the saccharide include glucose, sorbitol, and saccharose The lower limit of the concentration of the aggregation inhibitor used in the present invention is preferably 0.1 g/L or more, and more preferably 0.5 g/L or more, and the upper limit of the concentration of the aggregation inhibitor is preferably 200 g/L or less, and more preferably 150 g/L or less, although the concentration of the aggregation inhibitor varies depending on the type of the aggregation inhibitor. If the concentration of the aggregation inhibitor is less than 0.1 g/L, aggregation of the immunoglobulin may not be sufficiently suppressed. If the concentration of the aggregation inhibitor is more than 200 g/L, the immunoglobulin permeability may decrease due to an increase in the viscosity of the immunoglobulin solution.

The above surfactants, saccharides, and the like have an effect of preventing deterioration and adsorption of the immunoglobulin in addition to the aggregation inhibiting effect. Inorganic salts also have an effect of preventing deterioration and adsorption of the immunoglobulin.

Examples of the inorganic salts used in the present invention include sodium chloride, potassium chloride, magnesium chloride, calcium chloride, magnesium sulfate, and the like. The lower limit of the concentration of the inorganic salt is preferably 1 mM or more, more preferably 10 mM or more, and most preferably 50 mM or more, for example. The upper limit of the concentration of the inorganic salt is preferably 1 M or less, more preferably 500 mM or less, and most preferably 200 mM or less.

The preservative used in the present invention is not particularly limited insofar as the properties of the immunoglobulin and fractionation performance are not adversely affected. Examples of the preservative include sodium azide and the like. The lower limit of the concentration of the preservative is 0.001 wt % or more, and preferably 0.005 wt % or more, and the upper limit of the concentration of the preservative is 1 wt % or less, and preferably 0.5 wt % or less.

In the present invention, an index of the fractionation performance when separating immunoglobulin monomers from the immunoglobulin solution containing immunoglobulin monomers and immunoglobulin aggregates (e.g., dimer) is as follows.

When using immunoglobulin monomers as a medicine, it is desirable to remove biological impurities that may cause side effects as much as possible. A medicine having an immunoglobulin dimer content of 1% or less is considered to be safe. Therefore, the ratio of immunoglobulin dimer permeability to immunoglobulin monomer permeability (immunoglobulin dimer permeability/immunoglobulin monomer permeability) is 0.20 or less, preferably 0.15 or less, and more preferably 0.10 or less in order to achieve such an immunoglobulin dimer content. When the amount of immunoglobulin dimers contained in the immunoglobulin stock solution is small, the ratio of immunoglobulin dimer permeability to immunoglobulin monomer permeability may be 0.30 or less so that immunoglobulin dimer content in the permeation liquid is 1% or less. On the other hand, it is preferable to collect immunoglobulin monomers as much as possible. In the present invention, immunoglobulin monomer permeability is 80% or more, preferably 85% or more, and more preferably 90% or more.

It has been considered that a cake layer is formed immediately after starting cross-flow filtration so that fractionation performance is achieved. However, it was found that formation of the cake layer takes time, and immunoglobulin dimer content in the filtrate is considerably high in the initial stage of filtration. In the present invention, the immunoglobulin permeation solution obtained in the initial stage of filtration (i.e., which has a high immunoglobulin dimer content) is circulated to the immunoglobulin stock solution for a given period of time, and the immunoglobulin permeation solution is collected after fractionation performance has been achieved to reduce immunoglobulin dimer content without the loss of immunoglobulin monomers.

In the present invention, the period of time in which the immunoglobulin permeation solution is recirculated to the immunoglobulin stock solution is not particularly limited insofar as immunoglobulin dimer content in the resulting immunoglobulin permeation solution can be reduced to the desired value. For example, the immunoglobulin permeation solution may be recirculated to the immunoglobulin stock solution until immunoglobulin dimer content in the immunoglobulin permeation solution or the ratio of immunoglobulin dimer permeability to immunoglobulin monomer permeability reaches the desired value. When using immunoglobulin monomers as a medicine, it is desirable to remove biological impurities that may cause side effects as much as possible. Therefore, immunoglobulin dimer content is 1% or less, and preferably 0.75% or less. The period of time may be set according to the desired immunoglobulin dimer content.

The period of time may be set corresponding to the ratio of immunoglobulin dimer permeability to immunoglobulin monomer permeability (immunoglobulin dimer permeability/immuno globulin monomer permeability (permeability ratio)). A small permeability ratio indicates high fractionation performance. The permeability ratio is 0.20 or less, preferably 0.15 or less, more preferably 0.10 or less, and most preferably 0.075 or less. The period of time may be set according to the desired permeability ratio.

The period of time may be set using data that is obtained by another analyzer and that has a correlation with immunoglobulin dimer content. For example, a UV-visible absorbance, a value obtained by infrared spectroscopy, or the like may be used.

An affinity chromatography purification step is indispensable when purifying a monoclonal antibody. In particular, affinity chromatography using protein A or the like as the ligand has been utilized. In this case, the immunoglobulin is separated by utilizing the difference in affinities of the immunoglobulin and other biocomponents with the ligand. Specifically, biocomponents including immunoglobulins, contaminant proteins, sugar chains, and nucleic acids are subjected to affinity chromatography so that the ligand binds to the immunoglobulins only. The immunoglobulins are separated from the ligand by utilizing a low pH, a high pH, a salt, a competitive ligand, or the like, and collected to obtain the purified immunoglobulin.

In the affinity chromatography purification step, it is necessary to subject the immunoglobulin to a low pH or a salt in order to elute the immunoglobulin from the ligand. However, this operation may cause aggregation of the immunoglobulin so that immunoglobulin aggregates (e.g., dimer) are produced, or may cause elution of the ligand (e.g., protein A) so that the ligand may form an aggregate with the immunoglobulin.

The immunoglobulin can be sufficiently purified by performing the separation method according to the present invention after performing affinity chromatography purification using protein A or the like as the ligand.

The protein A used in the present invention includes protein A collected from a natural source, a synthesized protein A (e.g., by peptide synthesis or recombination), and altered products thereof that can bind to a protein having a CH2/CH3 region (e.g., Fc region). The protein A is commercially available from Repligen, Pharmacia, and Fermatech. The protein A is generally fixed on a solid support as a ligand. The term "protein A column" refers to an affinity chromatography resin or column including a chromatography solid support matrix to which the protein A covalently bonds. Examples of the ligand used for affinity chromatography other than the protein A include protein L, protein G, and the like. Each of the protein L and the protein G used in the present invention includes a protein collected from a natural source, a synthesized protein (e.g., by peptide synthesis or recombination), and altered products thereof that can bind to a protein having a CH2/CH3 region (e.g., Fc region). An affinity chromatography purification method using an affinity chromatography resin or column obtained by combining the protein A, protein L, and protein G is also included within the scope of the present invention.

A cross-flow filtration method for a protein solution using an ultrafiltration membrane is mainly used as a filtration method that enables a continuous separation process. However, since the protein concentration decreases due to filtration, a concentration step is required after filtration. Therefore, the size of an immunoglobulin permeation solution tank that stores the immunoglobulin permeation solution must be increased and the installation cost increases. A water-addition cross-flow filtration method has a problem in that a tank for a solution used as a diluent, a buffer, and an additive increase cost.

In the separation/concentration method according to the present invention, a series of steps can be performed within a short time so that cost can be reduced because the immunoglobulin permeation solution diluted in the separation step is continuously concentrated at the same time. It is preferable to recycle the liquid that has passed through the membrane in the concentration step as a diluent used in the separation step. The diluent contains a buffer, a salt, a stabilizer, and the like. Since these components have a low molecular weight, these components are not trapped by the membrane in the separation step and the concentration step. Specifically, since the concentration of the buffer, salt, and stabilizer in the diluent used in the separation step is almost the same as the concentration of the buffer, salt, and stabilizer in the immunoglobulin permeation solution that has passed through the membrane in the concentration step, the immunoglobulin permeation solution can be used as a diluent used in the separation step.

According to this separation/concentration method, the cost of a tank for a solution used as a diluent, a buffer, and an additive can be significantly reduced.

The term "ultrafiltration membrane for concentration" used herein refers to a membrane used to concentrate the solution separated by the ultrafiltration membrane.

The material for the ultrafiltration membrane for concentration used in the concentration step according to the present invention is not particularly limited. The ultrafiltration membrane for concentration may be a polymer membrane or an inorganic membrane. Examples of the ultrafiltration membrane for concentration include a polysulfone polymer membrane (e.g., polysulfone, polyethersulfone, or polyarylsulfone), an aromatic ether polymer membrane, a polyacrylic polymer membrane, a polyacrylonitrile polymer membrane, a cellulose polymer membrane, a polycarbonate polymer membrane, a polyvinylidene fluoride polymer membrane, a polytetrafluoroethylene polymer membrane, a polyethylene polymer membrane, a polypropylene polymer membrane, a polyamide polymer membrane, a polyetherimide polymer membrane, and the like. Among these, it is preferable to use a polysulfone polymer membrane.

The lower limit of the molecular weight cut-off of the ultrafiltration membrane for concentration that is used in the immunoglobulin concentration step according to the present invention in order to concentrate the immunoglobulin is 1,000 or more, preferably 5,000 or more, and more preferably 10,000 or more. The upper limit of the molecular weight cut-off of the ultrafiltration membrane for concentration is 100,000 or less, preferably 90,000 or less, and more preferably 80,000 or less. If the molecular weight cut-off of the ultrafiltration membrane for concentration is more than 100,000, the recovery rate of immunoglobulin monomers decreases. If the molecular weight cut-off of the ultrafiltration membrane for concentration is less than 1000, the amount of liquid that passes through the membrane per unit time decreases to a large extent.

The concentration of the preconcentration-immunoglobulin solution used in the immunoglobulin concentration step according to the present invention refers to the concentration of the immunoglobulin solution that has passed through the membrane in the immunoglobulin separation step. The concentration of the immunoglobulin solution generally decreases from the initial concentration in the immunoglobulin separation step. A decrease in the concentration of the immunoglobulin solution varies depending on the membrane module and the filtration conditions. When the initial concentration is 100, the lower limit of a decrease in the concentration of the immunoglobulin solution is 0.1, and preferably 0.5. The upper limit of a decrease in the concentration of the immunoglobulin solution is 99, and preferably 95. For example, when filtering 1 to 150 g/L of the immunoglobulin solution, the concentration of the immunoglobulin solution that has passed through the membrane is 0.1 to 149 g/L. When filtering 1 to 100 g/L of the immunoglobulin solution, the concentration of the immunoglobulin solution that has passed through the membrane is 0.1 to 99 g/L.

The cross-flow filtration conditions when concentrating the immunoglobulin solution that has passed through the membrane are not particularly limited insofar as the desired immunoglobulin concentration is obtained. For example, the lower limit of the linear velocity is 0.01 cm/sec or more, and preferably 0.1 cm/sec or more, and the upper limit of the linear velocity is 100 cm/sec or less, and preferably 75 cm/sec or less. The lower limit of the cross-flow filtration pressure is 0.01 MPa or more, and preferably 0.02 MPa or more, and the upper limit of the cross-flow filtration pressure is 0.5 MPa or less, and preferably 0.3 MPa or less.

The concentration of the postconcentration-immunoglobulin solution used in the immunoglobulin concentration step according to the present invention varies depending on the type and the application of the immunoglobulin and the subsequent purification step (e.g., virus removal step). The concentration rate is set corresponding to the objective. The lower limit is preferably 0.5 g/L or more, and more preferably 1 g/L or more, and the upper limit is preferably 300 g/L or less, and more preferably 150 g/L or less.

Figure 4:
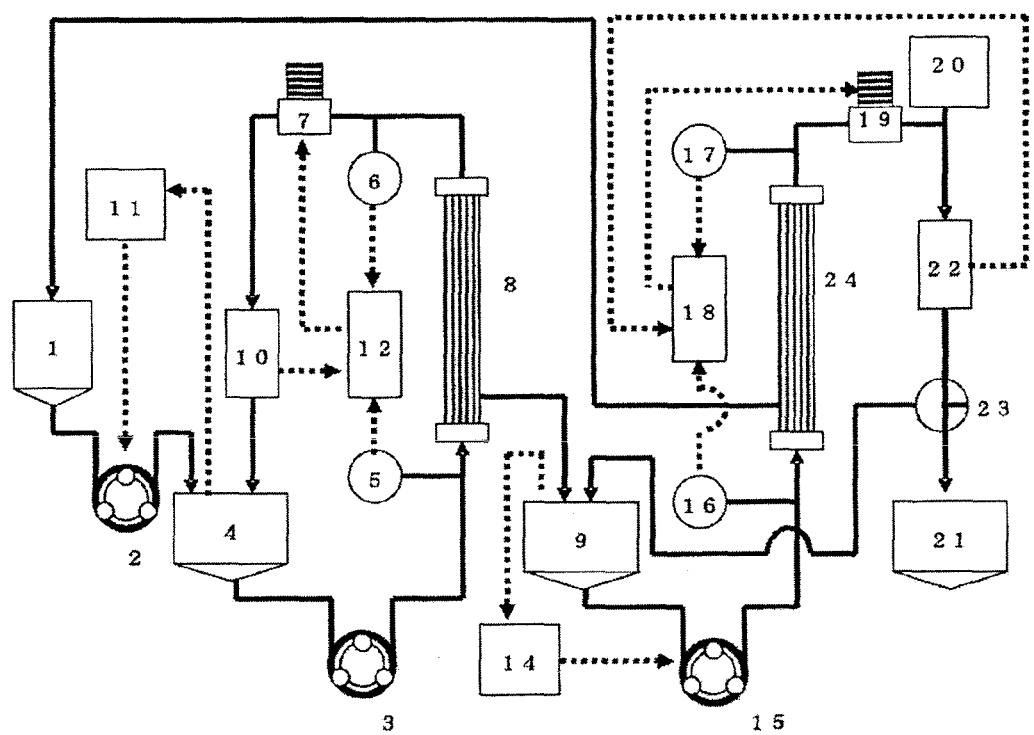
FIG. 4 is a view showing an example of cross-flow filtration/concentration method according to the present invention.

The separation step separates immunoglobulin monomers and immunoglobulin dimers by cross-flow filtration. It is preferable to use an apparatus that includes an apparatus that monitors the concentration of the immunoglobulin, an apparatus that adjusts the concentration of the immunoglobulin, a means that controls the linear velocity of the immunoglobulin solution supplied to the ultrafiltration membrane, and an apparatus that controls the filtration pressure through the ultrafiltration membrane. The concentration step concentrates the immunoglobulin monomer solution obtained by the separation step. It is preferable to use an apparatus that includes an apparatus that monitors the concentration of the immunoglobulin monomer solution before and after concentration, and an apparatus that controls the linear velocity of the immunoglobulin monomer solution and the filtration pressure. It is preferable to recycle the immunoglobulin permeation solution obtained by the concentration step as the diluent that adjusts the concentration of the immunoglobulin solution used in the separation step. FIG. 4 shows a specific example of such an apparatus.

In the separation step, the immunoglobulin solution contained in the immunoglobulin stock solution tank (4) is supplied to the ultrafiltration membrane module (8) using the supply pump 2 (3). The filtration pressure and the filtration flow rate are monitored using the manometer 1 (5), the manometer 2 (6), and the flowmeter 1 (10). A signal is transmitted from the pressure/flow rate controller 1 (12) to the control valve (7) so that the linear velocity in the tangential direction and the pressure across the ultrafiltration membrane module (8) are set to the desired values. The immunoglobulin solution that has not passed through the ultrafiltration membrane module (8) is returned to the immunoglobulin stock solution tank (4). The concentration of the immunoglobulin solution contained in the immunoglobulin stock solution tank (4) is monitored using the concentration controller 1 (11) provided with an absorption spectrometer. A signal is transmitted to the pump 1 (2) to control the concentration of the immunoglobulin solution, and the diluent contained in the diluent tank (1) is added to the immunoglobulin stock solution tank (4). The immunoglobulin permeation solution that has passed through the ultrafiltration membrane module (8) is supplied to the immunoglobulin permeation solution tank (9). The separation step is thus completed. In the concentration step, the immunoglobulin permeation solution is supplied to a ultrafiltration membrane-for-concentration module (24) using a supply pump 3 (15). The filtration pressure and the filtration flow rate are monitored using a manometer 3 (16), a manometer 4 (17), and a flowmeter 2 (23). A signal is transmitted from a pressure/flow rate controller 2 (18) to a control valve 2 (19) so that the linear velocity in the tangential direction and the pressure across the ultrafiltration membrane-for-concentration module (24) are set to the desired values. The concentration of the immunoglobulin solution is monitored using a concentration controller 2 (14) and an absorption spectrometer (20), and the concentration rate is adjusted using the concentration controller 2 (14) and the pressure/flow rate controller 2 (18).

The immunoglobulin solution that has passed through the ultrafiltration membrane-for-concentration module (24) and can be recycled as the diluent is supplied to the diluent tank (1). The concentration of the concentrated immunoglobulin solution is monitored using the absorption spectrometer (20). The immunoglobulin solution is recycled to the immunoglobulin permeation solution tank (9) until the desired concentration is reached. The flow path is changed using a switch valve (23) when the desired concentration has been reached, and the concentrated immunoglobulin solution is collected in a concentrated immunoglobulin solution tank (21).

The term "ultrafiltration membrane module" used in the present invention refers to a module that includes a flat membrane or a hollow fiber membrane provided in a casing, for example, and has at least one liquid inlet port through which the immunoglobulin solution is supplied to the casing, and at least one liquid outlet port through which the separated liquid is discharged. The casing used for the module is assembled from one or more casing components. The material for the casing components may be appropriately selected from metals, glass, thermoplastic resins, thermosetting resins, and the like. It is preferable to use a transparent thermoplastic resin that allows the state of the inside of the casing to be observed. Specific examples of the thermoplastic resin include polymethyl methacrylate, polystyrene, a hard vinyl chloride resin, polyethylene terephthalate, polypropylene, a polystyrene-butadiene copolymer, polycarbonate, polymethyl methacrylate, and the like. It is particularly preferable to use a transparent amorphous resin, such as a polystyrene-butadiene copolymer, polycarbonate, or polymethyl methacrylate.

A method of producing the casing components used when assembling the casing used for the module according to the present invention is not particularly limited insofar as the method allows molding. For example, welding, press molding, injection molding, reactive injection molding, ultrasonic bonding, plasma bonding, adhesion using an adhesive, or the like may be used. These methods may be used either individually or in combination. It is preferable to produce the casing components by sealing an injection molded article formed of a transparent thermoplastic resin with an appropriate adhesive.

The surface of the casing and/or the casing component used for the module according to the present invention that does and/or does not come in contact with the separation target liquid may be surface-treated during and/or after molding and/or during and/or after assembly. For example, when hydrophilizing the surface of the casing and/or the casing component, a hydrophilic polymer may be applied to the surface of the casing and/or the casing component, or the surface of the casing and/or the casing component may be oxidized by plasma treatment in air. When hydrophobizing the surface of the casing and/or the casing component, a water-repelling agent and/or a releasing agent may be applied to the surface of the casing and/or the casing component. When reducing permeation of oxygen, an inorganic coating such as a silicon dioxide film may be formed on the surface of the casing and/or the casing component by deposition or the like. Adhesion between the same materials and/or different materials at the interface can be easily controlled when assembling the module by hydrophilizing the surface of the casing and/or the casing component, and removability from a protective film or the like that is temporarily used during assembly can be improved by hydrophobizing the surface of the casing and/or the casing component.

The structure of the module according to the present invention varies depending on the shape of the membrane (e.g., hollow fiber membrane or flat membrane). It suffices that the module according to the present invention have such a structure that a hollow fiber membrane or a flat membrane can be appropriately placed in the casing, and the immunoglobulin stock solution and the immunoglobulin solution to be separated are not mixed. A holding material (e.g., metal mesh or nonwoven fabric) that holds the membrane may also be incorporated in the casing.

Since the separation method according to the present invention utilizes size fractionation, the separation method according to the present invention may also be used for purification of synthetic medicine, purification of beverages (e.g., sake, beer, wine, low-malt beer, tea, oolong tea, vegetable juice, and fruit juice), separation of particles from chemicals, treated water, and the like, separation for purifying clean water/sewage water (oil-water separation and liquid-gas separation), and the like.

EXAMPLES

The present invention is further described below by way of examples and comparative examples. Note that the present invention is not limited to the following examples.
[Production of Polysulfone Polymer Membrane]
<Production of Hollow Fiber Membrane (PSf-1)>
280 g of polysulfone ("P1700" manufactured by UCC, hereinafter abbreviated as "PSf") and 110 g of polyvinylpyrrolidone ("K-90" manufactured by BASF, hereinafter abbreviated as "PVP") were added to 1,650 g of N,N-dimethylacetamide (manufactured by Wako Pure Chemical Industries, Ltd., hereinafter abbreviated as "DMAc"). The mixture was poured into a membrane raw material solution reactor ($5000 \times 10^{-6}$ m$^3$). An operation of reducing the pressure inside the reactor and replacing the atmosphere inside the reactor with nitrogen (hereinafter may be referred to as "pressure reduction/nitrogen replacement operation") was repeated five times with stirring. The temperature of the solution inside the reactor was then increased to 60° C. to obtain a homogeneous PSf DMAc solution. After confirming that a homogeneous solution was obtained, stirring was stopped. The solution was then defoamed under reduced pressure. The pressure inside the reactor was then increased to atmospheric pressure to obtain a spinning membrane raw material solution maintained at 60° C.

520 g of DMAc was mixed with 480 g of purified water, and the mixture was added to an internal coagulation liquid reactor ($3000 \times 10^{-6}$ m$^3$). A pressure reduction/nitrogen replacement operation was repented five times to obtain an internal coagulation liquid.

The internal coagulation liquid and the membrane raw material solution were passed through a double spinneret (inner diameter: 100 μm, slit width: 50 μm, outer diameter: 300 μm) maintained at 60° C. The flow rate was appropriately adjusted corresponding to the take-up speed during spinning.

The resulting hollow fiber membrane was passed through an air gap (0.6 m), introduced into an external coagulation liquid (purified water) contained in a coagulation bath (60° C.), and wound using a winder. The take-up speed was 2,400 m/h to 4,800 m/h.

The resulting hollow fiber membrane was repeatedly immersed in and washed with purified water (60° C.), and dried at 70° C. for six hours using a hot air dryer. A polysulfone polymer membrane having a molecular weight cut-off of 300,000, an inner diameter of 151 μm, and a thickness of 30 μm was thus obtained.
<Production of Hollow Fiber Membrane (PSf-2)>
A polysulfone polymer membrane having a molecular weight cut-off of 360,000, an inner diameter of 207 μm, and a thickness of 41 μm was obtained in the same manner as the hollow fiber membrane PSf-1, except for changing the composition of the internal coagulation liquid (purified water/DMAc) and the polysulfone concentration in the membrane raw material solution.
<Production of Hollow Fiber Membrane (PSf-3)>
A polysulfone polymer membrane having a molecular weight cut-off of 240,000, an inner diameter of 199 μm, and a thickness of 37 μm was obtained in the same manner as the hollow fiber membrane PSf-1, except for changing the composition of the internal coagulation liquid (purified water/DMAc) and the polysulfone concentration in the membrane raw material solution.
<Production of Hollow Fiber Membrane (PSf-4)>
A polysulfone polymer membrane having a molecular weight cut-off of 600,000, an inner diameter of 155 μm, and a thickness of 33 μm was obtained in the same manner as the hollow fiber membrane PSf-1, except for changing the composition of the internal coagulation liquid (purified water/DMAc) and the polysulfone concentration in the membrane raw material solution.
<Production of Hollow Fiber Membrane (PSf-5)>
A polysulfone polymer membrane having a molecular weight cut-off of 1,000,000, an inner diameter of 157 μm, and a thickness of 36 μm was obtained in the same manner as the hollow fiber membrane PSf-1, except for changing the composition of the internal coagulation liquid (purified water/DMAc) and the polysulfone concentration in the membrane raw material solution.

<Production of Hollow Fiber Membrane (PSf-6)>

A polysulfone polymer membrane having a molecular weight cut-off of 300,000, an inner diameter of 498 μm, and a thickness of 87 μm was obtained in the same manner as the hollow fiber membrane PSf-1, except that a double spinneret having an inner diameter of 350 μm, a slit width of 75 μm, and an outer diameter of 750 μm and an air gap of 0.1 m were used.

[Production of Aromatic Ether Polymer Membrane]

<Production of Polystyrene-Polyethylene Glycol Block Copolymer>

A reactor ($5000 \times 10^{-6}$ m$^3$) containing 2,400 g of xylene (manufactured by Wako Pure Chemical Industries, Ltd.) was charged with 480 g of styrene (manufactured by Wako Pure Chemical Industries, Ltd.) and 120 g of a polyethylene glycol unit-containing Macro azo initiator "VPE-0201" (manufactured by Wako Pure Chemical Industries, Ltd., the number average molecular weight of the polyethylene glycol segment was about 2000). The atmosphere inside the reaction system was replaced by dry nitrogen by bubbling dry nitrogen through the reaction system for 30 minutes or more. The mixture was then polymerized at 130° C. for seven hours. After cooling the reaction solution to room temperature, the reaction solution was gradually poured into excess hexane (manufactured by Wake Pure Chemical Industries, Ltd., special grade) to precipitate the polymer. The polymer was washed three times with hexane, and dried at 50° C. for 24 hours under a reduced pressure of 0.133 KPa to completely remove the residual solvent, monomers, and the like. 409 g of a white powder (polymer) was thus obtained (yield: 68 wt %). When producing a polystyrene-polyethylene glycol block copolymer having a different compositional ratio, the amounts of styrene and the polyethylene glycol unit-containing Macro azo initiator were appropriately changed.

<Production of Hollow Fiber Membrane (PPE-1)>

A polystyrene-polyethylene glycol block copolymer having a polystyrene/polyethylene glycol ratio of 62/38 (wt %), a number average molecular weight of 20,100, and a molecular weight distribution of 1.7 was produced in the same manner as described above.

320 g of poly(2,6-dimethylphenylene-1,4-oxide) (manufactured by Sigma-Aldrich Japan K.K., hereinafter abbreviated as "PPE") and 110 g of the polystyrene-polyethylene glycol block copolymer (hydrophilic polymer) were added to 1,600 g of N-methyl-2-pyrrolidone (hereinafter abbreviated as "NMP"), and the mixture was poured into a membrane raw material solution reactor ($5000 \times 10^{-6}$ m$^3$). An operation of reducing the pressure inside the reactor to 0.02 MPa and replacing the atmosphere inside the reactor with nitrogen was repeated five times with stirring. The temperature of the solution inside the reactor was then increased to 160° C. to obtain a homogeneous PPE NMP solution. After stopping stirring, the temperature inside the reactor was decreased to 90° C. over one hour while maintaining the pressure inside the reactor at 0.02 MPa. The pressure inside the reactor was then increased to atmospheric pressure using nitrogen to obtain a spinning membrane raw material solution maintained at 90° C.

700 g of NMP was mixed with 300 g of purified water, and the mixture was added to an internal coagulation liquid reactor ($3000 \times 10^{-6}$ m$^3$). An operation of reducing the pressure inside the reactor to 0.02 MPa and replacing the atmosphere inside the reactor with nitrogen was repeated five times. The temperature inside the reactor was then increased to 90° C. while maintaining the pressure inside the reactor at 0.02 MPa. After one hour, the pressure inside the reactor was increased to atmospheric pressure using nitrogen to obtain an internal coagulation liquid (water/NMP (30/70 wt %)) maintained at 90° C.

The internal coagulation liquid maintained at 90° C. was caused to flow through the inside of a double spinneret (inner diameter: 100 μm, slit width: 50 μm, outer diameter: 300 μm) maintained at 90° C. at a flow rate of about $60 \times 10^{-6}$ m$^3$/h to about $120 \times 10^{-6}$ m$^3$/h. The membrane raw material solution maintained at 90° C. was then caused to flow through the double spinneret at a flow rate of $90 \times 10^{-6}$ m$^3$/h to $240 \times 10^{-6}$ m$^3$/h. The flow rate was appropriately adjusted corresponding to the take-up speed during spinning.

The resulting hollow fiber membrane was passed through an air gap (0.6 m), introduced into an external coagulation liquid (purified water) contained in a coagulation bath (90° C.), and wound using a winder. The take-up speed was 4,200 m/h. The resulting hollow fiber membrane was immersed in and washed with purified water at 80° C. five times, and dried at 70° C. for six hours using a hot air dryer.

An ultrafiltration membrane having a different membrane structure was produced by appropriately changing the compositional ratio (PPE/hydrophilic polymer/good solvent), the coagulating liquid, and the like.

A hollow fiber membrane (PPE-1) having a molecular weight cut-off of 380,000, an inner diameter of 173 μm, and a thickness of 30 μm was thus obtained.

<Production of Hollow Fiber Membrane (PPE-2)>

A hollow fiber membrane having a molecular weight cut-off of 890,000, an inner diameter of 161 μm, and a thickness of 35 μm was obtained in the same manner as the hollow fiber membrane (PPE-1), except for changing the compositional ratio (PPE/hydrophilic polymer/good solvent), the coagulating liquid, and the like.

<Production of Hollow Fiber Membrane (PPE-3)>

A hollow fiber membrane having a an inner diameter of 169 μm and a thickness of 39 μm was obtained in the same manner as the hollow fiber membrane (PPE-1), except that hydrophilization using the polystyrene-polyethylene glycol block copolymer was not performed. The molecular weight cut-off could not be measured due to adsorption of proteins.

<Production of Hollow Fiber Membrane (PPE-4)>

A hollow fiber membrane having a molecular weight cut-off of 410,000, an inner diameter of 568 μm, and a thickness of 123 μm was obtained in the same manner as the hollow fiber membrane (PPE-1), except that a double spinneret having an inner diameter of 350 μm, a slit width of 75 μm, and an outer diameter of 500 μm and an air gap of 0.1 m were used.

[Production of (Meth)acrylic Polymer Membrane]

<Production of Hollow Fiber Membrane (PMA)>

160 g of a (meth)acrylic polymer ("Dianal BR" manufactured by Mitsubishi Rayon Co., Ltd., hereinafter abbreviated as "PMMA") and 50 g of polyvinylpyrrolidone ("K-30" manufactured by BASF, hereinafter abbreviated as "PVP") were added to 890 g of dimethyl sulfoxide (manufactured by Wako Pure Chemical Industries, Ltd., hereinafter abbreviated as "DMSO"). The mixture was poured into a membrane raw material solution reactor ($5000 \times 10^{-6}$ m$^3$). An operation of reducing the pressure inside the reactor and replacing the atmosphere inside the reactor with nitrogen was repeated five times with stirring. The temperature of the mixture inside the reactor was then increased to effect dissolution to obtain a homogeneous DMSO solution containing PMMA. After confirming that a homogeneous solution was obtained, stirring was stopped. The solution was then defoamed under reduced pressure. The pressure inside the reactor was then increased to atmospheric pressure to obtain a spinning membrane raw material solution maintained at 60° C.

500 g of DMSO was mixed with 500 g of purified water, and the mixture was added to an internal coagulation liquid reactor ($3000 \times 10^{-6}$ m$^3$). A pressure reduction/nitrogen replacement operation was repeated five times to obtain an internal coagulation liquid.

The internal coagulation liquid and the membrane raw material solution were passed through a double spinneret (inner diameter: 100 µm, slit width: 50 µm, outer diameter: 300 µm) maintained at 60° C. The flow rate was appropriately adjusted corresponding to the take-up speed during spinning.

The resulting hollow fiber membrane was passed through an air gap (0.6 m), introduced into an external coagulation liquid (purified water) contained in a coagulation bath (60° C.), and wound using a winder. The take-up speed was 2,400 m/h to 4,800 m/h.

The resulting hollow fiber membrane was repeatedly immersed in and washed with purified water (60° C.), and dried at 60° C. for six hours using a hot air dryer.

A hollow fiber membrane having a molecular weight cut-off of 350,000, an inner diameter of 160 µm, and a thickness of 35 µm was thus obtained.

[Production of Acrylonitrile-Based Polymer Membrane]
<Production of Hollow Fiber Membrane (PAN)>

140 g of an acrylonitrile copolymer (i.e., a copolymer of acrylonitrile (91.5 wt %) and methyl acrylate (8.5 wt %)) and 10 g of PVP ("K-17" manufactured by BASF) were added to 850 g of dimethyl sulfoxide (manufactured by Wako Pure Chemical Industries, Ltd., hereinafter abbreviated as "DMSO"). The mixture was poured into a membrane raw material solution reactor ($5000 \times 10^{-6}$ m$^3$). An operation of reducing the pressure inside the reactor and replacing the atmosphere inside the reactor with nitrogen was repeated five times with stirring. The temperature of the solution inside the reactor was then increased to 80° C. to obtain a homogeneous DMSO solution containing acrylonitrile copolymer. After confirming that a homogeneous solution was obtained, stirring was stopped. The solution was then defoamed under reduced pressure. The pressure inside the reactor was then increased to atmospheric pressure to obtain a spinning membrane raw material solution maintained at 80° C.

850 g of DMSO was mixed with 150 g of purified water, and the mixture was added to an internal coagulation liquid reactor ($3000 \times 10^{-6}$ m$^3$). A pressure reduction/nitrogen replacement operation was repeated five times to obtain an internal coagulation liquid.

The internal coagulation liquid and the membrane raw material solution were passed through a double spinneret (inner diameter: 100 µm, slit width: 50 µm outer diameter: 300 µm) maintained at 80° C. The flow rate was appropriately adjusted corresponding to the take-up speed during spinning.

The resulting hollow fiber membrane was passed through an air gap (0.6 m), introduced into an external coagulation liquid (purified water) contained in a coagulation bath (60° C.), and wound using a winder. The take-up speed was 2,400 m/h to 4,800 m/h.

The resulting hollow fiber membrane was repeatedly immersed in and washed with purified water (80° C.), and dried at 70° C. for six hours using a hot air dryer. A hollow fiber membrane having a molecular weight cut-off of 360,000, an inner diameter of 169 µm, and a thickness of 35 µm was thus obtained.

[Production of Fluorinated Polymer Membrane]
<Production of Hollow Fiber Membrane (PVDF)>

A composition containing 45 wt % of polyvinylidene fluoride ("KF7200" manufactured by Kureha Corporation) and 55 wt % of dicyclohexyl phthalate (manufactured by Osaka Organic Chemical Industry Co., Ltd.) was stirred at 70° C. using a Henschel mixer, and cooled to obtain a powder. The powder was introduced into a twin-screw extruder ("Labo Plastomill Model 50C 150" manufactured by Toyo Seiki Seisaku-Sho, Ltd.) from a hopper, and melt-mixed at 210° C. to obtain a uniform solution. The solution was extruded into a hollow fiber membrane from a double spinneret (inner diameter: 800 µm, outer diameter: 1,200 µm) at a discharge speed of 17 m/min while causing dibutyl phthalate (manufactured by Sanken Kako Co., Ltd., 130° C.) to flow inside the hollow portion at 8 ml/min. The extruded product was cooled and solidified in a water bath maintained at 40° C., and wound at 60 m/min. After removing dicyclohexyl phthalate and dibutyl phthalate by extraction with 99% methanol-modified ethanol (manufactured by Imazu Chemical Co., Ltd.), ethanol adhering to the membrane was replaced with water. The membrane immersed in water was heated at 125° C. for one hour using a high-pressure steam sterilizer ("HV-85" manufactured by Hirayama Manufacturing Corporation). After replacing water adhering to the membrane with ethanol, the membrane was dried at 60° C. in an oven to obtain a hollow fiber polyvinylidene fluoride membrane. Note that the steps from the extraction step to the drying step were carried out while securing the membrane at a constant length in order to prevent shrinkage.

The polyvinylidene fluoride membrane above was then subjected to a hydrophilization treatment by a grafting method. A reaction liquid was obtained by dissolving hydroxypropyl acrylate (manufactured by Tokyo Kasei Kogyo Co., Ltd., reagent grade) in a 25 vol % aqueous solution of 3-butanol (manufactured by Junsei Kagaku Co., Ltd., special grade) so that the hydroxypropyl acrylate content was 8 vol %, and bubbling nitrogen through the solution at 40° C. for 20 minutes. The polyvinylidene fluoride membrane was irradiated with γ-rays (dose: 100 kGy) from $^{60}$Co (irradiation source) in a nitrogen atmosphere while cooling the polyvinylidene fluoride membrane to –60° C. with dry ice. After irradiation, the membrane was allowed to stand for 15 minutes under a reduced pressure equal to or less than 13.4 Pa, caused to come in contact with the reaction liquid at 40° C., and allowed to stand for one hour. After washing the membrane with ethanol, the membrane was dried at 60° C. for four hours under vacuum to obtain a hollow fiber membrane. A hollow fiber membrane having a molecular weight cut-off of 350,000, an inner diameter of 159 µm, and a thickness of 35 µm was thus obtained.

[Production of Olefin Polymer Membrane]
<Production of Hollow Fiber Membrane (PE)>

25 wt % of high-density polyethylene having a viscosity average molecular weight of 250,000, 20 wt % of high-density polyethylene having a viscosity average molecular weight of 500,000, 40 wt % of dioctyl phthalate, and 15 wt % of a silicic acid fine powder were mixed using a Henschel mixer, and cooled to obtain a powder. The powder was introduced into a twin-screw extruder ("Labo Plastomill Model 50C 150" manufactured by Toyo Seiki Seisaku-Sho, Ltd.) from a hopper, and melt-mixed at 210° C. to obtain a uniform solution. The solution was extruded into a hollow fiber membrane from a double spinneret (inner diameter: 800 µm, outer diameter: 1,200 µm) at a discharge speed of 17 m/min while causing dibutyl phthalate (manufactured by Sanken Kako Co., Ltd., 130° C.) to flow inside the hollow portion at 8 ml/min. The extruded product was cooled and solidified in a water bath maintained at 40° C., and wound at 60 m/min. Dioctyl phthalate was removed by extraction by immersing the membrane in methylene chloride (manufactured by Wako Pure Chemical Industries, Ltd.), and the silicic acid fine powder was removed by elution by immersing the membrane in a 25% sodium hydroxide aqueous solution. After washing the membrane with water, the membrane immersed in water was heated at 120° C. for 20 minutes using a high-pressure steam sterilizer ("HV-85" manufactured by Hirayama Manufacturing Corporation). After replacing water adhering to the membrane with ethanol, the membrane was dried at 60° C. in an oven to obtain a hollow fiber polyethylene membrane. Note that the steps from the extraction step to the drying step were carried out while securing the membrane at a constant length in order to prevent shrinkage.

The polyethylene membrane was then subjected to a hydrophilization treatment by a grafting method. A reaction liquid was obtained by dissolving hydroxypropyl acrylate (manufactured by Tokyo Kasei Kogyo Co., Ltd., reagent grade) in a 25 vol % aqueous solution of 3-butanol (manufactured by Junsei Kagaku Co., Ltd., special grade) so that the hydroxypropyl acrylate content was 8 vol %, and bubbling nitrogen through the solution at 40° C. for 20 minutes. The polyethylene membrane was irradiated with γ-rays (dose: 100 kGy) from $^{60}$Co (irradiation source) in a nitrogen atmosphere while cooling the microporous membrane to −60° C. with dry ice. After irradiation, the membrane was allowed to stand for 15 minutes under a reduced pressure equal to or less than 13.4 Pa, caused to come in contact with the reaction liquid at 40° C., and allowed to stand for one hour. After washing the membrane with ethanol, the membrane was dried at 60° C. for four hours under vacuum to obtain a hollow fiber membrane. A hollow fiber membrane having a molecular weight cut-off of 290,000, an inner diameter of 176 μm, and a thickness of 36 μm was thus obtained.

[Production of Vinyl Alcohol Polymer Membrane]
<Production of Hollow Fiber Membrane (PVA)>

15 wt % of an EVA-based polymer ("EVAL EC-F100A" manufactured by Kuraray Ltd.) (ethylene content: 32 mol %, degree of saponification 99%), 84 wt % of dimethyl sulfoxide (DMSO), and 1 wt % of water were dissolved at 90° C. The mixture was poured into a membrane raw material solution reactor (5000×10$^{-6}$ m$^3$). An operation of reducing the pressure inside the reactor and replacing the atmosphere inside the reactor with nitrogen was repeated five times with stirring. After confirming that a membrane raw material solution was obtained, stirring was stopped. The solution was then defoamed under reduced pressure. The pressure inside the reactor was then increased to atmospheric pressure to obtain a spinning membrane raw material solution maintained at 70° C.

A 30 wt % DMSO aqueous solution was prepared as an internal coagulation liquid. The internal coagulation liquid and the membrane raw material solution were passed through a double spinneret (inner diameter: 100 μm, slit width: 50 μm, outer diameter: 300 μm) maintained at 65° C. The flow rate was appropriately adjusted corresponding to the take-up speed during spinning. The resulting hollow fiber membrane was passed through an air gap (0.6 m), introduced into an external coagulation liquid (30 wt % DMSO aqueous solution) contained in a coagulation bath (15° C.), and wound using a winder. The take-up speed was 2,400 m/h to 4,800 m/h. The resulting hollow fiber membrane washed with water, and subjected to a wet-heat treatment, acetone replacement, drying, and a fixed-length heat treatment to obtain a hollow fiber membrane. A hollow fiber membrane having a molecular weight cut-off of 380,000, an inner diameter of 158 μm, and a thickness of 41 μm was thus obtained.

[Production of Cellulose Polymer Membrane]
<Production of Hollow Fiber Membrane (CEL)>

Cotton linters (average molecular weight: 150,000) were dissolved in a cuprammonium solution, followed by filtration and defoaming, to obtain a spinning raw solution having a cellulose concentration of 5.7 wt %, an ammonia concentration of 4.0 wt %, and a copper concentration of 2.1 wt %. The spinning raw solution was discharged from an outer nozzle of a circular double spinneret at 2.0 cc/min, and an internal coagulation liquid having an acetone concentration of 45 wt % and an ammonia concentration of 0.1 wt % was discharged from a center nozzle of the double spinneret at 0.7 cc/min.

The discharged spinning raw solution was introduced into an apparatus that was provided with a thin tube and filled with an external coagulation liquid having an acetone concentration of 55 wt % and an ammonia concentration of 0.7 wt % to effect microphase separation and coagulation, and wound around a flat frame at 5 m/min. The diameter of the thin tube was 7 mm, the flow rate of the external liquid was 1.0 m/min, the driving direction change roll speed was 4.7 m/min, the rate-limiting roll speed was 5 m/min, and the flat frame speed was 5 m/min. Water at 30° C. was used as the winding bath component. After winding the hollow fibers for 40 minutes, the hollow fibers were immersed in water at 30° C. for 60 minutes. The wound hollow fibers were regenerated using a 3 wt % sulphuric acid aqueous solution, and washed with water. After replacing water contained in the hollow fiber membrane with methanol, the membrane was dried at 50° C. under vacuum to obtain a hollow fiber membrane. A hollow fiber membrane having a molecular weight cut-off of 390,000, an inner diameter of 181 μm, and a thickness of 33 μm was thus obtained.

<Preparation of Bovine Immunoglobulin Monomer/Dimer Fractionation Performance-Evaluation Solution>

A 5% bovine immunoglobulin solution (bovine serum γ-globulin manufactured by Invitrogen), from which insoluble components were removed using "Planova 75N" (manufactured by Asahi Kasei Medical Co., Ltd.), was diluted with a PBS (manufactured by Nissui Pharmaceutical Co., Ltd.) to prepare a bovine immunoglobulin solution having a given concentration (fractionation performance-evaluation solution). The content of the bovine immunoglobulin monomer and the content of the bovine immunoglobulin dimer measured by GPC were 91% and 8%, respectively.

<Preparation of Human Immunoglobulin Monomer/Dimer Fractionation Performance-Evaluation Solution>

A 5% human immunoglobulin solution ("Glovenin-I-Nichiyaku" manufactured by Nihon Pharmaceutical Co., Ltd.) was subjected to a pH treatment. Insoluble components were removed from the solution by centrifugation. After filtering the supernatant using a microfilter (0.2 μm), the solution was diluted with a PBS (manufactured by Nissui Pharmaceutical Co., Ltd.) to prepare a human immunoglobulin solution having a given concentration (fractionation performance evaluation solution). The content of the human immunoglobulin monomer and the content of the human immunoglobulin dimer measured by GPC were 91% and 8%, respectively.

<Production of Anti-SCF Antibody>
(1) Production of Immunogen

A cDNA of an SCF that was isolated from a cDNA library of HeLa cells highly expressing an SCF was introduced into an animal cell expression vector pBCMGS-neo. The vector was transfected into a mouse fibroblast Balb/3T3 cell line. The resulting transfectant was used as an immunogen.

(2) Production of Hybridoma
(a) Immunization

The above transfectant was intraperitoneally administered to an 8-week-old Balb/c mouse (female) at intervals of two weeks. The effect of immunization was evaluated by reactivity between a blood serum of the peripheral blood sampled from the tail vein of the mouse and the immunogen. After confirming the effect, final immunization and cell fusion were carried out.

(b) Cell Fusion

Four days after final immunization, the splenic cell of the immunized mouse and a mouse myeloma derived cell line SP-2 were fused according to a known method.

(c) Screening of Anti-SCF Antibody-Producing Hybridoma

As a method of screening an anti-SCF antibody-producing hybridoma, an indirect antibody method using the transfectant and its parent cell line (Balb/3T3) as an antigen was used. A hybridoma that produced an antibody that bound to the transfectant, but did not bind to the parent cell line (Balb/3T3), was selected and cloned.

(d) Purification of Antibody

The culture supernatant of the SCF expressing clone was concentrated by ultrafiltration, and mixed with an equal amount of buffer (BioRad Protein MAPS buffer). Protein A-Sepharose CL-4B (Pharmacia) was equilibrated using the buffer, and the mixture was allowed to flow through a column so that the antibody bound. The column was then washed using the buffer. Elution was done by passing a 0.2 M glycine-HCl buffer (pH: 3.0) through a column to obtain an antibody fraction. A purification operation was performed in the order of DEAE-Sepharose FF (GE healthcare), Phenyl-Sepharose HP (GE healthcare), and Spephadex-G75 (GE healthcare) to isolate the anti-SCF antibody.

Then, the anti-SCF antibody was subjected to a pH treatment. Insoluble components were removed by centrifugation. After filtering the supernatant using a microfilter (0.2 μm), the solution was diluted with a PBS (manufactured by Nissui Pharmaceutical Co., Ltd.) to prepare a human immunoglobulin solution having a given concentration (fractionation performance-evaluation solution). The content of the human immunoglobulin monomer and the content of the human immunoglobulin dimer measured by GPC were 96% and 4%, respectively.

<Measurement of Molecular Weight Cut-Off>

1 wt % bovine albumin (manufactured by Sigma-Aldrich, molecular weight: 60,000), bovine γ-globulin (manufactured by Invitrogen, molecular weight: 150,000), and ferritin (manufactured by Sigma-Aldrich, molecular weight: 450,000) were subjected to constant-pressure dead-end filtration (0.010 MPa) using each of the ultrafiltration membranes. The amount of each of albumin, γ-globulin, and ferritin contained in the immunoglobulin permeation solution that passed through the ultrafiltration membrane within five minutes after starting filtration was measured, and the trapping rate of each of the proteins trapped by the membrane was calculated. A calibration curve of the molecular weight and the trapping rate of each of the proteins was drawn, and the molecular weight at a trapping rate of 90% was determined from the calibration curve, and taken as the molecular weight cut-off.

<Calculation of Throughput, Permeation Amount, Permeability, and Permeability Ratio>

The throughput, permeation amount, permeability, and permeability ratio may be calculated from the results obtained by high-performance liquid chromatography, nuclear magnetic resonance spectroscopy, mass spectrometry, IR spectroscopy, or the like. Note that the method is not limited thereto. In the present invention, the throughput, permeation amount, permeability, and permeability ratio were calculated as follows. The immunoglobulin concentration was calculated by measuring the absorbance at a wavelength of 280 nm using an absorption spectrometer. The weight ratio of immunoglobulin dimers to immunoglobulin monomers was determined from the absorption peak area ratio at a wavelength of 280 nm measured by high-performance liquid chromatography (G3000 SWXL×2, SC8020 system, UV8020 detector (manufactured by Tosoh Corp.)).

(Calculation of Permeability)

The total throughput of the immunoglobulin is calculated by the following formulas (13) to (15).

$$W = W(\text{Mo}) + W(\text{Ag}) \tag{13}$$

$$W(\text{Mo}) = V1 \times A1/A \times G1(\text{Mo})/100 - V2 \times A2/A \times G2(\text{Mo})/100 \tag{14}$$

$$W(\text{Ag}) = V1 \times A1/A \times G1(\text{Ag})/100 - V2 \times A2/A \times G2(\text{Ag})/100 \tag{15}$$

W: Throughput (g) of immunoglobulin made to pass through the membrane

W(Mo): Throughput (g) of immunoglobulin monomer made to pass through the membrane W(Ag): Throughput (g) of immunoglobulin dimer made to pass through the membrane A: Absorbance (Abs) of immunoglobulin solution at 1 g/L V1: Volume (L) of immunoglobulin stock solution before filtration A1: Absorbance (Abs) of immunoglobulin stock solution before filtration G1(Mo): Monomer content (%) in immunoglobulin stock solution before filtration G1(Ag): Dimer content (%) immunoglobulin stock solution before filtration V2: Volume (1) of immunoglobulin stock solution after filtration A2: Absorbance (Abs) of immunoglobulin stock solution after filtration G2(Mo): Monomer content (%) in immunoglobulin stock solution after filtration G2(Ag): Dimer content (%) in immunoglobulin stock solution after filtration When the volume of the immunoglobulin stock solution before filtration is large, and the throughput is small, the dimer/monomer ratio in the immunoglobulin solution changes to only a small extent. Therefore, the throughput may be approximately calculated by the following formulas (16) and (17).

$$W(\text{Mo}) = (V1 \times A1 - V2 \times A2)/A \times G1(\text{Mo})/100 \tag{16}$$

$$W(\text{Ag}) = (V1 \times A1 - V2 \times A2)/A \times G1(\text{Ag})/100 \tag{17}$$

Then, the permeation amount P(Mo) of immunoglobulin monomers and the permeation amount P(Ag) of immunoglobulin dimers were calculated by the following formulas (18) and (19).

$$P(\text{Mo}) = V3 \times A3/A \times G3(\text{Mo})/100 \tag{18}$$

P(Mo): Permeation amount (g) of immunoglobulin monomer passed through the membrane P(Ag): Permeation amount (g) of immunoglobulin dimer passed through the membrane A: Absorbance (Abs) of immunoglobulin solution at 1 g/L V3: Volume (L) of immunoglobulin permeation solution A3: Absorbance (Abs) of immunoglobulin permeation solution G3(Mo): Monomer content (%) in immunoglobulin permeation solution G3(Ag): Dimer content (%) in immunoglobulin permeation solution Immunoglobulin monomer permeability and immunoglobulin dimer permeability were calculated by the following formulas (20) and (21), and the permeability ratio (fractionation performance) was calculated by the following formula (22).

Monomer permeability (%)=$P(\text{Mo})/W(\text{Mo})\times 100$ (20)

Dimer permeability (%)=$P(\text{Ag})/W(\text{Ag})\times 100$ (21)

Permeability ratio=dimer permeability/monomer permeability (22)

<Evaluation of Aggregation Inhibiting Effect>

An aggregation inhibitor was added to an immunoglobulin solution so that a given concentration was obtained. A cross-flow filtration experiment was performed for three hours using a PSf-1 filter (0.02 m²). The turbidity due to the immunoglobulin was measured before and after the filtration experiment to evaluate the immunoglobulin aggregation inhibiting effect.

The cross-flow filtration experiment was performed under the following conditions. Specifically, 300 mL of an immunoglobulin solution (10 g/L) was provided in a filtration apparatus. Cross-flow filtration was performed at 25° C. for 2.5 hours so that the immunoglobulin solution supply rate was 10 cm/sec and the average value of the inlet filtration pressure and the outlet filtration pressure was 0.027 MPa. A solution that was not filtered was returned to the immunoglobulin stock solution. Since the immunoglobulin stock solution is concentrated as filtration proceeds, the immunoglobulin concentration was maintained constant while measuring the absorbance (Abs) of the immunoglobulin stock solution at a wavelength of 280 nm using UV-1600 (manufactured by Shimadzu Corporation) every 15 minutes. A solution containing an aggregation inhibitor at the same concentration as the immunoglobulin stock solution was used so that the concentration of the aggregation inhibitor in the system did not change. The turbidity of the solution was measured using a Lacombe tester turbidity meter "TN-100" (manufactured by AS ONE Corporation), and the aggregation inhibiting effect was calculated by the following formula (23). A high value indicates a high aggregation inhibiting effect.

Aggregation inhibiting effect=$[1-(Ba-Bo)/(Aa-Ao)]\times 100$ (23)

Ba=Turbidity (NTU) of immunoglobulin stock solution after filtration experiment with aggregation inhibitor Bo=Turbidity (NTU) of immunoglobulin stock solution before filtration experiment with aggregation inhibitor Aa=Turbidity (NTU) of immunoglobulin stock solution after filtration experiment without aggregation inhibitor Ao=Turbidity (NTU) of immunoglobulin stock solution before filtration experiment without aggregation inhibitor <Calculation of Concentration Rate in Immunoglobulin Concentration Step>

The concentration rate in the immunoglobulin concentration step was calculated by the following formulas (24) to (26), using the concentration of the immunoglobulin permeation solution obtained by the separation step and the concentration of the concentrated solution obtained by the concentration step.

Concentration rate=$C4/C3$ (24)

$C3=A3/A$ (25)

$C4=A4/A$ (26)

C3: Concentration (g/L) of immunoglobulin permeation solution

C4: Concentration (g/L) of concentrated immunoglobulin solution

A3: Absorbance (Abs) of immunoglobulin permeation solution

A4: Absorbance (Abs) of concentrated immunoglobulin solution

A: Absorbance (Abs) of immunoglobulin solution at 1 g/L

Example 1

The hollow fiber membranes (PSf-1) were bundled so that the total hollow cross-sectional area was 0.005 m² to obtain a fiber bundle for evaluating the human immunoglobulin monomer/dimer fractionation performance. The fiber bundle was connected to the cross-flow filtration apparatus shown in FIG. 3.

A human immunoglobulin solution (0.01 g/L) containing lysine hydrochloride (50 g/L) was placed in the apparatus. The supply pump 2 (3) was rotated while adjusting the control valve 1 (7) so that the linear velocity inside the hollow fiber membrane was 10 cm/sec and the average outlet pressure was 0.010 MPa. A PBS aqueous solution containing lysine hydrochloride (50 g/L) contained in the diluent tank (1) was added to the immunoglobulin stock solution tank (4) so that the concentration of the human immunoglobulin was constant during filtration. A cake layer was formed on the surface of the membrane by filtering the immunoglobulin solution for 20 minutes. A human immunoglobulin solution (2.5 g/L) was then filtered to measure the ratio of immunoglobulin dimer permeability to immunoglobulin monomer permeability (immunoglobulin dimer permeability/immunoglobulin monomer permeability) for one minute.

A human immunoglobulin solution (0.1 g/L, 1 g/L, and 10 g/L), or the diluent (blank) was filtered in the same manner as described above. A human immunoglobulin solution (2.5 g/L) was then filtered to measure the ratio of immunoglobulin dimer permeability to immunoglobulin monomer permeability (immunoglobulin dimer permeability/immunoglobulin monomer permeability) for five minutes.

Figure 6:
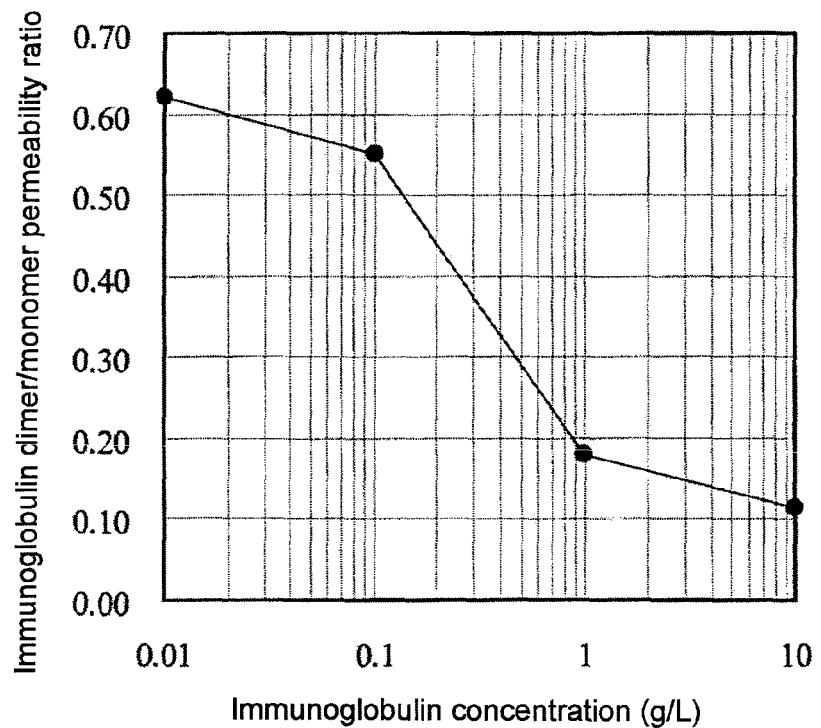
FIG. 6 is a view showing an example of the relationship between the immunoglobulin concentration and immunoglobulin dimer/monomer permeability ratio.

The ratio of immunoglobulin dimer permeability to immunoglobulin monomer permeability (permeability ratio) when forming a cake layer using the diluent (0 g/L), the human immunoglobulin solution (0.01 g/L and 0.1 g/L) was 0.62, 0.62, and 0.55, respectively (see FIG. 6). Specifically, a cake layer that enabled separation of immunoglobulin monomers and immunoglobulin dimers was not formed within a short time when the concentration of the human immunoglobulin solution was less than 1 g/L. On the other hand, the permeability ratio when forming a cake layer using the human immunoglobulin solution (1 g/L and 10 g/L) was 0.18 and 0.12, respectively. This showed that a cake layer that enabled separation of immunoglobulin monomers and immunoglobulin dimers was formed within a short time.

As is clear from the above results, it was found that the concentration of the human immunoglobulin solution must be 1 g/L or more in order to form a cake layer that enables separation of immunoglobulin monomers and immunoglobulin dimers (i.e., the ratio of immunoglobulin dimer permeability to immunoglobulin monomer permeability is 0.2 or less).

Example 2

The hollow fiber membranes (PSf-1) were bundled so that the total hollow cross-sectional area was 0.01 m² to obtain a fiber bundle for evaluating the human immunoglobulin monomer/dimer fractionation performance. The fiber bundle was connected to the cross-flow filtration apparatus shown in FIG. 3.

A human immunoglobulin solution (10 g/L) containing lysine hydrochloride (50 g/L) was placed in the apparatus.

The supply pump 2 (3) was rotated while adjusting the control valve 1 (7) so that the linear velocity inside the hollow fiber membrane was 10 cm/sec and the outlet pressure was 0.010 MPa. A PBS aqueous solution containing lysine hydrochloride (50 g/L) contained in the diluent tank (1) was added to the immunoglobulin stock solution tank (4) so that the concentration of the human immunoglobulin was constant during filtration. The immunoglobulin solution was subjected to cross-flow filtration at 25° C. for five hours. The permeation amount of the human immunoglobulin monomer measured by GPC was 156 g/m$^2$. A human immunoglobulin solution (30 g/L, 50 g/L and 100 g/L) were filtered in the same manner as described above. The permeation amount of the human immunoglobulin solution within five hours after starting filtration was calculated to be 207 g/m$^2$, 244 g/m$^2$, and 367 g/m$^2$, respectively. The ratio of the human immunoglobulin dimer permeability to the human immunoglobulin monomer permeability (human immunoglobulin dimer permeability/human immunoglobulin monomer permeability (permeability ratio)) was calculated to be 0.10, 0.13, 0.14, and 0.17, respectively.

Figure 7:
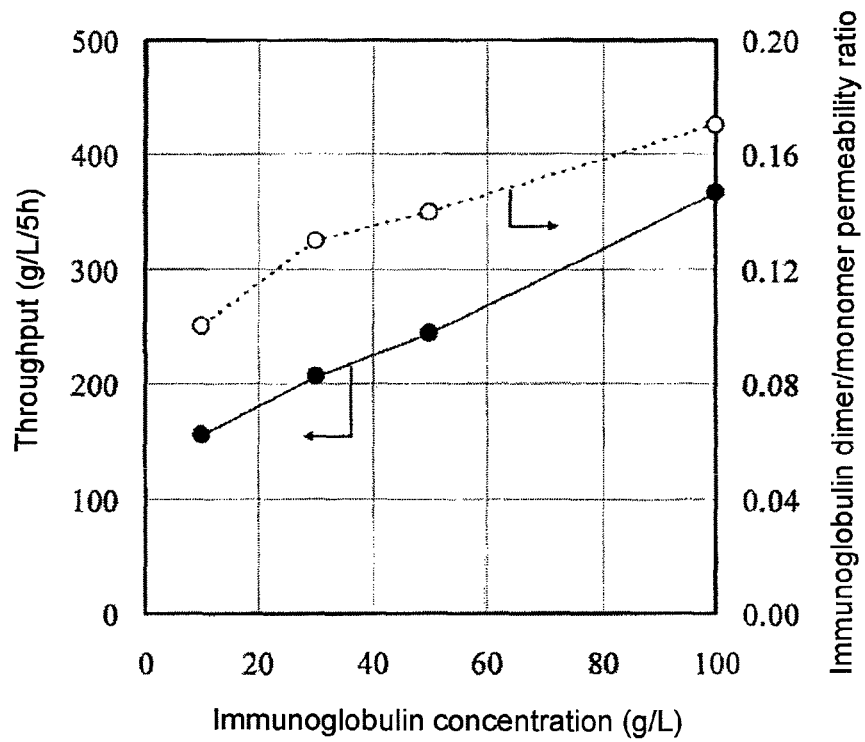
FIG. 7 is a view showing an example of the relationship between the immunoglobulin concentration, the throughput, and immunoglobulin dimers/monomer permeability ratio.

As is clear from the above results (see FIG. 7), the ratio of the human immunoglobulin dimer permeability to the human immunoglobulin monomer permeability was 0.20 or more and the dimer content of the immunoglobulin permeation solution was high when the concentration of the human immunoglobulin solution was 150 g/L or more. Therefore, when the amount of immunoglobulin dimer contained in the immunoglobulin stock solution is small, the upper limit of the concentration of the immunoglobulin is 150 g/L or less in order to implement stable filtration so that immunoglobulin dimer content in the permeation solution is 1% or less, taking account of the fact that the ratio of immunoglobulin dimer permeability to immunoglobulin monomer permeability may be 0.30 or less.

Example 3

Figure 8:
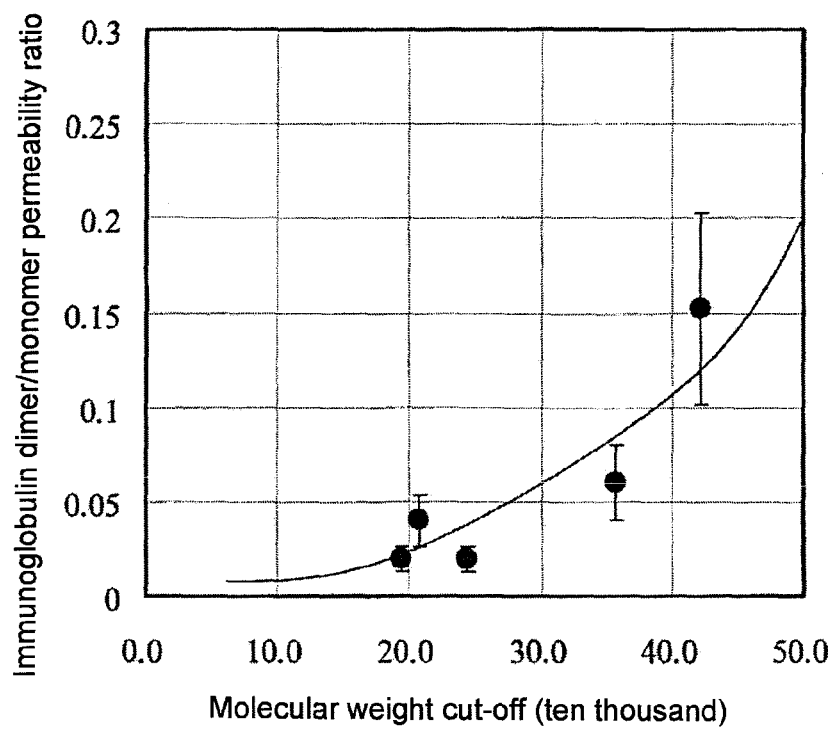
FIG. 8 is a view showing an example of the molecular weight cut-off of an ultrafiltration membrane and the fractionation performance.

Polysulfone-based hollow fiber membranes having a molecular weight cut-off of 45,000, 190,000, 210,000, 240,000, 360,000, and 420,000 were produced by appropriately changing the amount of purified water and the amount of DMAc in the internal coagulation liquid. The hollow fiber membranes were bundled so that the total hollow cross-sectional area was 0.005 m$^2$ to obtain a fiber bundle for evaluating the human immunoglobulin monomer/dimer fractionation performance. The fiber bundle was connected to the cross-flow filtration apparatus shown in FIG. 3. A human immunoglobulin solution (10 g/L) containing lysine hydrochloride (50 g/L) was placed in the apparatus. The supply pump 2 (3) was rotated while adjusting the control valve 1 (7) so that the linear velocity inside the hollow fiber membrane was 10 cm/sec and the outlet pressure was 0.010 MPa. A PBS aqueous solution containing lysine hydrochloride (50 g/L) contained in the diluent tank (1) was added to the immunoglobulin stock solution tank (4) so that the concentration of the human immunoglobulin was constant during filtration. The immunoglobulin solution was subjected to cross-flow filtration at 25° C. for five hours. The human immunoglobulin permeation solution was subjected to GPC, and the ratio of the human immunoglobulin dimer permeability to the human immunoglobulin monomer permeability (human immunoglobulin dimer permeability/human immunoglobulin monomer permeability) was calculated. The human immunoglobulin could not pass through the polysulfone polymer membrane having a molecular weight cut-off of 45,000. The ratio of the human immunoglobulin dimer permeability to the human immunoglobulin monomer permeability of the polysulfone polymer membranes having a molecular weight cut-off of 190,000, 210,000, 240,000, 360,000, and 420,000 was 0.02, 0.04, 0.02, 0.06, and 0.15, respectively. As is clear from the above results (see FIG. 8), the human immunoglobulin monomer does not pass through the polysulfone polymer membrane when the molecular weight cut-off is less than 100,000, and the ratio of the human immunoglobulin dimer permeability to the human immunoglobulin monomer permeability is more than 0.2 (i.e., sufficient fractionation performance is not obtained) when the molecular weight cut-off is 500,000 or more. Therefore, the molecular weight cut-off must be 100,000 or more and less than 500,000 in order to obtain high permeability and high fractionation performance.

Example 4

The hollow fiber membranes (PSf-1) were bundled so that the total hollow cross-sectional area was 0.01 m$^2$ to obtain a fiber bundle for evaluating the bovine immunoglobulin monomer/dimer fractionation performance. The fiber bundle was connected to the cross-flow filtration apparatus shown in FIG. 3. A supply pump 1 (3) was rotated while adjusting a control valve 1 (7) so that the linear velocity inside the hollow fiber membrane was 10 cm/sec and the average value of the inlet pressure and the outlet pressure was 0.027 MPa. Since the concentration of the fractionation performance evaluation solution increases as cross-flow filtration proceeds, a PBS aqueous solution contained in the diluent tank (1) was added to the immunoglobulin stock solution tank (4) so that the concentration of the bovine immunoglobulin was constant (10 g/L). The immunoglobulin solution was subjected to cross-flow filtration at 25° C. for five hours. The content of the bovine immunoglobulin in the immunoglobulin stock solution and the immunoglobulin permeation solution was measured by an absorption spectrometer, and the content of the bovine immunoglobulin monomer and the bovine immunoglobulin dimer was measured by GPC. As shown in Table 1, the monomer permeation amount was 126 g/m$^2$, and the dimer permeation amount was 1.8 g/m$^2$. The bovine immunoglobulin monomer permeability and the bovine immunoglobulin dimer permeability were respectively 83.7% and 13.7%, and the permeability ratio was 0.16.

Example 5

The hollow fiber membranes (PSf-2) were bundled so that the total hollow cross-sectional area was 0.02 m$^2$ to obtain a fiber bundle for evaluating the human immunoglobulin monomer/dimer fractionation performance. A human immunoglobulin solution containing a human immunoglobulin (10 g/L) and lysine hydrochloride (50 g/L) was prepared. The fiber bundle and 100 ml of the human immunoglobulin solution were connected to the cross-flow filtration apparatus shown in FIG. 3. The supply pump 2 (3) was rotated while adjusting the control valve 1 (7) so that the linear velocity inside the hollow fiber membrane was 10 cm/sec and the outlet pressure was 0.010 MPa. Since the concentration of the human immunoglobulin solution increases as cross-flow filtration proceeds, a PBS aqueous solution containing lysine hydrochloride (50 g/L) contained in the diluent tank (1) was added to the immunoglobulin stock solution tank (4) so that the concentration of the human immunoglobulin was constant (10 g/L). The immunoglobulin solution was subjected to cross-flow filtration at 25° C. for 120 minutes. The content of the human immunoglobulin monomer and the human immunoglobulin dimer in the immunoglobulin permeation solution was measured by GPC. As shown in Table 1, the monomer permeation amount was 44 g/m², and the dimer permeation amount was 0.4 g/m². The human immunoglobulin monomer permeability and the human immunoglobulin dimer permeability were respectively 97.0% and 9.7%, and the permeability ratio (fractionation performance) was 0.10.

Example 6

Figure 9:
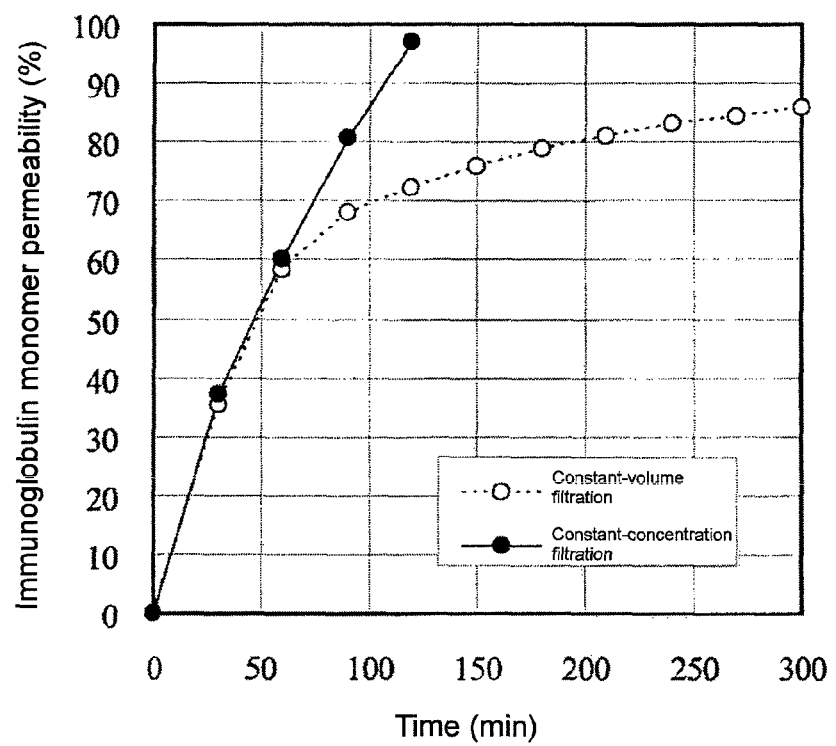
FIG. 9 is a view showing an example of the relationship between the filtration time and immunoglobulin monomer permeability.

An immunoglobulin solution was subjected to cross-flow filtration in the same manner as in Example 5, except that a PBS aqueous solution was added as a diluent so that the concentration of the solution in the immunoglobulin stock solution tank (4) was constant. FIG. 9 shows the relationship between the time and immunoglobulin monomer permeability. The human immunoglobulin monomer permeability and the human immunoglobulin dimer permeability after 300 minutes were respectively 85.7% and 5.0%, and the permeability ratio was 0.06.

Example 7

The hollow fiber membranes (PSf-2) were bundled so that the total hollow cross-sectional area was 0.02 m² to obtain a fiber bundle for evaluating the human immunoglobulin monomer/dimer fractionation performance. A human immunoglobulin solution containing a human immunoglobulin (30 g/L) and arginine hydrochloride (50 g/L) was prepared. The fiber bundle and 100 ml of the human immunoglobulin solution were connected to the cross-flow filtration apparatus shown in FIG. 3. The supply pump 2 (3) was rotated while adjusting the control valve 1 (7) so that the linear velocity inside the hollow fiber membrane was 10 cm/sec and the outlet pressure was 0.010 MPa. Since the concentration of the human immunoglobulin solution increases as cross-flow filtration proceeds, a PBS aqueous solution containing lysine hydrochloride (50 g/L) contained in the diluent tank (1) was added to the immunoglobulin stock solution tank (4) so that the concentration of the bovine immunoglobulin was constant (30 g/L). The immunoglobulin solution was subjected to cross-flow filtration at 25° C. until the entire solution was filtered. The content of the human immunoglobulin monomer and the human immunoglobulin dimer in the immunoglobulin permeation solution was measured by GPC. As shown in Table 1, the monomer permeation amount was 132 g/m², and the dimer permeation amount was 1.6 g/m². The human immunoglobulin monomer permeability and the human immunoglobulin dimer permeability were respectively 97.0% and 13.5%, and the permeability ratio (fractionation performance) was 0.14.

Example 8

The hollow fiber membranes (PSf-2) were bundled so that the total hollow cross-sectional area was 0.02 m² to obtain a fiber bundle for evaluating the SCF monoclonal antibody monomer/dimer fractionation performance. An SCF monoclonal antibody solution containing an SCF monoclonal antibody (5 g/L) and lysine hydrochloride (50 g/L) was prepared. The fiber bundle and 150 ml of the SCF monoclonal antibody solution were connected to the cross-flow filtration apparatus shown in FIG. 3. The supply pump 2 (3) was rotated while adjusting the control valve 1 (7) so that the linear velocity inside the hollow fiber membrane was 10 cm/sec and the outlet pressure was 0.010 MPa. Since the concentration of the SCF monoclonal antibody solution increases as cross-flow filtration proceeds, a PBS aqueous solution containing arginine hydrochloride (50 g/L) contained in the diluent tank (1) was added to the immunoglobulin stock solution tank (4) so that the concentration of the SCF monoclonal antibody was constant (5 g/L). The SCF monoclonal antibody solution was subjected to cross-flow filtration at 25° C. until the entire solution was filtered. The content of the SCF monoclonal antibody monomer and the SCF monoclonal antibody dimer in the immunoglobulin permeation solution was measured by GPC. As shown in Table 1, the monomer permeation amount was 35 g/m², and the dimer permeation amount was 0.2 g/m². The bovine immunoglobulin monomer permeability and the bovine immunoglobulin dimer permeability were respectively 96.0% and 14.4%, and the permeability ratio (fractionation performance) was 0.15.

Example 9

The hollow fiber membranes (PSf-3) were bundled so that the total hollow cross-sectional area was 0.02 m² to obtain a fiber bundle for evaluating the bovine immunoglobulin monomer/dimer fractionation performance. A bovine immunoglobulin solution containing a bovine immunoglobulin (10 g/L) and arginine hydrochloride (50 g/L) was prepared. The fiber bundle and 300 ml of the bovine immunoglobulin solution were connected to the cross-flow filtration apparatus shown in FIG. 3. The supply pump 2 (3) was rotated while adjusting the control valve 1 (7) so that the linear velocity inside the hollow fiber membrane was 10 cm/sec and the outlet pressure was 0.010 MPa. Since the concentration of the bovine immunoglobulin solution increases as cross-flow filtration proceeds, a PBS aqueous solution containing arginine hydrochloride (50 g/L) contained in the diluent tank (1) was added to the immunoglobulin stock solution tank (4) so that the concentration of the bovine immunoglobulin was constant (10 g/L). The immunoglobulin solution was subjected to cross-flow filtration at 25° C. until the entire solution was filtered. The content of the bovine immunoglobulin monomer and the bovine immunoglobulin dimer in the immunoglobulin permeation solution was measured by GPC. As shown in Table 1, the monomer permeation amount was 126 g/m², and the dimer permeation amount was 1.4 g/m². The bovine immunoglobulin monomer permeability and the bovine immunoglobulin dimer permeability were respectively 92.0% and 12.0%, and the permeability ratio (fractionation performance) was 0.13.

Comparative Example 1

The permeation amount, permeability, and permeability ratio were calculated in the same manner as in Example 4, except for using the hollow fiber membrane (PSf-4) instead of the hollow fiber membrane (PSf-1). As shown in Table 1, the monomer permeation amount was 201 g/m², and the dimer permeation amount was 10.4 g/m². The bovine immunoglobulin monomer permeability and the bovine immunoglobulin dimer permeability were respectively 92.5% and 54.2%, and the permeability ratio (fractionation performance) was 0.59.

Comparative Example 2

The permeation amount, permeability, and permeability ratio were calculated in the same manner as in Example 4, except for using the hollow fiber membrane (PSf-5) instead of the hollow fiber membrane (PSf-1). As shown in Table 1, the monomer permeation amount was 363 g/m², and the dimer permeation amount was 30.9 g/m². The bovine immunoglobulin monomer permeability and the bovine immunoglobulin dimer permeability were respectively 94.2% and 91.2%, and the permeability ratio (fractionation performance) was 0.97.

Example 10

The hollow fiber membranes (PSf-6) were bundled so that the total hollow cross-sectional area was 0.01 m² to obtain a fiber bundle for evaluating the bovine immunoglobulin monomer/dimer fractionation performance. The fiber bundle was connected to the cross-flow filtration apparatus shown in FIG. 3. A supply pump 2 (3) was rotated while adjusting a control valve 1 (7) so that the linear velocity inside the hollow fiber membrane was 100 cm/sec and the average value of the inlet pressure and the outlet pressure was 0.1 MPa. Since the concentration of the fractionation performance evaluation solution increases as cross-flow filtration proceeds, a PBS aqueous solution contained in the diluent tank (1) was added to the immunoglobulin stock solution tank (4) by rotating the supply pump 1 (2) so that the concentration of the bovine immunoglobulin was constant (10 g/L). The immunoglobulin solution was subjected to cross-flow filtration at 25° C. for five hours. The content of the bovine immunoglobulin in the immunoglobulin stock solution and the immunoglobulin permeation solution was measured by an absorption spectrometer, and the content of the bovine immunoglobulin monomer and the bovine immunoglobulin dimer was measured by GPC. As shown in Table 1, the monomer permeation amount was 875 g/m², and the dimer permeation amount was 12.4 g/m². The bovine immunoglobulin monomer permeability and the bovine immunoglobulin dimer permeability were respectively 90.3% and 14.6%, and the permeability ratio (fractionation performance) was 0.16.

Comparative Example 3

Figure 5:
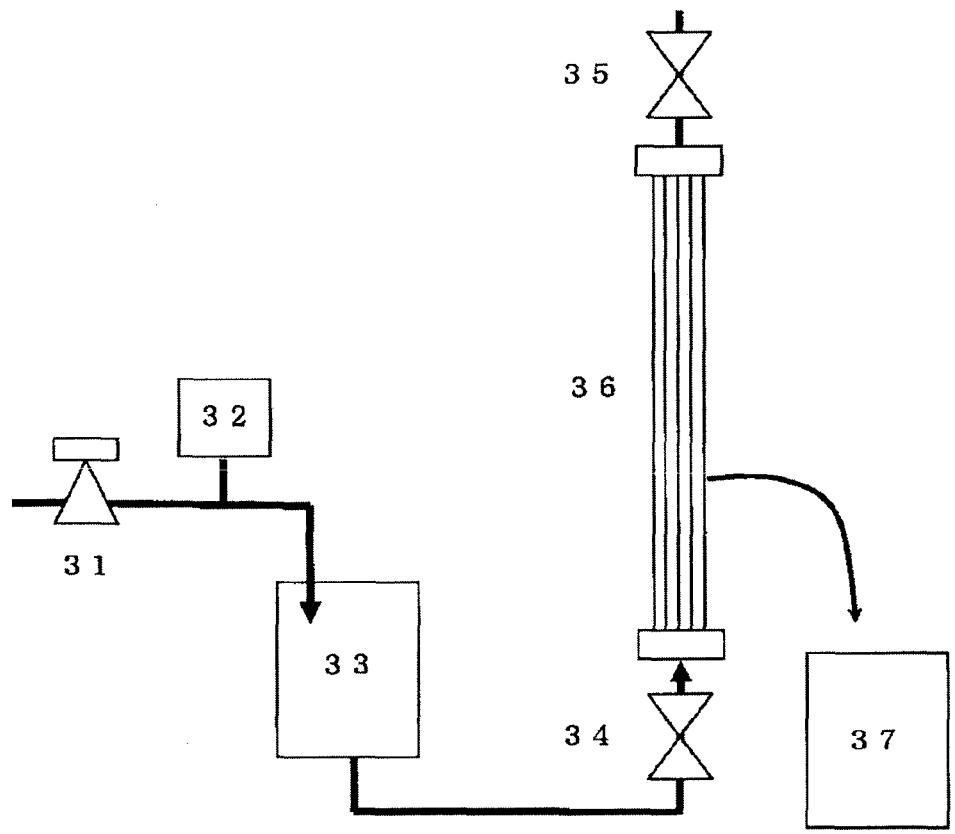
FIG. 5 is a view showing an example of dead-end filtration method.

An immunoglobulin solution was filtered using a fiber bundle prepared in the same manner as in Example 10 and the dead-end filtration apparatus shown in FIG. 5. The pressure regulator (31) was operated in a state in which the valve 1 (34) was opened and the valve 2 (35) was closed. The immunoglobulin solution was subjected to dead-end filtration while setting the inlet pressure to 0.1 MPa. In this case, high permeability was achieved in the initial stage of filtration. However, permeability gradually decreased so that an immunoglobulin permeation solution was not obtained. Specifically, a continuous dead-end filtration operation could not be performed steadily. The monomer permeation amount was 413 g/m², and the dimer permeation amount was 28.8 g/m². As shown in Table 1, the bovine immunoglobulin monomer permeability and the bovine dimer permeability were respectively 88.2% and 69.8%, and the permeability ratio (fractionation performance) was 0.79 (i.e., the fractionation performance deteriorated).

TABLE 1

| | | Example 4 | Example 5 | Example 6 | Example 7 | Example 8 | Example 9 |
|---|---|---|---|---|---|---|---|
| Membrane | Type | PSf-1 | PSf-2 | PSf-2 | PSf-2 | PSf-2 | PSf-3 |
| | Molecular weight cut-off | 300,000 | 360,000 | 360,000 | 360,000 | 360,000 | 240,000 |
| Hydrophilic agent | Type | PVP | PVP | PVP | PVP | PVP | PVP |
| Membrane structure | Inner diameter (μm) | 151 | 207 | 207 | 207 | 207 | 199 |
| | Thickness (μm) | 30 | 41 | 41 | 41 | 41 | 37 |
| Immunoglobulin | Type | b-IgG | h-IgG | h-IgG | h-IgG | SCF | b-IgG |
| | Concentration (g/L) | 10 | 10 | 10 | 30 | 10 | 10 |
| | Monomer content (%) | 91 | 91 | 91 | 91 | 96 | 91 |
| | Dimer content (%) | 8 | 8 | 8 | 8 | 4 | 8 |
| Aggregation inhibitor | Lysine hydrochloride (g/L) | 0 | 50 | 50 | 0 | 50 | 0 |
| | Arginine hydrochloride (g/L) | 0 | 0 | 0 | 50 | 0 | 50 |
| Filtration method | | CF | CF | CF | CF | CF | CF |
| Linear velocity (cm/sec) | | 10 | 10 | 10 | 10 | 10 | 10 |
| Pressure (MPa) | | 0.027 | 0.01 | 0.01 | 0.01 | 0.01 | 0.01 |
| Throughput (g/m²) | | 165 | 50 | 50 | 150 | 37.5 | 150 |
| Monomer permeation amount (g/m²) | | 126 | 44 | 39 | 132 | 35 | 126 |
| Dimer permeation amount (g/m²) | | 1.8 | 0.4 | 0.2 | 1.6 | 0.2 | 1.4 |
| Monomer permeability (%) | | 83.7 | 97.0 | 85.7 | 97.0 | 96.0 | 92.0 |
| Dimer permeability (%) | | 13.7 | 9.7 | 5.0 | 13.5 | 14.4 | 12.0 |
| Permeability ratio (dimer/monomer) | | 0.16 | 0.10 | 0.06 | 0.14 | 0.15 | 0.13 |

| | | Comparative Example 1 | Comparative Example 2 | Example 10 | Comparative Example 3 |
|---|---|---|---|---|---|
| Membrane | Type | PSf-4 | PSf-5 | PSf-6 | PSf-6 |
| | Molecular weight cut-off | 600,000 | 1,000,000 | 300,000 | 300,000 |
| Hydrophilic agent | Type | PVP | PVP | PVP | PVP |
| Membrane structure | Inner diameter (μm) | 155 | 157 | 498 | 498 |
| | Thickness (μm) | 33 | 36 | 87 | 87 |
| Immunoglobulin | Type | b-IgG | b-IgG | b-IgG | b-IgG |
| | Concentration (g/L) | 91 | 10 | 10 | 10 |
| | Monomer content (%) | 91 | 91 | 91 | 91 |
| | Dimer content (%) | 8 | 8 | 8 | 8 |
| Aggregation inhibitor | Lysine hydrochloride (g/L) | 0 | 0 | 0 | 0 |
| | Arginine hydrochloride (g/L) | 0 | 0 | 0 | 0 |
| Filtration method | | CF | CF | CF | DE |
| Linear velocity (cm/sec) | | 10 | 10 | 100 | — |
| Pressure (MPa) | | 0.027 | 0.027 | 0.1 | 0.1 |
| Throughput (g/m²) | | 239 | 423 | 1065 | 515 |
| Monomer permeation amount (g/m²) | | 201 | 363 | 875 | 413 |
| Dimer permeation amount (g/m²) | | 10.4 | 30.9 | 12.4 | 28.8 |
| Monomer permeability (%) | | 92.5 | 94.2 | 90.3 | 88.2 |

TABLE 1-continued

| | | | | |
|---|---|---|---|---|
| Dimer permeability (%) | 54.2 | 91.2 | 14.6 | 69.8 |
| Permeability ratio (dimer/monomer) | 0.59 | 0.97 | 0.16 | 0.79 |

PVP: polyvinylpyrrolidone, CF: cross-flow, DE: dead-end
b-IgG: Bovine immunoglobulin (bovine serum γ-globulin manufactured by Invitrogen)
h-IgG: human immunoglobulin (Glovenin-I-Nichiyaku manufactured by Nihon Pharmaceutical Co., Ltd.), SCF: anti-SCF antibody(monoclonal)

Example 11

The hollow fiber membranes (PPE-1) were bundled so that the total hollow cross-sectional area was 0.01 m$^2$ to obtain a fiber bundle for evaluating the human immunoglobulin monomer/dimer fractionation performance. The fiber bundle was connected to the cross-flow filtration apparatus shown in FIG. 3. The supply pump 2 (3) was rotated while adjusting the control valve 1 (7) so that the linear velocity inside the hollow fiber membrane was 10 cm/sec and the average value of the inlet pressure and the outlet pressure was 0.027 MPa. Since the concentration of the fractionation performance evaluation solution increases as cross-flow filtration proceeds, a PBS aqueous solution contained in the diluent tank (1) was added to the immunoglobulin stock solution tank (4) so that the concentration of the human immunoglobulin was constant (10 g/L). The immunoglobulin solution was subjected to cross-flow filtration at 25° C. for five hours. The content of the human immunoglobulin in the immunoglobulin stock solution and the immunoglobulin permeation solution was measured by an absorption spectrometer, and the content of the human immunoglobulin monomer and the human immunoglobulin dimer was measured by GPC. As shown in Table 2, the monomer permeation amount was 164 g/m$^2$, and the dimer permeation amount was 2.2 g/m$^2$. The human immunoglobulin monomer permeability and the human immunoglobulin dimer permeability were respectively 88.6% and 13.3%, and the permeability ratio (fractionation performance) was 0.15.

Example 12

The hollow fiber membranes (PPE-1) were bundled so that the total hollow cross-sectional area was 0.02 m$^2$ to obtain a fiber bundle for evaluating the human immunoglobulin monomer/dimer fractionation performance. A human immunoglobulin solution containing a human immunoglobulin (10 g/L) and lysine hydrochloride (50 g/L) was prepared. The fiber bundle and 100 ml of the human immunoglobulin solution were connected to the cross-flow filtration apparatus shown in FIG. 3. The supply pump 2 (3) was rotated while adjusting the control valve 1 (7) so that the linear velocity inside the hollow fiber membrane was 10 cm/sec and the outlet pressure was 0.010 MPa. Since the concentration of the human immunoglobulin solution increases as cross-flow filtration proceeds, a PBS aqueous solution containing lysine hydrochloride (50 g/L) contained in the diluent tank (1) was added to the immunoglobulin stock solution tank (4) so that the concentration of the human immunoglobulin was constant (10 g/L). The immunoglobulin solution was subjected to cross-flow filtration at 25° C. until the entire solution was filtered. The content of the human immunoglobulin monomer and the human immunoglobulin dimer in the immunoglobulin permeation solution was measured by GPC. As shown in Table 2, the monomer permeation amount was 42.5 g/m$^2$, and the dimer permeation amount was 0.60 g/m$^2$. The human immunoglobulin monomer permeability and the human immunoglobulin dimer permeability were respectively 93.4% and 15.0%, and the permeability ratio (fractionation performance) was 0.16.

Example 13

The permeation amount, permeability, and permeability ratio were calculated in the same manner as in Example 11, except for using an anti-SCF antibody (monoclonal) instead of the human immunoglobulin. As shown in Table 2, the anti-SCF antibody monomer permeation amount was 243 g/m$^2$, and the anti-SCF antibody dimer permeation amount was 1.4 g/m$^2$. The anti-SCF antibody monomer permeability and the anti-SCF antibody dimer permeability were respectively 90.8% and 12.5%, and the permeability ratio (fractionation performance) was 0.14.

Comparative Example 4

The permeation amount, permeability, and permeability ratio were calculated in the same manner as in Example 11, except for using the hollow fiber membrane (PPE-2) instead of the hollow fiber membrane (PPE-1). As shown in Table 2, the monomer permeation amount was 571 g/m$^2$, and the dimer permeation amount was 49.0 g/m$^2$. The human immunoglobulin monomer permeability and the human immunoglobulin dimer permeability were respectively 98.6% and 96.3%, and the permeability ratio (fractionation performance) was 0.98.

Comparative Example 5

The permeation amount, permeability, and permeability ratio were calculated in the same manner as in Example 11, except for using the hollow fiber membrane (PPE-3) instead of the hollow fiber membrane (PPE-1). As shown in Table 2, the monomer permeation amount was 3.0 g/m$^2$, and the dimer permeation amount was 0.12 g/m$^2$. The human immunoglobulin monomer permeability and the human immunoglobulin dimer permeability were respectively 21.3% and 9.5%, and the permeability ratio (fractionation performance) was 0.45.

Example 14

The hollow fiber membranes (PPE-4) were bundled so that the total hollow cross-sectional area was 0.01 m$^2$ to obtain a fiber bundle for evaluating the human immunoglobulin monomer/dimer fractionation performance. The fiber bundle was connected to the cross-flow filtration apparatus shown in FIG. 3. A supply pump 2 (3) was rotated while adjusting a control valve 1 (7) so that the linear velocity inside the hollow fiber membrane was 100 cm/sec and the average value of the inlet pressure and the outlet pressure was 0.1 MPa. Since the concentration of the fractionation performance evaluation solution increases as cross-flow filtration proceeds, a PBS aqueous solution contained in the diluent tank (1) was added to the immunoglobulin stock solution tank (4) by rotating the supply pump 1 (2) so that the concentration of the human immunoglobulin was constant (10 g/L). The immunoglobulin solution was subjected to cross-flow filtration at 25° C. for five hours. The content of the human immunoglobulin in the immunoglobulin stock solution and the immunoglobulin permeation solution was measured by an absorption spectrometer, and the content of the human immunoglobulin monomer and the human immunoglobulin dimer was measured by GPC. As shown in Table 2, the monomer permeation amount was 1,163 g/m$^2$, and the dimer permeation amount was 14.9 g/m$^2$. The human immunoglobulin monomer permeability and the human immunoglobulin dimer permeability were respectively 90.8% and 13.2%, and the permeability ratio (fractionation performance) was 0.15.

Comparative Example 6

An immunoglobulin solution was filtered using a fiber bundle prepared in the same manner as in Example 14 and the dead-end filtration apparatus shown in FIG. 5. A pressure regulator (31) was operated in a state in which a valve 1 (34) was opened and a valve 2 (35) was closed. The immunoglobulin solution was subjected to dead-end filtration while setting the inlet pressure to 0.1 MPa. In this case, high permeability was achieved in the initial stage of filtration. However, permeability gradually decreased so that an immunoglobulin permeation solution was not obtained. Specifically, a continuous dead-end filtration operation could not be performed steadily. The monomer permeation amount was 326 g/m$^2$, and the dimer permeation amount was 16.4 g/m$^2$ (i.e., the permeation amount significantly decreased). As shown in Table 2, the human immunoglobulin monomer permeability and the human immunoglobulin dimer permeability were respectively 92.8% and 53.2%, and the permeability ratio (fractionation performance) was 0.57 (i.e., the fractionation performance deteriorated).

Figure 3:
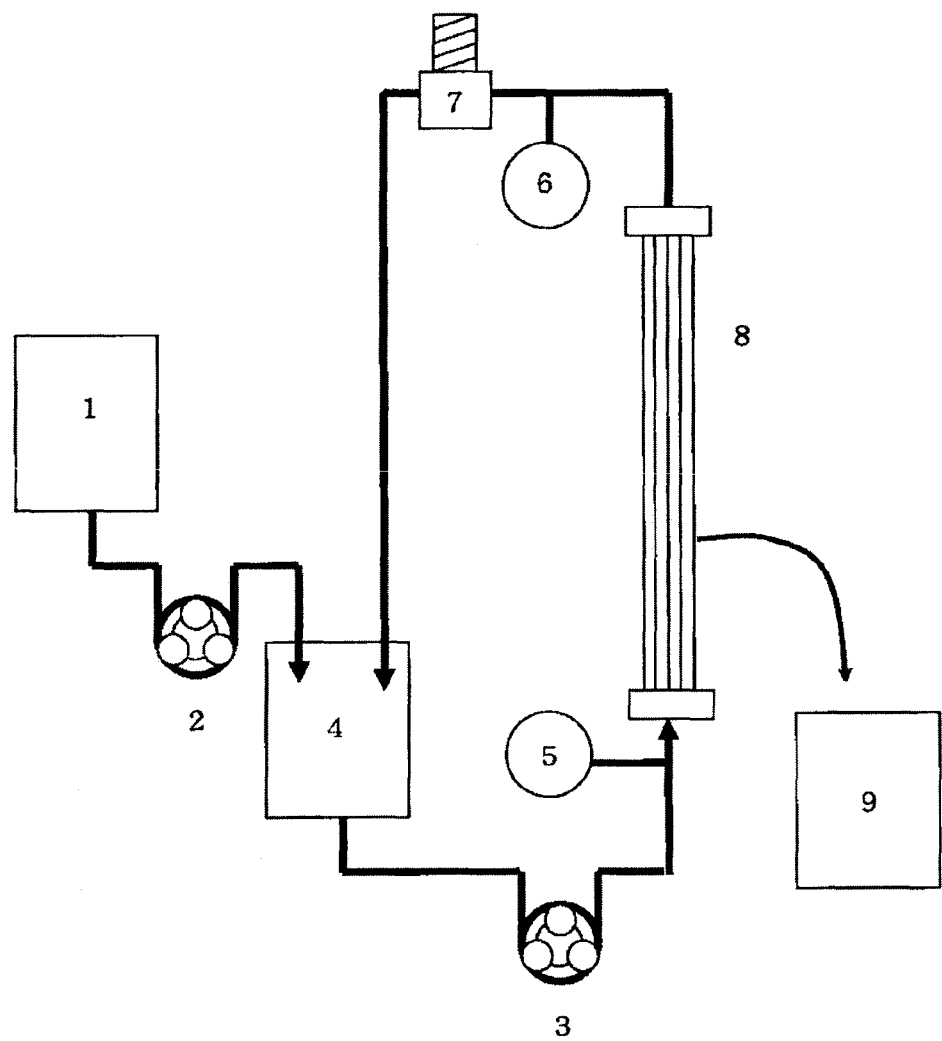
FIG. 3 is a view showing an example of cross-flow filtration method according to the present invention.

FIG. 3. The supply pump 2 (3) was rotated while adjusting the control valve 1 (7) so that the linear velocity inside the hollow fiber membrane was 10 cm/sec and the average value of the inlet pressure and the outlet pressure was 0.027 MPa. Since the concentration of the fractionation performance evaluation solution increases as cross-flow filtration proceeds, a PBS aqueous solution contained in the diluent tank (1) was added to the immunoglobulin stock solution tank (4) so that the concentration of the human immunoglobulin was constant (10 g/L). The immunoglobulin solution was subjected to cross-flow filtration at 25° C. for five hours. The content of the human immunoglobulin in the immunoglobulin stock solution and the immunoglobulin permeation solution was measured by an absorption spectrometer, and the content of the human immunoglobulin monomer and the human immunoglobulin dimer was measured by GPC. As shown in Table 3, the monomer permeation amount was 153 g/m$^2$, and the dimer permeation amount was 1.8 g/m$^2$. The human immunoglobulin monomer permeability and the human immunoglobulin dimer permeability were respectively 85.0% and 11.2%, and the permeability ratio (fractionation performance) was 0.13.

Example 16

The permeation amount, permeability, and permeability ratio were calculated in the same manner as in Example 15, except for using an anti-SCF antibody (monoclonal) instead of the immunoglobulin ("Glovenin-I-Nichiyaku" manufactured by Nihon Pharmaceutical Co., Ltd.). As shown in Table 3, the monomer permeation amount was 222 g/m$^2$, and the dimer permeation amount was 1.34 g/m$^2$. The anti-SCF antibody monomer permeability and the anti-SCF antibody

TABLE 2

| | | Example 11 | Example 12 | Example 13 | Comparative Example 4 | Comparative Example 5 | Example 14 | Comparative Example 6 |
|---|---|---|---|---|---|---|---|---|
| Membrane | Type | PPE-1 | PPE-1 | PPE-1 | PPE-2 | PPE-3 | PPE-4 | PPE-4 |
| | Molecular weight cut-off | 380,000 | 380,000 | 380,000 | 890,000 | — | 410,000 | 410,000 |
| Hydrophilic agent | Type | PS-PEG | PS-PEG | PS-PEG | PS-PEG | — | PS-PEG | PS-PEG |
| Membrane structure | Inner diameter (μm) | 173 | 173 | 173 | 161 | 169 | 568 | 568 |
| | Thickness (μm) | 30 | 30 | 30 | 35 | 39 | 123 | 123 |
| Immunoglobulin | Type | h-IgG | h-IgG | SCF | h-IgG | h-IgG | h-IgG | h-IgG |
| | Concentration (g/L) | 10 | 10 | 10 | 10 | 10 | 10 | 10 |
| | Monomer content (%) | 91 | 91 | 96 | 91 | 91 | 91 | 91 |
| | Dimer content (%) | 8 | 8 | 4 | 8 | 8 | 8 | 8 |
| Aggregation inhibitor | Lysine hydrochloride (g/L) | 0 | 50 | 0 | 0 | 0 | 0 | 0 |
| Filtration method | | CF | CF | CF | CF | CF | CF | DE |
| Linear velocity (cm/sec) | | 10 | 10 | 10 | 10 | 10 | 100 | — |
| Pressure (MPa) | | 0.027 | 0.01 | 0.027 | 0.027 | 0.027 | 0.1 | 0.1 |
| Throughput (g/m$^2$) | | 203 | 50.0 | 279 | 636 | 15.3 | 1408 | 386 |
| Monomer permeation amount (g/m$^2$) | | 164 | 42.5 | 243 | 571 | 3.0 | 1163 | 326 |
| Dimer permeation amount (g/m$^2$) | | 22 | 0.60 | 1.4 | 49.0 | 0.12 | 14.9 | 16.4 |
| Monomer permeability (%) | | 88.6 | 93.4 | 90.8 | 98.6 | 21.3 | 90.8 | 92.8 |
| Dimer permeability (%) | | 13.3 | 15.0 | 12.5 | 96.3 | 9.5 | 13.2 | 53.2 |
| Permeability ratio (dimer/monomer) | | 0.15 | 0.16 | 0.14 | 0.98 | 0.45 | 0.15 | 0.57 |

PS-PEG: polystyrene-polyethylene glycol block copolymer, CF: cross-flow, DE: dead-end
h-IgG: human immunoglobulin (Glovenin-I-Nichiyaku manufactured by Nihon Pharmaceutical Co., Ltd.)
SCF: anti-SCF antibody(monoclonal)

Example 15

The hollow fiber membranes (PMA) were bundled so that the total hollow cross-sectional area was 0.01 m$^2$ to obtain a fiber bundle for evaluating the human immunoglobulin monomer/dimer fractionation performance. The fiber bundle was connected to the cross-flow filtration apparatus shown in dimer permeability were respectively 91.2% and 13.2%, and the permeability ratio (fractionation performance) was 0.14.

Example 17

The hollow fiber membranes (PAN) were bundled so that the total hollow cross-sectional area was 0.01 m$^2$ to obtain a fiber bundle for evaluating the human immunoglobulin monomer/dimer fractionation performance. The fiber bundle was connected to the cross-flow filtration apparatus shown in FIG. 3. The supply pump 2 (3) was rotated while adjusting the control valve 1 (7) so that the linear velocity inside the hollow fiber membrane was 10 cm/sec and the average value of the inlet pressure and the outlet pressure was 0.027 MPa. Since the concentration of the fractionation performance evaluation solution increases as cross-flow filtration proceeds, a PBS aqueous solution contained in the diluent tank (1) was added to the immunoglobulin stock solution tank (4) so that the concentration of the human immunoglobulin was constant (10 g/L). The immunoglobulin solution was subjected to cross-flow filtration at 25° C. for five hours. The content of the human immunoglobulin in the immunoglobulin stock solution and the immunoglobulin permeation solution was measured by an absorption spectrometer, and the content of the human immunoglobulin monomer and the human immunoglobulin dimer was measured by GPC. As shown in Table 3, the monomer permeation amount was 169 g/m$^2$, and the dimer permeation amount was 2.1 g/m$^2$. The human immunoglobulin monomer permeability and the human immunoglobulin dimer permeability were respectively 88.8% and 12.3%, and the permeability ratio (fractionation performance) was 0.14.

Example 18

The permeation amount, permeability, and permeability ratio were calculated in the same manner as in Example 17, except for using an anti-SCF antibody (monoclonal) instead of the immunoglobulin ("Glovenin-I-Nichiyaku" manufactured by Nihon Pharmaceutical Co., Ltd.). As shown in Table 3, the monomer permeation amount was 228 g/m$^2$, and the dimer permeation amount was 1.3 g/m$^2$. The anti-SCF antibody monomer permeability and the anti-SCF antibody dimer permeability were respectively 92.1% and 12.8%, and the permeability ratio (fractionation performance) was 0.14.

fiber bundle for evaluating the human immunoglobulin monomer/dimer fractionation performance. The fiber bundle was connected to the cross-flow filtration apparatus shown in FIG. 3. The supply pump 2 (3) was rotated while adjusting the control valve 1 (7) so that the linear velocity inside the hollow fiber membrane was 10 cm/sec and the average value of the inlet pressure and the outlet pressure was 0.027 MPa. Since the concentration of the fractionation performance evaluation solution increases as cross-flow filtration proceeds, a PBS aqueous solution contained in the diluent tank (1) was added to the immunoglobulin stock solution tank (4) so that the concentration of the human immunoglobulin was constant (10 g/L). The immunoglobulin solution was subjected to cross-flow filtration at 25° C. for five hours. The content of the human immunoglobulin in the immunoglobulin stock solution and the immunoglobulin permeation solution was measured by an absorption spectrometer, and the content of the human immunoglobulin monomer and the human immunoglobulin dimer was measured by GPC. As shown in Table 4, the monomer permeation amount was 174 g/m$^2$, and the dimer permeation amount was 2.3 g/m$^2$. The human immunoglobulin monomer permeability and the human immunoglobulin dimer permeability were respectively 90.2% and 13.5%, and the permeability ratio (fractionation performance) was 0.15.

Example 20

The permeation amount, permeability, and permeability ratio were calculated in the same manner as in Example 19, except for using an anti-SCF antibody (monoclonal) instead of the immunoglobulin ("Glovenin-I-Nichiyaku" manufactured by Nihon Pharmaceutical Co., Ltd.). As shown in Table 4, the monomer permeation amount was 220 g/m$^2$, and the dimer permeation amount was 1.5 g/m$^2$. The anti-SCF antibody monomer permeability and the anti-SCF antibody dimer permeability were respectively 92.3% and 15.2%, and the permeability ratio (fractionation performance) was 0.16.

TABLE 3

| | | Example 15 | Example 16 | Example 17 | Example 18 |
|---|---|---|---|---|---|
| Membrane | Type | PMA | PMA | PAN | PAN |
| | Molecular weight cut-off | 350,000 | 350,000 | 360,000 | 360,000 |
| Hydrophilic agent | Type | PVP | PVP | PVP | PVP |
| Membrane structure | Inner diameter (μm) | 160 | 160 | 169 | 169 |
| | Thickness (μm) | 35 | 35 | 35 | 35 |
| Immunoglobulin | Type | h-IgG | SCF | h-IgG | SCF |
| | Concentration (g/L) | 10 | 10 | 10 | 10 |
| | Monomer content (%) | 91 | 96 | 91 | 96 |
| | Dimer content (%) | 8 | 4 | 8 | 4 |
| Filtration method | | CF | CF | CF | CF |
| Linear velocity (cm/sec) | | 10 | 10 | 10 | 10 |
| Pressure (MPa) | | 0.027 | 0.027 | 0.027 | 0.027 |
| Throughput (g/m$^2$) | | 198 | 253 | 209 | 258 |
| Monomer permeation amount (g/m$^2$) | | 153 | 222 | 169 | 228 |
| Dimer permeation amount (g/m$^2$) | | 1.8 | 1.34 | 2.1 | 1.3 |
| Monomer permeability (%) | | 85.0 | 91.2 | 88.8 | 92.1 |
| Dimer permeability (%) | | 11.2 | 13.2 | 12.3 | 12.8 |
| Permeability ratio (dimer/monomer) | | 0.13 | 0.14 | 0.14 | 0.14 |

PVP: polyvinylpyrrolidone
h-IgG: human immunoglobulin (Glovenin-I-Nichiyaku manufactured by Nihon Pharmaceutical Co., Ltd.)
SCF: anti-SCF antibody(monoclonal)
CF: cross-flow

Example 19

The hollow fiber membranes (PVDF) were bundled so that the total hollow cross-sectional area was 0.01 m$^2$ to obtain a

Example 21

The hollow fiber membranes (PE) were bundled so that the total hollow cross-sectional area was 0.01 m$^2$ to obtain a fiber bundle for evaluating the human immunoglobulin monomer/dimer fractionation performance. The fiber bundle was connected to the cross-flow filtration apparatus shown in FIG. 3. The supply pump 2 (3) was rotated while adjusting the control valve 1 (7) so that the linear velocity inside the hollow fiber membrane was 10 cm/sec and the average value of the inlet pressure and the outlet pressure was 0.027 MPa. Since the concentration of the fractionation performance evaluation solution increases as cross-flow filtration proceeds, a PBS aqueous solution contained in the diluent tank (1) was added to the immunoglobulin stock solution tank (4) so that the concentration of the human immunoglobulin was constant (10 g/L). The immunoglobulin solution was subjected to cross-flow filtration at 25° C. for five hours. The content of the human immunoglobulin in the immunoglobulin stock solution and the immunoglobulin permeation solution was measured by an absorption spectrometer, and the content of the human immunoglobulin monomer and the human immunoglobulin dimer was measured by GPC. As shown in Table 4, the monomer permeation amount was 161 g/m$^2$, and the dimer permeation amount was 2.1 g/m$^2$. The human immunoglobulin monomer permeability and the human immunoglobulin dimer permeability were respectively 89.3% and 13.5%, and the permeability ratio (fractionation performance) was 0.15.

Example 22

The permeation amount, permeability, and permeability ratio were calculated in the same manner as in Example 21, except for using an anti-SCF antibody (monoclonal) instead of the immunoglobulin ("Glovenin-I-Nichiyaku" manufactured by Nihon Pharmaceutical Co., Ltd.). As shown in Table 4, the monomer permeation amount was 203 g/m$^2$, and the dimer permeation amount was 1.2 g/m$^2$. The anti-SCF antibody monomer permeability and the anti-SCF antibody dimer permeability were respectively 89.9% and 12.5%, and the permeability ratio (fractionation performance) was 0.14.

fiber bundle for evaluating the human immunoglobulin monomer/dimer fractionation performance. The fiber bundle was connected to the cross-flow filtration apparatus shown in FIG. 3. The supply pump 2 (3) was rotated while adjusting the control valve 1 (7) so that the linear velocity inside the hollow fiber membrane was 10 cm/sec and the average value of the inlet pressure and the outlet pressure was 0.027 MPa. Since the concentration of the fractionation performance evaluation solution increases as cross-flow filtration proceeds, a PBS aqueous solution contained in the diluent tank (1) was added to the immunoglobulin stock solution tank (4) so that the concentration of the human immunoglobulin was constant (10 g/L). The immunoglobulin solution was subjected to cross-flow filtration at 25° C. for five hours. The content of the human immunoglobulin in the immunoglobulin stock solution and the immunoglobulin permeation solution was measured by an absorption spectrometer, and the content of the human immunoglobulin monomer and the human immunoglobulin dimer was measured by GPC. As shown in Table 5, the monomer permeation amount was 177 g/m$^2$, and the dimer permeation amount was 2.6 g/m$^2$. The human immunoglobulin monomer permeability and the human immunoglobulin dimer permeability were respectively 90.6% and 15.2%, and the permeability ratio (fractionation performance) was 0.17.

Example 24

The permeation amount, permeability, and permeability ratio were calculated in the same manner as in Example 23, except for using an anti-SCF antibody (monoclonal) instead of the immunoglobulin ("Glovenin-I-Nichiyaku" manufactured by Nihon Pharmaceutical Co., Ltd.). As shown in Table 5, the monomer permeation amount was 211 g/m$^2$, and the dimer permeation amount was 2.5 g/m$^2$. The anti-SCF antibody monomer permeability and the anti-SCF antibody dimer permeability were respectively 91.5% and 12.3%, and the permeability ratio (fractionation performance) was 0.13.

TABLE 4

|  |  | Example 19 | Example 20 | Example 21 | Example 22 |
|---|---|---|---|---|---|
| Membrane | Type | PVDF | PVDF | PE | PE |
|  | Molecular weight cut-off | 350,000 | 350,000 | 290,000 | 290,000 |
| Hydrophilic agent | Type | HPA | HPA | HPA | HPA |
| Membrane structure | Inner diameter (μm) | 159 | 159 | 176 | 176 |
|  | Thickness (μm) | 35 | 35 | 36 | 36 |
| Immunoglobulin | Type | h-IgG | SCF | h-IgG | SCF |
|  | Concentration (g/L) | 10 | 10 | 10 | 10 |
|  | Monomer content (%) | 91 | 96 | 91 | 96 |
|  | Dimer content (%) | 8 | 4 | 8 | 4 |
| Filtration method |  | CF | CF | CF | CF |
| Linear velocity (cm/sec) |  | 10 | 10 | 10 | 10 |
| Pressure (MPa) |  | 0.027 | 0.027 | 0.027 | 0.027 |
| Throughput (g/m$^2$) |  | 212 | 248 | 198 | 235 |
| Monomer permeation amount (g/m$^2$) |  | 174 | 220 | 161 | 203 |
| Dimer permeation amount (g/m$^2$) |  | 2.3 | 1.5 | 2.1 | 1.2 |
| Monomer permeability (%) |  | 90.2 | 92.3 | 89.3 | 89.9 |
| Dimer permeability (%) |  | 13.5 | 15.2 | 13.5 | 12.5 |
| Permeability ratio (dimer/monomer) |  | 0.15 | 0.16 | 0.15 | 0.14 |

HPA: hydroxypropyl acrylate
h-IgG: human immunoglobulin (Glovenin-I-Nichiyaku manufactured by Nihon Pharmaceutical Co, Ltd.)
SCF: anti-SCF antibody(monoclonal)
CF: cross-flow Example 23

The hollow fiber membranes (PVA) were bundled so that the total hollow cross-sectional area was 0.01 m$^2$ to obtain a Example 25

The hollow fiber membranes (CEL) were bundled so that the total hollow cross-sectional area was 0.01 m$^2$ to obtain a fiber bundle for evaluating the human immunoglobulin monomer/dimer fractionation performance. The fiber bundle was connected to the cross-flow filtration apparatus shown in FIG. 3. The supply pump 2 (3) was rotated while adjusting the control valve 1 (7) so that the linear velocity inside the hollow fiber membrane was 10 cm/sec and the average value of the inlet pressure and the outlet pressure was 0.027 MPa. Since the concentration of the fractionation performance evaluation solution increases as cross-flow filtration proceeds, a PBS aqueous solution contained in the diluent tank (1) was added to the immunoglobulin stock solution tank (4) so that the concentration of the human immunoglobulin was constant (10 g/L). The immunoglobulin solution was subjected to cross-flow filtration at 25° C. for five hours. The content of the human immunoglobulin in the immunoglobulin stock solution and the immunoglobulin permeation solution was measured by an absorption spectrometer, and the content of the human immunoglobulin monomer and the human immunoglobulin dimer was measured by GPC. As shown in Table 5, the monomer permeation amount was 193 g/m$^2$, and the dimer permeation amount was 3.1 g/m$^2$. The human immunoglobulin monomer permeability and the human immunoglobulin dimer permeability were respectively 89.9% and 16.2%, and the permeability ratio (fractionation performance) was 0.18.

Example 26

The permeation amount, permeability, and permeability ratio were calculated in the same manner as in Example 25, except for using an anti-SCF antibody (monoclonal) instead of the immunoglobulin ("Glovenin-I-Nichiyaku" manufactured by Nihon Pharmaceutical Co., Ltd.). As shown in Table 5, the monomer permeation amount was 223 g/m$^2$, and the dimer permeation amount was 1.7 g/m$^2$. The anti-SCF antibody monomer permeability and the anti-SCF antibody dimer permeability were respectively 91.2% and 16.9%, and the permeability ratio (fractionation performance) was 0.19.

effect, the bovine immunoglobulin permeability and the fractionation performance in the filtration experiments were evaluated.

The aggregation inhibiting effect was evaluated according to the section entitled "Evaluation of aggregation inhibiting effect". As shown in Table 6, the aggregation inhibiting effect was as high as 90.

The permeability and the permeability ratio were calculated in the same manner as in Example 4 using a bovine immunoglobulin solution containing L(+)-lysine (50 g/L). As shown in Table 6, the monomer permeation amount was 155 g/m$^2$, and the dimer permeation amount was 2.0 g/m$^2$. The bovine immunoglobulin monomer permeability and the bovine immunoglobulin dimer permeability were respectively 97.3% and 14.3%, and the permeability ratio (fractionation performance) was 0.15. This suggests that the bovine immunoglobulin dimer was separated by the membrane, and the bovine immunoglobulin monomer was collected with high permeability.

Example 28

The bovine immunoglobulin aggregation inhibiting effect, the bovine immunoglobulin permeability and the fractionation performance in the filtration experiments were evaluated in the same manner as in Example 27, except that L(+)-lysine hydrochloride ("Lysine" manufactured by Wako Pure Chemical Industries, Ltd.) was used as the aggregation inhibitor. As shown in Table 6, the aggregation inhibiting effect was as high as 88. The monomer permeation amount was 152 g/m$^2$, and the dimer permeation amount was 1.9 g/m$^2$. The bovine immunoglobulin monomer permeability and the bovine immunoglobulin dimer permeability were respectively 96.6% and 13.7%, and the permeability ratio (fractionation performance) was 0.14. This suggests that the bovine immunoglobulin dimer was separated by the membrane, and the bovine immunoglobulin monomer was collected with high permeability.

TABLE 5

|  |  | Example 23 | Example 24 | Example 25 | Example 26 |
|---|---|---|---|---|---|
| Membrane | Type | PVA | PVA | CEL | CEL |
|  | Molecular weight cut-off | 380,000 | 380,000 | 390,000 | 390,000 |
| Membrane | Inner diameter (μm) | 158 | 158 | 181 | 181 |
| structure | Thickness (μm) | 41 | 41 | 33 | 33 |
| Immunoglobulin | Type | h-IgG | SCF | h-IgG | SCF |
|  | Concentration (g/L) | 10 | 10 | 10 | 10 |
|  | Monomer content (%) | 91 | 96 | 91 | 96 |
|  | Dimer content (%) | 8 | 4 | 8 | 4 |
| Filtration method |  | CF | CF | CF | CF |
| Linear velocity (cm/sec) |  | 10 | 10 | 10 | 10 |
| Pressure (MPa) |  | 0.027 | 0.027 | 0.027 | 0.027 |
| Throughput (g/m$^2$) |  | 215 | 253 | 236 | 255 |
| Monomer permeation amount (g/m$^2$) |  | 177 | 211 | 193 | 223 |
| Dimer permeation amount (g/m$^2$) |  | 2.6 | 2.5 | 3.1 | 1.7 |
| Monomer permeability (%) |  | 90.6 | 91.5 | 89.9 | 91.2 |
| Dimer permeability (%) |  | 15,2 | 12.3 | 16.2 | 16.9 |
| Permeability ratio (dimer/monomer) |  | 0.17 | 0.13 | 0.18 | 0.19 | h-IgG: human immunoglobulin (Glovenin-I-Nichiyaku manufactured by Nihon Pharmaceutical Co., Ltd.)
SCF: anti-SCF antibody(monoclonal)
CF: cross-flow Example 27

L(+)-lysine ("Lysine" manufactured by Wako Pure Chemical Industries, Ltd.) was added to a bovine immunoglobulin solution as an aggregation inhibitor to a concentration of 50 g/L, and the bovine immunoglobulin aggregation inhibiting Example 29

The bovine immunoglobulin aggregation inhibiting effect, the bovine immunoglobulin permeability and the fractionation performance in the filtration experiments were evaluated in the same manner as in Example 27, except that L(+)- arginine hydrochloride ("Arginine" manufactured by Wako Pure Chemical Industries, Ltd.) was used as the aggregation inhibitor.

As shown in Table 6, the aggregation inhibiting effect was as high as 72. The monomer permeation amount was 148 g/m$^2$, and the dimer permeation amount was 2.0 g/m$^2$. The bovine immunoglobulin monomer permeability and the bovine immunoglobulin dimer permeability were respectively 95.1% and 14.6%, and the permeability ratio (fractionation performance) was 0.15. This suggests that the bovine immunoglobulin dimer was separated by the membrane, and the bovine immunoglobulin monomer was collected with high permeability.

Example 30

The bovine immunoglobulin aggregation inhibiting effect, the bovine immunoglobulin permeability and the fractionation performance in the filtration experiments were evaluated in the same manner as in Example 27, except that polyethylene glycol 300 (manufactured by Wako Pure Chemical Industries, Ltd., molecular weight: 300) was added to a bovine immunoglobulin solution as the aggregation inhibitor to a concentration of 10 g/L.

As shown in Table 6, the aggregation inhibiting effect was as high as 80. The monomer permeation amount was 146 g/m$^2$, and the dimer permeation amount was 2.0 g/m$^2$. The bovine immunoglobulin monomer permeability and the bovine immuno globulin dimer permeability were respectively 96.1% and 15.0%, and the permeability ratio (fractionation performance) was 0.16. This suggests that the bovine immunoglobulin dimer was separated by the membrane, and the bovine immunoglobulin monomer was collected with high permeability.

Example 31

The bovine immunoglobulin aggregation inhibiting effect, the bovine immunoglobulin permeability and the fractionation performance in the filtration experiments were evaluated in the same manner as in Example 27, except that polyethylene glycol 1K (manufactured by Wako Pure Chemical Industries, Ltd., molecular weight: 1000) was added to a bovine immunoglobulin solution as the aggregation inhibitor to a concentration of 10 g/L.

As shown in Table 6, the aggregation inhibiting effect was as high as 80. The monomer permeation amount was 143 g/m$^2$, and the dimer permeation amount was 1.9 g/m$^2$. The bovine immunoglobulin monomer permeability and the bovine immunoglobulin dimer permeability were respectively 95.2% and 14.4%, and the permeability ratio (fractionation performance) was 0.15. This suggests that the bovine immunoglobulin dimer was separated by the membrane, and the bovine immunoglobulin monomer was collected with high permeability.

Example 32

The bovine immunoglobulin aggregation inhibiting effect, the bovine immunoglobulin permeability and the fractionation performance in the filtration experiments were evaluated in the same manner as in Example 27, except that polyethylene glycol 4K (manufactured by Wako Pure Chemical Industries, Ltd., molecular weight: 4000) was added to a bovine immunoglobulin solution as the aggregation inhibitor to a concentration of 10 g/L.

As shown in Table 6, the aggregation inhibiting effect was as high as 69. The monomer permeation amount was 139 g/m$^2$, and the dimer permeation amount was 1.8 g/m$^2$. The bovine immunoglobulin monomer permeability and the bovine immunoglobulin dimer permeability were respectively 93.7% and 13.8%, and the permeability ratio (fractionation performance) was 0.15. This suggests that the bovine immunoglobulin dimer was separated by the membrane, and the bovine immunoglobulin monomer was collected with high permeability.

TABLE 6

|  |  | Example 27 | Example 28 | Example 29 | Example 30 | Example 31 | Example 32 |
|---|---|---|---|---|---|---|---|
| Aggregation inhibitor | Type | Lysine | Lysine hydrochloride | Arginine hydrochloride | PEG 300 | PEG 1K | PEG 4K |
|  | Concentration (g/L) | 50 | 50 | 50 | 10 | 10 | 10 |
| Immunoglobulin | Type | b-IgG | b-IgG | b-IgG | b-IgG | b-IgG | b-IgG |
|  | Concentration (g/L) | 10 | 10 | 10 | 10 | 10 | 10 |
| Evaluation 1 | Aggregation inhibiting effect | 90 | 88 | 72 | 80 | 80 | 69 |
| Evaluation 2 | Throughput (g/m$^2$) | 175 | 173 | 171 | 167 | 165 | 163 |
|  | Monomer permeation amount (g/m$^2$) | 155 | 152 | 148 | 146 | 143 | 139 |
|  | Dimer permeation amount (g/m$^2$) | 2.0 | 1.9 | 2.0 | 2.0 | 1.9 | 1.8 |
|  | Monomer permeability (%) | 97.3 | 96.6 | 95.1 | 96.1 | 95.2 | 93.7 |
|  | Dimer permeability (%) | 14.3 | 13.7 | 14.6 | 15.0 | 14.4 | 13.8 |
|  | Permeability ratio (dimer/monomer) | 0.15 | 0.14 | 0.15 | 0.16 | 0.15 | 0.15 |

PEG: polyethylene glycol
b-IgG: bovine immunoglobulin (bovine serum γ-globulin manufactured by Invitrogen)

Example 33

Figure 10:
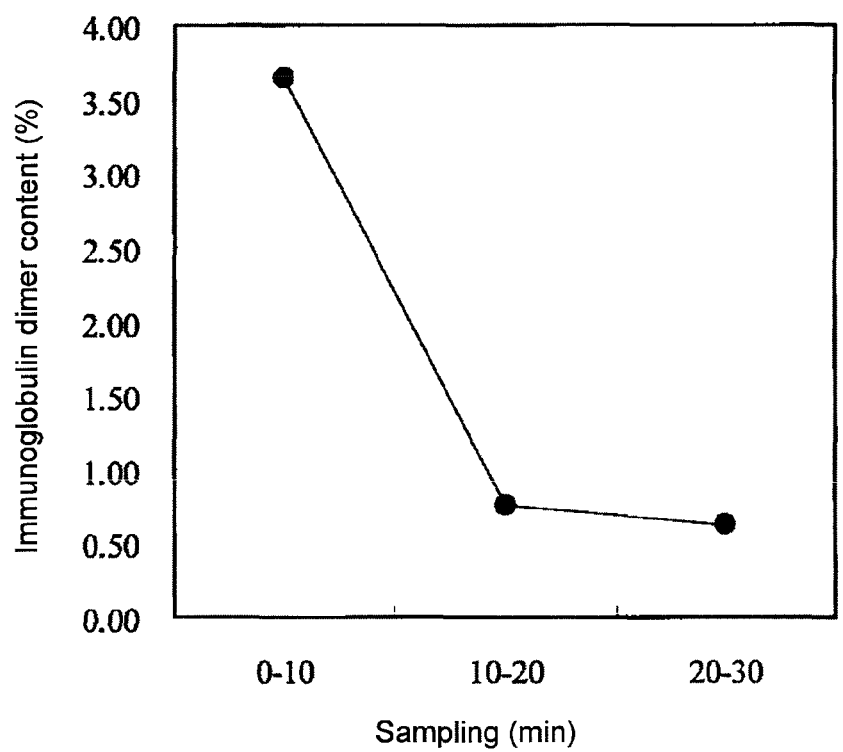
FIG. 10 is a view showing an example of the relationship between the sampling time and immunoglobulin dimer content.
Figure 11:
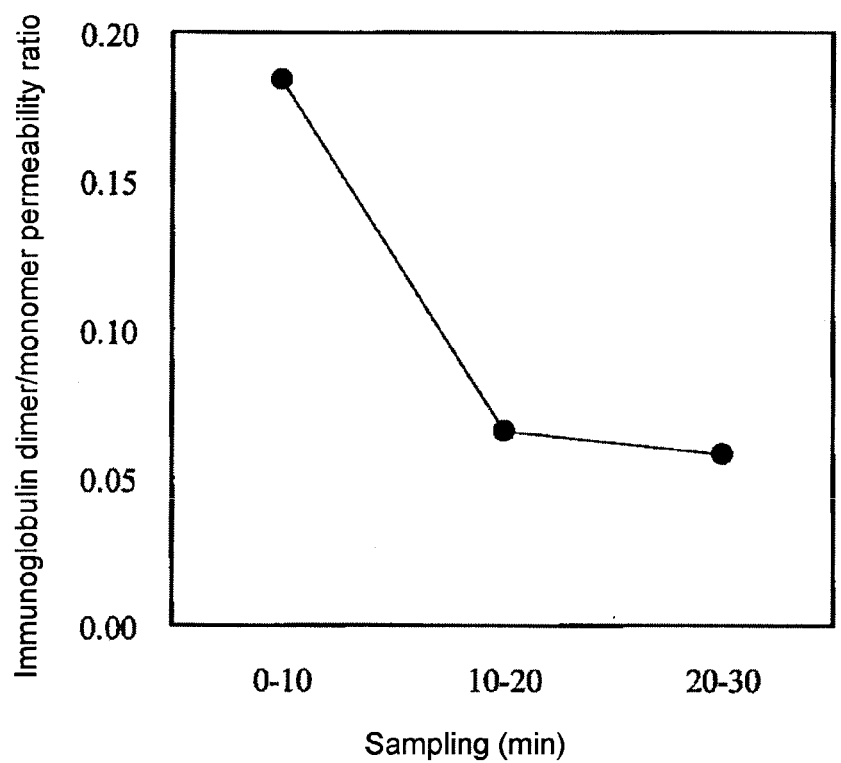
FIG. 11 is a view showing an example of the relationship between the sampling time and immunoglobulin dimer/monomer permeability ratio.

A bovine immunoglobulin solution was subjected to cross-flow filtration in the same manner as in Example 4 to analyze a temporal change in fractionation performance. A fraction was collected at intervals of 10 minutes. FIGS. 10 and 11 show the bovine immunoglobulin dimer content in the immunoglobulin permeation solution and the permeability ratio (fractionation performance), respectively. As shown in FIGS. 10 and 11, the fractionation performance and the bovine immunoglobulin dimer content in the immunoglobulin permeation solution differed between the initial period (0 to 10 minutes) and the subsequent period (after 10 minutes). Specifically, the fractionation performance was improved after 10 minutes, and the bovine immunoglobulin dimer content in the immunoglobulin permeation solution decreased to 1% or less. The ratio of immunoglobulin dimer permeability to immunoglobulin monomer permeability rapidly decreased after 10 minutes.

A cross-flow filtration experiment was performed in which the immunoglobulin permeation solution was recycled to the immunoglobulin stock solution tank (4) for 10 minutes after starting filtration. The filtration experiment was performed for 5 hours and 10 minutes (i.e., the sampling time was 5 hours). As shown in Table 7, the monomer permeation amount was 123 g/m², and the dimer permeation amount was 0.8 g/m². The bovine immunoglobulin monomer permeability and the bovine immunoglobulin dimer permeability were respectively 84.0% and 6.2%, and the permeability ratio (fractionation performance) was 0.07. The bovine immunoglobulin dimer content in the immunoglobulin permeation solution was 0.65%. In Example 4 in which the immunoglobulin permeation solution was not recycled, the bovine immunoglobulin dimer content in the immunoglobulin permeation solution was 1.42%. It was found that the degree of purification of the bovine immunoglobulin monomer is increased by recycling the immunoglobulin permeation solution.

Example 34

A human immunoglobulin solution was subjected to cross-flow filtration in the same manner as in Example 5 to monitor the human immunoglobulin dimer content in the immunoglobulin permeation solution at intervals of 10 minutes. After recycling the immunoglobulin permeation solution to the immunoglobulin stock solution tank (4) until the human immunoglobulin dimer content in the immunoglobulin permeation solution decreased to 1%, the human immunoglobulin monomer and the human immunoglobulin dimer in the immunoglobulin solution were separated by cross-flow filtration. As shown in Table 7, the monomer permeation amount was 42.3 g/m², and the dimer permeation amount was 0.21 g/m². The bovine immunoglobulin monomer permeability and the bovine immunoglobulin dimer permeability were respectively 93.0% and 5.3%, and the permeability ratio (fractionation performance) was 0.06. The human immunoglobulin dimer content in the immunoglobulin permeation solution was 0.49%. In Example 5 in which the immunoglobulin permeation solution was not recycled, the human immunoglobulin dimer content in the immunoglobulin permeation solution was 0.88%. It was found that the degree of purification of the human immunoglobulin monomer is increased by recycling the immunoglobulin permeation solution.

TABLE 7

| | | Example 33 | Example 34 |
|---|---|---|---|
| Membrane | Type | PSf-1 | PSf-2 |
| | Molecular weight cut-off | 300,000 | 360,000 |
| Hydrophilic agent | Type | PVP | PVP |
| Membrane structure | Inner diameter (μm) | 151 | 207 |
| | Thickness (μm) | 30 | 41 |
| Immunoglobulin | Type | b-IgG | h-IgG |
| | Concentration (g/L) | 10 | 10 |
| | Monomer content (%) | 91 | 91 |
| | Dimer content (%) | 8 | 8 |
| Aggregation inhibitor | Lysine hydrochloride (g/L) | 0 | 50 |
| Filtration method | | CF | CF |
| Linear velocity (cm/sec) | | 10 | 10 |
| Pressure (MPa) | | 0.027 | 0.010 |
| Throughput (g/m²) | | 161 | 50 |
| Monomer permeation amount (g/m²) | | 123 | 42.3 |
| Dimer permeation amount (g/m²) | | 0.80 | 0.21 |
| Dimer content (%) | | 0.65 | 0.49 |
| Monomer permeability (%) | | 84.0 | 93.0 |

TABLE 7-continued

| | Example 33 | Example 34 |
|---|---|---|
| Dimer permeability (%) | 6.2 | 5.3 |
| Permeability ratio (dimer/monomer) | 0.07 | 0.06 |

PVP: polyvinylpyrrolidone, CF: cross-flow
b-IgG: bovine immunoglobulin (bovine serum γ-globulin manufactured by Invitrogen)
h-IgG: human immunoglobulin (Glovenin-I-Nichiyaku manufactured by Nihon Pharmaceutical Co., Ltd.)

Reference Example 1

A filtration experiment was performed in the same manner as in Example 33, except that the immunoglobulin permeation solution was not recycled to the immunoglobulin stock solution, and the sample obtained within 10 minutes after starting filtration was disposed. The amount of the bovine immunoglobulin monomer disposed within 10 minutes after starting filtration was 6.3 g/m². Specifically, a significant loss occurred as compared with Example 33.

Reference Example 2

A filtration experiment was performed in the same manner as in Example 34, except that the immunoglobulin permeation solution was not recycled to the immunoglobulin stock solution, and the sample obtained within 10 minutes after starting filtration was disposed. The amount of the human immunoglobulin monomer disposed within 10 minutes after starting filtration was 3.5 g/m². Specifically, a significant loss occurred as compared with Example 34.

Example 35

The hollow fiber membranes (PSf-1) were bundled so that the total hollow cross-sectional area was 0.01 m² to obtain a fiber bundle for evaluating the human immunoglobulin monomer/dimer fractionation performance and the virus clearance ability. The fiber bundle was connected to the cross-flow filtration apparatus shown in FIG. 3.

A porcine parvovirus was used as an indicator virus. A solution containing a human immunoglobulin (10 g/L) and a porcine parvovirus ($10^{5.0}$ TCID$_{50}$/ml) was introduced into the immunoglobulin stock solution tank (4) of the cross-flow filtration apparatus shown in FIG. 3.

The supply pump 2 (3) was rotated while adjusting the control valve 1 (7) so that the linear velocity inside the hollow fiber membrane was 10 cm/sec and the average value of the inlet pressure and the outlet pressure was 0.027 MPa. Since the concentration of the fractionation performance evaluation solution increases as cross-flow filtration proceeds, a PBS aqueous solution contained in the diluent tank (1) was added to the immunoglobulin stock solution tank (4) so that the concentration of the human immunoglobulin was constant (10 g/L). The immunoglobulin solution was subjected to cross-flow filtration at 25° C. for five hours. The content of the human immunoglobulin monomer and the human immunoglobulin dimer was measured by GPC. The TCID$_{50}$ of the porcine parvovirus in the immunoglobulin permeation solution was measured, and the porcine parvovirus log reduction value (LRV) was calculated. As shown in Table 8, the monomer permeation amount was 115 g/m², and the dimer permeation amount was 1.5 g/m². The human immunoglobulin monomer permeability and the human immunoglobulin dimer permeability were respectively 86.8% and 12.8%, and the permeability ratio (fractionation performance) was 0.15. The virus log reduction value (LRV) was 4.3 or more.

Example 36

The hollow fiber membranes (PSf-2) were bundled so that the total hollow cross-sectional area was 0.02 m² to obtain a fiber bundle for evaluating the human immunoglobulin monomer/dimer fractionation performance and the virus clearance ability. The fiber bundle was connected to the cross-flow filtration apparatus shown in FIG. 3.

A porcine parvovirus was used as an indicator virus. 100 ml of a solution containing a human immunoglobulin (10 g/L), a porcine parvovirus ($10^{5.0}$ $TCID_{50}$/ml), and lysine hydrochloride (50 g/L) was introduced into the immunoglobulin stock solution tank (4) of the cross-flow filtration apparatus shown in FIG. 3.

The supply pump 2 (3) was rotated while adjusting the control valve 1 (7) so that the linear velocity inside the hollow fiber membrane was 10 cm/sec and the outlet pressure was 0.01 MPa. Since the concentration of the human immunoglobulin solution increases as cross-flow filtration proceeds, a PBS aqueous solution containing lysine hydrochloride (50 g/L) contained in the diluent tank (1) was added to the immunoglobulin stock solution tank (4) so that the concentration of the human immunoglobulin was constant (10 g/L). The immunoglobulin solution was subjected to cross-flow filtration at 25° C. until the entire solution was filtered. The content of the human immunoglobulin monomer and the human immunoglobulin dimer in the immunoglobulin permeation solution was measured by GPC. As shown in Table 8, the monomer permeation amount was 43.4 g/m², and the dimer permeation amount was 0.46 g/m². The human immunoglobulin monomer permeability and the human immunoglobulin dimer permeability were respectively 95.4% and 11.4%, and the permeability ratio (fractionation performance) was 0.12. The virus log reduction value (LRV) was 4.3 or more.

Comparative Example 7

The permeation amount, permeability, permeability ratio, and virus log reduction value were calculated in the same manner as in Example 35, except for using the hollow fiber membrane (PSf-5) instead of the hollow fiber membrane (PSf-1). As shown in Table 8, the monomer permeation amount was 337 g/m², and the dimer permeation amount was 29.2 g/m². The human immunoglobulin monomer permeability and the human immunoglobulin dimer permeability were respectively 95.3% and 93.9%, and the permeability ratio (fractionation performance) was 0.99. The virus log reduction value (LRV) was 2.3.

TABLE 8

|  |  | Example 35 | Example 36 | Comparative Example 7 |
|---|---|---|---|---|
| Membrane | Type | PSf-1 | PSf-2 | PSf-5 |
|  | Molecular weight cut-off | 300,000 | 360,000 | 1,000,000 |
| Hydrophilic agent | Type | PVP | PVP | PVP |
| Membrane structure | Inner diameter (μm) | 151 | 207 | 157 |
|  | Thickness (μm) | 30 | 41 | 36 |
| Immunoglobulin | Type | h-IgG | h-IgG | h-IgG |
|  | Concentration (g/L) | 10 | 10 | 10 |
|  | Monomer content (%) | 91 | 91 | 91 |
|  | Dimer content (%) | 8 | 8 | 8 |
| Aggregation inhibitor | Lysine hydrochloride (g/L) | 0 | 50 | 0 |
| Filtration method |  | CF | CF | CF |
| Linear velocity (cm/sec) |  | 10 | 10 | 10 |
| Pressure (MPa) |  | 0.027 | 0.01 | 0.027 |
| Throughput (g/m²) |  | 146 | 50 | 389 |
| Monomer permeation amount (g/m²) |  | 115 | 43.4 | 337 |
| Dimer permeation amount (g/m²) |  | 1.5 | 0.46 | 29.2 |
| Monomer permeability (%) |  | 86.8 | 95.4 | 95.3 |
| Dimer permeability (%) |  | 12.8 | 11.4 | 93.9 |
| Permeability ratio (dimer/monomer) |  | 0.15 | 0.12 | 0.99 |
| Virus reduction value (LRV) |  | >4.3 | >4.3 | 2.3 |

PVP: polyvinylpyrrolidone
h-IgG: human immunoglobulin (Glovenin-I-Nichiyaku manufactured by Nihon Pharmaceutical Co., Ltd.)
CF: cross-flow Example 37

A culture medium of an anti-SCF antibody expression clone produced according to the section entitled <Production of anti-SCF antibody> was made to flow through Protein A-Sepharose CL-4B (manufactured by Pharmacia) equilibrated using a buffer to effect antibody binding, and the column was washed with the buffer. A 0.2 M glycine-HCl buffer (pH: 3.0) was introduced into the column to elute the anti-SCF antibody. The purity of the anti-SCF antibody (including aggregates) was 99.5% or more, and the recovery rate was 96%. The content of the anti-SCF antibody monomer was 91.0%, and the content of the anti-SCF antibody aggregates (e.g., dimer) was 9%.

The anti-SCF antibody monomer was separated (purified) from the anti-SCF antibody aggregates (e.g., dimer) using a membrane under the same filtration conditions as in Example 4. As a result, the content of the anti-SCF antibody monomer was 98.6%, and the content of the anti-SCF antibody aggregates (e.g., dimer) was 1.4% (i.e., the content of the anti-SCF antibody aggregates decreased). The monomer permeability was 83.7%. The above results suggest that a high-purity anti-SCF antibody monomer can be obtained by performing separation/purification using a membrane after affinity chromatography purification.

Example 38

A culture medium of an anti-SCF antibody expression clone produced according to the section entitled <Production of anti-SCF antibody> was made to flow through Protein A-Sepharose CL-4B (manufactured by Pharmacia) equilibrated using a buffer to effect antibody binding, and the column was washed with the buffer. A 0.2 M glycine-HCl buffer (pH: 3.0) was introduced into the column to elute the anti-SCF antibody. The purity of the anti-SCF antibody (including aggregates) was 99.5% or more, and the recovery rate was 96%. The content of the anti-SCF antibody monomer was 91.0%, and the content of the anti-SCF antibody aggregate (e.g., dimer) was 9%.

The anti-SCF antibody monomer was separated (purified) from the anti-SCF antibody aggregates (e.g., dimer) using a membrane under the same filtration conditions as in Example 5. As a result, the content of the anti-SCF antibody monomer was 99.3%, and the content of the anti-SCF antibody aggregates (e.g., dimer) was 0.73% (i.e., the content of the anti-SCF antibody aggregates decreased). The monomer permeability was 95.6%. The above results suggest that a high-purity anti-SCF antibody monomer can be obtained by performing separation/purification using a membrane after affinity chromatography purification.

Example 39

A study was conducted on concentration after the separation step in Example 4. Immunoglobulin dimers fractionation performance in the immunoglobulin aggregate removal step was evaluated. The monomer permeation amount was 126 g/m$^2$, and the dimer permeation amount was 1.8 g/m$^2$. Immunoglobulin monomer permeability and immunoglobulin dimer permeability were respectively 83.7% and 13.7%, and the permeability ratio was 0.16. This suggests that immunoglobulin dimers was separated by the membrane, and immunoglobulin monomers was collected with high permeability.

The immunoglobulin concentration decreased to 0.9 g/L in the immunoglobulin aggregate removal step. However, the immunoglobulin concentration could be increased to 9.4 g/L (concentration rate: 10.4) by the immunoglobulin concentration step. A filtrate obtained by the immunoglobulin concentration step could be recycled as the diluent used in the immunoglobulin separation step. Since the immunoglobulin aggregate removal step and the immunoglobulin concentration step were continuously performed, the immunoglobulin concentration step was completed within about 0.5 hours after completion of the immunoglobulin aggregate removal step (5 hours).

The size of the diluent tank can be reduced while reducing the cost of the buffer and the additive by continuously and simultaneously performing the immunoglobulin aggregate removal step and the immunoglobulin concentration step, and recycling the permeation solution obtained by the concentration step as the diluent for the immunoglobulin stock solution. Moreover, the size of the permeation solution tank can also be reduced. It may be unnecessary to provide the permeation solution tank depending on the conditions. Moreover, the operation time can be significantly reduced so that an increase in productivity and a reduction in fixed cost (e.g., labor cost) can be achieved.

Reference Example 3

An experiment was performed in the same manner as in Example 39, except that the immunoglobulin separation step and the immunoglobulin concentration step were not performed continuously. In the immuno globulin aggregate removal step, the monomer permeation amount was 126 g/m$^2$, and the dimer permeation amount was 1.8 g/m$^2$.

Immunoglobulin monomer permeability and immunoglobulin dimer permeability were respectively 83.7% and 13.7%, and the permeability ratio was 0.16 (equal to that of Example 39). However, a large amount of permeation solution was obtained by the immunoglobulin aggregate removal step (i.e., a large permeation solution tank was required).

The immunoglobulin concentration decreased to 0.9 g/L in the immunoglobulin aggregate separation step. However, the immunoglobulin concentration could be increased to 9.4 g/L (concentration rate: 10.4) by the immunoglobulin concentration step (equal to that of Example 39). However, since a large amount of filtrate was obtained by the immunoglobulin concentration step, a large filtrate tank was required. Since the immunoglobulin aggregate removal step and the immunoglobulin concentration step were performed separately, the total operation time increased to more than 10 hours.

Therefore, cost and the installation area increase due to a large tank. Moreover, productivity decreases.

Example 40

The hollow fiber membranes (PSf-1) were bundled so that the total hollow cross-sectional area was 0.01 m$^2$ to obtain a fiber bundle for evaluating the human immunoglobulin monomer/dimer fractionation performance and the fibrinogen fractionation performance. The fiber bundle was connected to the cross-flow filtration apparatus shown in FIG. 3. A solution containing a human immunoglobulin (10 g/L) and fibrinogen (manufactured by Sigma, type I-S, molecular weight: 340,000) was introduced into the immunoglobulin stock solution tank (4) of the cross-flow filtration apparatus shown in FIG. 3. The supply pump 2 (3) was rotated while adjusting the control valve 1 (7) so that the linear velocity inside the hollow fiber membrane was 10 cm/sec and the average value of the inlet pressure and the outlet pressure was 0.027 MPa. Since the concentration of the fractionation performance evaluation solution increases as cross-flow filtration proceeds, a PBS aqueous solution contained in the diluent tank (1) was added to the immunoglobulin stock solution tank (4) so that the concentration of the bovine immunoglobulin was constant (10 g/L). The solution was subjected to cross-flow filtration at 25° C. for five hours. The content of the human immunoglobulin monomer, the human immunoglobulin dimer, and fibrinogen was measured by GPC. The monomer permeation amount was 88 g/m$^2$, and the dimer permeation amount was 1.0 g/m$^2$. The human immunoglobulin monomer permeability and the human immunoglobulin dimer permeability were respectively 80.6% and 10.4%, and the permeability ratio (fractionation performance) was 0.13. The fibrinogen permeability was 1.6%. The ratio of the fibrinogen permeability to the monomer permeability (fibrinogen permeability/monomer permeability) was as low as 0.02. Specifically, fibrinogen (high-molecular-weight component) could be removed.

Example 41

The hollow fiber membranes (PSf-2) were bundled so that the total hollow cross-sectional area was 0.02 m$^2$ to obtain a fiber bundle for evaluating the human immunoglobulin monomer/dimer fractionation performance and the fibrinogen fractionation performance. The fiber bundle was connected to the cross-flow filtration apparatus shown in FIG. 3.

A solution containing a human immunoglobulin (10 g/L), fibrinogen (manufactured by Sigma, type I-S, molecular weight: 340,000), and lysine hydrochloride (50 g/L) was introduced into the immunoglobulin stock solution tank (4) of the cross-flow filtration apparatus shown in FIG. 3. The supply pump 2 (3) was rotated while adjusting the control valve 1 (7) so that the linear velocity inside the hollow fiber membrane was 10 cm/sec and the outlet pressure was 0.01 MPa. Since the concentration of the human immunoglobulin solution increases as cross-flow filtration proceeds, a PBS aqueous solution containing lysine hydrochloride (50 g/L) contained in the diluent tank (1) was added to the immunoglobulin stock solution tank (4) so that the concentration of the human immunoglobulin was constant (10 g/L). The solution was subjected to cross-flow filtration at 25° C. until the entire solution was filtered. The content of the human immunoglobulin monomer, the human immunoglobulin dimer, and fibrinogen was measured by GPC. The monomer permeation amount was 41.6 g/m$^2$, and the dimer permeation amount was 0.40 g/m$^2$. The human immunoglobulin monomer permeability and the human immunoglobulin dimer permeability were respectively 91.5% and 11.4%, and the permeability ratio (fractionation performance) was 0.11. The fibrinogen permeability was 2.75%. The ratio of the fibrinogen permeability to the monomer permeability (fibrinogen permeability/monomer permeability) was as low as 0.03. Specifically, fibrinogen (high-molecular-weight component) could be removed.

INDUSTRIAL APPLICABILITY

The separation method according to the present invention may be suitably utilized in the biomedicine (e.g., immunoglobulin) separation/purification field.

The invention claimed is:

1. A method of separating an immunoglobulin monomer comprising filtering an immunoglobulin solution containing at least an immunoglobulin monomer and an immunoglobulin aggregate and having an immunoglobulin concentration of 1 to 150 g/L with cross-flow filtration using an ultrafiltration membrane having a molecular weight cut-off of 100,000 or more and less than 500,000, forming a cake layer on the surface of the ultrafiltration membrane, maintaining the immunoglobulin concentration in an immunoglobulin stock solution during filtration within the range of 50 to 200 when the immunoglobulin concentration before filtration is referred to as 100, and passing the immunoglobulin monomers through the cake layer to obtain an immunoglobulin permeation solution.

2. A method of separating an immunoglobulin monomer from an immunoglobulin aggregate comprising filtering an immunoglobulin solution having an immunoglobulin concentration of 1 to 150 g/L with cross-flow filtration using an ultrafiltration membrane having a molecular weight cut-off of 100,000 or more and less than 500,000, forming a cake layer on the surface of the ultrafiltration membrane, maintaining the immunoglobulin concentration during filtration within the range of 50 to 200 when the immunoglobulin concentration of an immunoglobulin stock solution before filtration is referred to as 100, and passing the immunoglobulin monomers through the cake layer to obtain an immunoglobulin permeation solution.

3. The method according to claim 1, wherein the aggregate includes at least an immunoglobulin dimer.

4. The method according to claim 1, wherein the immunoglobulin solution has an immunoglobulin concentration of 1 to 100 g/L.

5. The method according to claim 1, wherein the immunoglobulin solution has an immunoglobulin concentration of 5 to 100 g/L.

6. The method according to claim 1, wherein 50% or more of the immunoglobulin monomer is separated by the method.

7. The method according to claim 1, wherein the immunoglobulin solution further contains at least one biocomponent selected from proteins having a molecular weight of 300,000 or more and less than 1,000,000, sugar chains, RNA, and DNA.

8. The method according to claim 7, wherein the immunoglobulin solution further contains at least one biocomponent selected from proteins having a molecular weight of 300,000 or more and less than 1,000,000.

9. The method according to claim 8, wherein the protein is at least one protein selected from the group consisting of an immunoglobulin aggregate, fibrinogen, and a composite aggregate of an immunoglobulin and protein A.

10. The method according to claim 1, wherein the immunoglobulin solution further contains a virus.

11. The method according to claim 10, wherein the virus is a parvovirus.

12. The method according to claim 1, wherein the immunoglobulin is a monoclonal antibody.

13. The method according to claim 1, wherein the ultrafiltration membrane is formed of at least one polymer selected from the group consisting of a polysulfone polymer, an aromatic ether polymer, a (meth)acrylic polymer, a (meth)acrylonitrile polymer, a fluorinated polymer, an olefin polymer, a vinyl alcohol polymer, and a cellulose polymer.

14. The method according to claim 13, wherein the polymer is a polysulfone polymer.

15. The method according to claim 14, wherein the polysulfone polymer is at least one polysulfone polymer selected from polysulfone polymers shown by the following formulas (1) to (3), or a mixture of two or more of the polysulfone polymers shown by the following formulas (1) to (3),

[Chem 1]

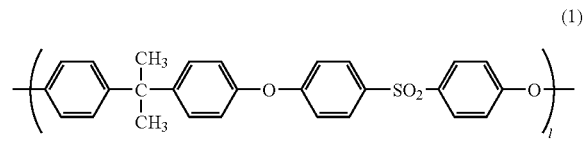

(1)

wherein l represents the number of repeating units,

[Chem 2]

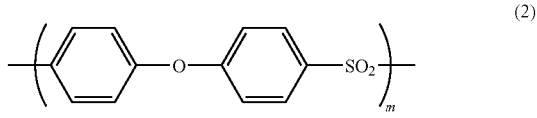

(2)

wherein m represents the number of repeating units,

[Chem 3]

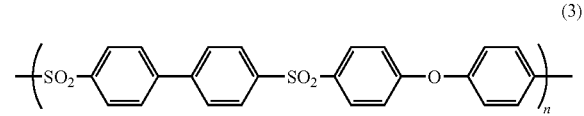

(3)

wherein n represents the number of repeating units.

16. The method according to claim 14, wherein the polysulfone polymer has been hydrophilized with polyvinylpyrrolidone.

17. The method according to claim 13, wherein the polymer is an aromatic ether polymer.

18. The method according to claim 17, wherein the aromatic ether polymer is at least one aromatic ether polymer shown by the following formula (4), and has been hydrophilized with a block copolymer of polystyrene and a hydrophilic polymer,

[Chem 4]

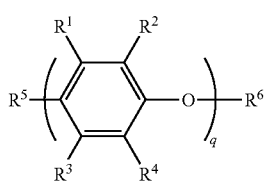

(4)

wherein $R^1$, $R^2$, $R^3$, $R^4$, $R^5$, and $R^6$ individually represent hydrogen, an organic functional group having 1 to 6 carbon atoms, or a non-protonic organic functional group having at most 6 carbon atoms and containing oxygen, nitrogen, or silicon, and q represents the number of repeating units, provided that the aromatic ether polymer may be a copolymer containing two or more different repeating units.

19. The method according to claim 18, wherein the hydrophilic polymer is a polyethylene glycol polymer and/or a polymer containing a segment derived from a polyethylene glycol polymer.

20. The method according to claim 1, wherein the immunoglobulin solution further contains a surfactant.

21. The method according to claim 20, wherein the surfactant is an amphoteric surfactant.

22. The method according to claim 21, wherein the amphoteric surfactant is selected from the group consisting of lysine, alanine, cysteine, glycine, serine, proline, arginine, and derivatives thereof.

23. The method according to claim 22, wherein the amphoteric surfactant is arginine and/or an arginine derivative.

24. The method according to claim 22, wherein the amphoteric surfactant is lysine and/or a lysine derivative.

25. The method according to claim 20, wherein the surfactant is a non-ionic surfactant.

26. The method according to claim 25, wherein the non-ionic surfactant is polyethylene glycol and/or a polyethylene glycol derivative.

27. The method according to claim 26, wherein the polyethylene glycol and/or the polyethylene glycol derivative have a number average molecular weight of 50 to 30,000 Da.

28. The method according to claim 1, further comprising recycling an immunoglobulin permeation solution to an immunoglobulin stock solution until a given time is reached after starting filtration.

29. The method according to claim 28, wherein the given time for recycling an immunoglobulin permeation solution to an immunoglobulin stock solution is set as a time when the percentage of immunoglobulin dimers contained in the immunoglobulin permeation solution has reached 1% or less.

30. The method according to claim 28, wherein the given time for recycling an immunoglobulin permeation solution to an immunoglobulin stock solution is set as a time when the ratio of immunoglobulin dimer permeability to immunoglobulin monomer permeability has reached 0.1 or less.

31. The method according to claim 1, the method being used after purifying the immunoglobulin solution by affinity chromatography.

32. The method according to claim 31, wherein the affinity chromatography utilizes protein A and/or a protein A derivative as an adsorbent.

33. The method according to claim 1, wherein the ultrafiltration membrane is a hollow fiber membrane.

34. The method according to claim 1, the method being implemented using an apparatus that comprises at least one of (a) means that monitors the concentration of the immunoglobulin stock solution, (b) means that controls the concentration of the immunoglobulin stock solution, (c) means that controls the linear velocity of the immunoglobulin stock solution, and (d) means that controls the filtration pressure through the ultrafiltration membrane.

35. A separation/concentration method comprising a separation step that implements the method according to claim 1, and a concentration step that concentrates the immunoglobulin permeation solution obtained by the separation step using a ultrafiltration membrane for concentration, the separation step and the concentration step being performed continuously.

36. The separation/concentration method according to claim 35, wherein the ultrafiltration membrane for concentration has a molecular weight cut-off of 1,000 or more and less than 100,000.

37. The separation/concentration method according to claim 35, wherein the concentration of the immunoglobulin permeation solution subjected to the separation step is 0.1 to 149 g/L, and cross-flow filtration is performed in the concentration step at a linear velocity 0.01 to 100 cm/sec and a pressure of 0.01 to 0.5 MPa.

38. The separation/concentration method according to claim 35, wherein the concentration of the immunoglobulin permeation solution subjected to the separation step is 0.1 to 99 g/L, and cross-flow filtration is performed in the concentration step at a linear velocity 0.01 to 100 cm/sec and a pressure of 0.01 to 0.5 MPa.

39. The separation/concentration method according to claim 35, the method being implemented using a module utilizing the ultrafiltration membrane, at least one of
 (a) means that monitors the concentration of the immunoglobulin stock solution, (b) means that controls the concentration of the immunoglobulin stock solution, (c) means that controls the linear velocity of the immunoglobulin stock solution, and (d) means that controls the filtration pressure through the ultrafiltration membrane, and
a module utilizing the ultrafiltration membrane for concentration, and at least one of (e) means that monitors the concentration of the immunoglobulin permeation solution before concentration, (f) means that monitors the concentration of the immunoglobulin permeation solution after concentration, (g) means that controls the linear velocity of the immunoglobulin permeation solution, and (h) means that controls the filtration pressure through the ultrafiltration membrane for concentration.

* * * * *